US007915481B2

(12) United States Patent
Gallie et al.

(10) Patent No.: US 7,915,481 B2
(45) Date of Patent: Mar. 29, 2011

(54) MAIZE ETR2 GENE AND USES THEREOF

(75) Inventors: Daniel R. Gallie, Riverside, CA (US); Todd E. Young, Palm Springs, CA (US)

(73) Assignee: The Regents of the University of California, Oakland, CA (US)

( * ) Notice: Subject to any disclaimer, the term of this patent is extended or adjusted under 35 U.S.C. 154(b) by 163 days.

(21) Appl. No.: 12/366,490

(22) Filed: Feb. 5, 2009

(65) Prior Publication Data

US 2010/0281556 A1 Nov. 4, 2010

Related U.S. Application Data

(62) Division of application No. 10/876,086, filed on Jun. 23, 2004, now Pat. No. 7,504,557.

(60) Provisional application No. 60/480,960, filed on Jun. 23, 2003.

(51) Int. Cl.
*C12N 15/82* (2006.01)
*A01H 5/00* (2006.01)
*C07H 21/04* (2006.01)

(52) U.S. Cl. ........ 800/283; 800/278; 800/282; 800/290; 800/298; 536/23.6; 435/320.1

(58) Field of Classification Search .................. None
See application file for complete search history.

(56) References Cited

U.S. PATENT DOCUMENTS

| 5,702,933 | A | 12/1997 | Klee et al. |
| 6,294,716 | B1 | 9/2001 | Meyerowitz et al. |
| 6,677,502 | B1 | 1/2004 | Allen et al. |
| 2007/0099303 | A1 | 5/2007 | Orth et al. |

OTHER PUBLICATIONS

Sakai et al. ETR2 is an ETR1-like gene involved in ethylene signaling in Arabidopsis. (1998) PNAS; vol. 95; pp. 5812-5817.*
Chang et al., "*Arabidopsis* Ethylene-Response Gene *ETR1*: Similarity of Product of Two-Component Regulators," *Science*, 1993, pp. 539-544, vol. 262.
De Martinis and Mariani, "Silencing Gene Expression of the Ethylene-Forming Enzyme Results in a Reversible Inhibition of Ovule Development in Transgenic Tobacco Plants," *The Plant Cell*, Jun. 1999, pp. 1061-1071, vol. 11, American Society of Plant Physiologists.
Gepstein and Thimann, "The Role of Ethylene in the Senescence of Oat Leaves," *Plant Physiol.*, 1981, pp. 349-354, vol. 68.
Grossman, K. et al., "Regulation of Phytohormone Levels, Leaf Senescence and Transpiration by the Strobilurin Kresoxim-methyl in Wheat (*Triticum aestivum*)," *J. Plant Phys.*, 1999, pp. 805-808, vol. 154.
Guo, H. H. et al., "Protein tolerance to random amino acid change," *PNAS*, Jun. 22, 2007, pp. 9205-9210, vol. 101, No. 25.
Hill and Preiss, "Functional Analysis of Conserved Histidines in ADS-Glucose Pyrophosphorylase from *Escherichia coli*" *Biochemical and Biophysical Research Communications*, 1998, pp. 573-577, vol. 244.

Hua and Meyerowitz, "Ethylene Responses are Negatively Regulated by a Receptor Gene Family in *Arabidopsis thaliana*," *Cell*, Jul. 24, 1998, pp. 261-271, vol. 94, Cell Press.
Hua et al., "*EIN4* and *ERS2* Are Members of the Putative Ethylene Receptor Gene Family in Arabidopsis," *Plant Cell*, 1998, pp. 1321-1332, vol. 10.
Hua et al., "Ethylene Insensitivity Conferred by *Arabidopsis ERS* Gene," *Science*, 1995, pp. 1712-1714, vol. 269.
Lazar, E. et al., "Transforming Growth Factor α: Mutation of Aspartic Acid 47 and Leucine 48 Results in Different Biological Activities," *Molecular and Cellular Biology*, Mar. 1988, pp. 1247-1252, vol. 8, No. 3.
Maeda et al., "A two-component system that regulates an osmosensing MAP kinase cascade in yeast," *Nature*, 1994, pp. 242-245, vol. 369.
Parkinson and Kofoid, "Communication Modules in Bacterial Signaling Proteins " *Annu. Rev. Genet.*, 1992, pp. 71-112, vol. 26.
Sakai et al., "*ETR2* is an *ETR1*-like gene involved in ethylene signaling in *Arabidopsis*," *Proc. Natl. Acad. Sci. USA*, 1998, pp. 5812-5817, vol. 95.
Sakakibara, H., ZmETR2 (2000) GenBank Accession AB040406, pp. 1-3.
Schaller and Bleeker, "Ethylene-Binding Sites Generated in Yeast Expressing the *Arabidopsis ETR1* Gene," *Science*, 1995, pp. 1809-1811, vol. 270.
Schuster et al., "The hybrid histidine kinase DokA is part of the osmotic response system of *Dictyostelium*," *EMBO J.*, 1996, pp. 3880-3889, vol. 15.
Thomas and Howarth, "Five ways to stay green," *Journal of Experimental Botany*, Feb. 2000, pp. 329-337, vol. 51, Oxford University Press.
Van Der Straeten, D. et al., "Ethylene: A small hormone with many functions," *Med. Fac. Landbouww. Univ. Gent.*, 1995, pp. 1567-1574, vol. 60, No. 4a.
Yip, W. et al., "The effects of antisense *LE-ACS2* and *LE-ACS4* transgenes on ethylene biosynthesis and fruit development in tomato," *Annual Meeting of the American Society of Plant Biologists*, 2002, Abstract No. 368, Denver, CO.
Young et al., "Ethylene-Mediated Programmed Cell Death during Maize Endosperm Development of Wild-Type and *shrunken2* Genotypes," *Plant Physiol.*, 1997, pp. 737-751, vol. 119.
Young and Gallie, "Analysis of programmed cell death in wheat endosperm reveals differences in endosperm development between cereals," *Plant Mol. Biol.*, 1999, pp. 915-926, vol. 39.

(Continued)

*Primary Examiner* — Cathy Kingdon Worley
(74) *Attorney, Agent, or Firm* — Kilpatrick Townsend & Stockton LLP

(57) ABSTRACT

The present invention provides new methods of delaying senescence in a plant by inhibiting ACC oxidase, or EIN2 activity in the plant. In particular, it is directed to producing green leaves in maize through inhibition of ethylene. The genes involved in producing this phenotype include ACC deaminase, ethylene response sensor ("ERS"), ethylene resistant ("ETR"), and ethylene insensitive ("EIN"). The delay in senescence can be achieved through the production of ACC deaminase, mutated ETR1 and ERS2 proteins, as well as overexpression of wild-type ETR1 and ERS2 proteins.

10 Claims, No Drawings

OTHER PUBLICATIONS

Young and Gallie, "Regulation of programmed cell death in maize endosperm by abscisic acid," *Plant Mol. Biol.*, 2000, pp. 397-414, vol. 42.

Zacarias and Reid, "Role of growth regulators in the senescence of *Arabidopsis thaliana* leaves," *Physiologia Plantarum*, 1990, pp. 549-554, vol. 80, Copenhagen.

* cited by examiner

SEQUENCE LISTING

<160> NUMBER OF SEQ ID NOS: 50

<210> SEQ ID NO 1
<211> LENGTH: 2959
<212> TYPE: DNA
<213> ORGANISM: Zea mays
<220> FEATURE:
<223> OTHER INFORMATION: Zea mays (B73) 1-aminocyclopropane-1-
      carboxylate (ACC) oxidase, O15 genomic DNA

<400> SEQUENCE: 1

```
tcgcgaggcg gcttaaactt aggtcggctc ggagtggctc atgagcctcg agcgagcaga      60
gacgaaccga gccaagttgt agagctcatt ggtataacaa gccgagtcag tttgcaagtt     120
atgccaaatt aatgaatcta taaaataata atagatattg gataattta tagatattcg      180
actcgttcct tatcatttaa tgatggattt atgataattt aaaatttaga ttacttataa     240
tgttaaatga tggtcatatt tcatatctat atacaataat agtcattgta taatgcaata     300
ttatttatca aggtgtagct cgcgagttga gtcgagcctc cttcttaatc ttattgagtg     360
gacgaaccaa gctgagccga gtcgagcttg gtcacccagc gagtcgagcc tccttcttaa     420
actcgttgaa tgagactcag ctcatttcta gccctaaaaa atcgcatcat catcggcata     480
aagcgagcaa tgcagacatt tttggtagta caagcttcgg atgaccggct gcagacgctt     540
tctcaataac cttctgtagg ggatcaatgg ccaagatgaa gagggtcac cttgatgaag      600
acttcaggcg tgtttaaatt ttttgcttgg gcgatcattc actagcactt tggaagatga     660
tgtagccaag atgctagtct ctctattttt gactgaaacc tagctagagc ttttaaaaca     720
tcccggagat agttaaggga atcaaaggct tttgaaatgt ccaatagata ccattttttt     780
tcttgtggag gaggctatga ataacatttt gttcatatag aaaattatca cattatgtaa     840
caagcaaggg aaaataactt atatatagtt aatagtggag ggagtgtctg atataaaaag     900
ctacatattt ttgctggtta gttgttagtt aggtctttac ctgccctctc tctacgaacg     960
agctgatgcc agttctgact ttgtcaaagc atggctggca atgtgattga atgcctgatg    1020
ttagctcgtc accttgacag ggacatccga tcctgaattt ccgattgggg tggcaaaggt    1080
caagttgcca ccacaagcat cagtccaatg gctctgccac tgcccagaag cttcatcaca    1140
cctagaggta gccatgacag gacccaaaaa aaggtccagt ccaggtccgt accagctgcg    1200
```

-continued

| | |
|---|---|
| acgacgcttg tcagtaggta ggttgagcta gctgcttgtt gatcactgct atatatacgg | 1260 |
| gtgccatgga tccatgcctt ctccatcctc aagtcatcag ctagctagcc ttccctacag | 1320 |
| caactgctta catacaacac ttccatcttc ccgagctcgt cttcgatcaa ttcccaagtc | 1380 |
| aaataataat ataacaacaa tggtggttcc cgtcatcgac ttctccaagc tggacggcgc | 1440 |
| tgagagggcc gaaaccctgg cgcagatcgc caatggctgc gaggagtggg gattcttcca | 1500 |
| gctcgtgaac cacggcatcc cgctggagct tcttgagcgc gtcaagaagg tgagctccga | 1560 |
| ctgctaccgc ctccgggagg ccgggttcaa ggcgtcggag ccggtgcgca cgctggaggc | 1620 |
| gctcgtcgac gcggagcggc gcggcgaggt tgtggccccg gtggatgacc tggactggga | 1680 |
| ggacatcttc tacatccacg acggatgcca gtggccgtcc gagccgccgg cgttcaagga | 1740 |
| gaccatgcgc gagtaccgcg ccgagctgag gaagctcgcc gagcgcgtca tggaggccat | 1800 |
| ggacgagaac ctcggcctcg ccaggggcac catcaaggac gccttctcca gcggcggccg | 1860 |
| gcacgagccc ttcttcggca ccaaggtcag ccactacccg ccgtgcccgc gcccggacct | 1920 |
| catcacgggc ctgcgcgcgc acaccgacgc cggcggcgtc atcctgctgt tccaggacga | 1980 |
| cagggtcggc ggcctggagg tgctcaagga cggccagtgg accgacgtgc agccgctcgc | 2040 |
| gggcgccatc gtcgtcaaca ctggcgacca gattgaggtg ctcagcaacg ggcgctaccg | 2100 |
| cagcgcctgg caccgcgtgc tgcccatgcg cgacggcaac cgccgctcca tcgcttcctt | 2160 |
| ctacaacccg gccaacgagg ccaccatctc gccggcggcg gtgcaggcca gcggcggcga | 2220 |
| cgcataccc aagtacgtgt tcggcgacta catggacgtg tacgccaagc acaagttcca | 2280 |
| ggccaaggag cccaggttcg aagccgtcaa ggttgcagcg cccaagtcat ctccagcggc | 2340 |
| ataaataaat ggaggggacc aattattaaa tgcattataa tttatttgtt gaataaaaca | 2400 |
| gccggagaaa taatgataat gtaaagtata tatgataaac accggttagg atttaaggtg | 2460 |
| tttaacttta gttgcatggt ataatatgat atattgttgt agcaataagt ttattaagta | 2520 |
| ttcataagtg ttctaaatag tgggctaagg cacttatcca tcgcctttct caaacagaaa | 2580 |
| atagtgattt aattcgggct atagcgacta atagttgcta tatatattag gcgtagtagc | 2640 |
| aaacaatttc ccccttttgga aacagttata tctagaaata actatagcca gagatttaga | 2700 |
| accttgttaa tcatgtagaa attaaaggtt cgtcaagtca gagcggcacc gaacaagata | 2760 |
| aaaatgtgac ctcccctata tgcaaatgtc tgccaactta ttcattggt gggtgccatc | 2820 |
| ttactatgta caaatatatc gcggaaacca tattatcagc gtcgagaatt ggccataccc | 2880 |
| ctggatattg ataatatgcc ttgcgagatc tattgagctg aagaaaactc gtaggggtc | 2940 |
| tagctagtgc catacctaa | 2959 |

<210> SEQ ID NO 2
<211> LENGTH: 940
<212> TYPE: DNA
<213> ORGANISM: Zea mays
<220> FEATURE:
<223> OTHER INFORMATION: Zea mays (B73) 1-aminocyclopropane-1-
      carboxylate (ACC) oxidase, O15 coding sequence (CDS)

<400> SEQUENCE: 2

| | |
|---|---|
| atggtggttc ccgtcatcga cttctccaag ctggacggcg ctgagagggc cgaaaccctg | 60 |
| gcgcagatcg ccaatggctg cgaggagtgg ggattcttcc agctcgtgaa ccacggcatc | 120 |
| ccgctggagc ttcttgagcg cgtcaagaag gtgagctccg actgctaccg cctccgggag | 180 |
| gccgggttca aggcgtcgga gccggtgcgc acgctggagg cgctcgtcga cgcggagcgg | 240 |
| cgcggcgagg ttgtggcccc ggtggatgac ctggactggg aggacatctt ctacatccac | 300 |

```
gacggatgcc agtggccgtc cgagccgccg gcgttcaagg agaccatgcg cgagtaccgc    360
gccgagctga ggaagctcgc cgagcgcgtc atggaggcca tggacgagaa cctcggcctc    420
gccaggggca ccatcaagga cgccttctcc agcggcggcc ggcacgagcc cttcttcggc    480
accaaggtca gccactaccc gccgtgcccg cgcccggacc tcatcacggg cctgcgcgcg    540
cacaccgacg ccggcggcgt catcctgctg ttccaggacg acagggtcgg cggcctggag    600
gtgctcaagg acgccagtg gaccgacgtg cagccgctcg cgggcgccat cgtcgtcaac    660
actggcgacc agattgaggt gctcagcaac gggcgctacc gcagcgcctg gcaccgcgtg    720
ctgcccatgc gcgacggcaa ccgccgctcc atcgcttcct tctacaaccc ggccaacgag    780
gccaccatct cgccggcggc ggtgcaggcc agcggcggcg acgcataccc caagtacgtg    840
ttcggcgact acatggacgt gtacgccaag cacaagttcc aggccaagga gcccaggttc    900
gaagccgtca aggttgcagc gcccaagtca tctccagcgg                         940
```

<210> SEQ ID NO 3
<211> LENGTH: 314
<212> TYPE: PRT
<213> ORGANISM: Zea mays
<220> FEATURE:
<223> OTHER INFORMATION: Zea mays (B73) 1-aminocyclopropane-1-
    carboxylate (ACC) oxidase, O15 protein

<400> SEQUENCE: 3

```
Met Val Val Pro Val Ile Asp Phe Ser Lys Leu Asp Gly Ala Glu Arg
  1               5                  10                  15

Ala Glu Thr Leu Ala Gln Ile Ala Asn Gly Cys Glu Glu Trp Gly Phe
             20                  25                  30

Phe Gln Leu Val Asn His Gly Ile Pro Leu Glu Leu Leu Glu Arg Val
         35                  40                  45

Lys Lys Val Ser Ser Asp Cys Tyr Arg Leu Arg Glu Ala Gly Phe Lys
     50                  55                  60

Ala Ser Glu Pro Val Arg Thr Leu Glu Ala Leu Val Asp Ala Glu Arg
 65                  70                  75                  80

Arg Gly Glu Val Val Ala Pro Val Asp Asp Leu Asp Trp Glu Asp Ile
                 85                  90                  95

Phe Tyr Ile His Asp Gly Cys Gln Trp Pro Ser Glu Pro Pro Ala Phe
            100                 105                 110

Lys Glu Thr Met Arg Glu Tyr Arg Ala Glu Leu Arg Lys Leu Ala Glu
        115                 120                 125

Arg Val Met Glu Ala Met Asp Glu Asn Leu Gly Leu Ala Arg Gly Thr
    130                 135                 140

Ile Lys Asp Ala Phe Ser Ser Gly Gly Arg His Glu Pro Phe Phe Gly
145                 150                 155                 160

Thr Lys Val Ser His Tyr Pro Pro Cys Pro Arg Pro Asp Leu Ile Thr
                165                 170                 175

Gly Leu Arg Ala His Thr Asp Ala Gly Gly Val Ile Leu Leu Phe Gln
            180                 185                 190

Asp Asp Arg Val Gly Gly Leu Glu Val Leu Lys Asp Gly Gln Trp Thr
        195                 200                 205

Asp Val Gln Pro Leu Ala Gly Ala Ile Val Val Asn Thr Gly Asp Gln
    210                 215                 220

Ile Glu Val Leu Ser Asn Gly Arg Tyr Arg Ser Ala Trp His Arg Val
225                 230                 235                 240

Leu Pro Met Arg Asp Gly Asn Arg Arg Ser Ile Ala Ser Phe Tyr Asn
```

```
                    245                 250                 255
Pro Ala Asn Glu Ala Thr Ile Ser Pro Ala Val Gln Ala Ser Gly
            260                 265                 270
Gly Asp Ala Tyr Pro Lys Tyr Val Phe Gly Asp Tyr Met Asp Val Tyr
        275                 280                 285
Ala Lys His Lys Phe Gln Ala Lys Glu Pro Arg Phe Glu Ala Val Lys
    290                 295                 300
Val Ala Ala Pro Lys Ser Ser Pro Ala Ala
305                 310

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O15 (ZmACO15) forward primer

<400> SEQUENCE: 4
ctcgtcttcg atcaattccc aagt                                           24

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O15 (ZmACO15) reverse primer

<400> SEQUENCE: 5
tacattatca ttatttctcc ggctgt                                         26

<210> SEQ ID NO 6
<211> LENGTH: 1516
<212> TYPE: DNA
<213> ORGANISM: Zea mays
<220> FEATURE:
<223> OTHER INFORMATION: Zea mays (W64) 1-aminocyclopropane-1-
      carboxylate (ACC) oxidase, O20 genomic DNA (truncated)
<220> FEATURE:
<221> NAME/KEY: modified_base
<222> LOCATION: (30)
<223> OTHER INFORMATION: n = g, a, c or t

<400> SEQUENCE: 6
attccgttgc ccctgtcaag tgtacatcan attgaatgct gtgttaggcc agcaactatc    60
acaatcccaa gtcatagcag gtgacggtgc gatcgacgcg cttttgtttgg tggaacattt  120 tcccgtgttc aattctttct tcccttcttt tttttttttaa aaaaaaagct ttccgtgtcg  180
ctgctgcagc aagtgatgaa gcagttcgca tcggaggtgc agaagctgtc ggagaaggtg  240
ctggacttgc tgtgcgagaa cctgggcctg agcccgggt acctgaaggc ggccttcgcg   300
gggtcggacg gcggcccgac gttcggcacc aaggtgagcg cgtacccgcc gtgcccgcgc  360
ccggacctgg tggccggcct gcgcgcgcac accgacgccg gcggcctcat cctgctgctc  420
caggacgacc aggtgagcgg gctgcagctg ctcaggggcg gcgacggcgg ggagtgggtg  480
aacgtgccgc cgctgcgcca cgccatcgtc gccaacgtcg gcgaccagct ggaggtggtc  540
accaacgggc ggtacaagag cgcggtgcac cgcgtgctcg cccgccccga cggcaaccgc  600
atgtccgtcg cgtccttcta caacccgggc gccgacgccg tcatcttccc ggccccgcg  660 ctcgtcggcg aggaggagcg agccgagaag aaggccacca cgtacccgag gttcgtgttc  720
```

```
gaggactaca tgaacctgta cgcgcgccac aagttcgagg ccaaggagcc ccggttcgag    780
gccatgaagt cgtcggccat cgccaccgcg tgagcacata atactgccgt gttctccctt    840
cgtggggtgc atatgcttga gcttgaagag ccatgtgcct gtatgtagtg cacgtacgg     900 tggttatgcg tgtatcgtgg aatggcgcgg cgtgatgtat tttggttgtc tcagatctaa    960
gtgtgtgcgt atatattgtg tactgtaaag tttgcagcgt ctgattaatg tacgagcagt    1020
gtgtgtacct aaccagaacc tggaatgtgg ctggctgtgt gctgatatta ctaccacatc    1080
aggtgagtgg ccaccgtcg tcgcctccta cggctccggt gccgactcga ccccttcctt     1140
ccctgcgacc ctgcggcccc accgcccttta tctccatgga tacttgcggc gagcaaaggc   1200
ttaacaaagg agaacagtgt gcaaaacata cctgcagtga gcaaaggctt acatgagga    1260 tatcaggata tgcacagacc taccatacaa gctatagcct ttcctttaca acaaaacacc   1320
agctagaaga tccgcatatg ctaccgattg ttcactctcc atgttttgtt cggcttacat    1380
tgttacgctg agttagatgg ttaattgcac agtaacctgc cgactgcact atcaccttgt    1440
cttggctttc cttctcttct atacaaaagc gagtcagtgg acacattcag agaagtggaa    1500
gggaagaaag aagaaa                                                    1516

<210> SEQ ID NO 7
<211> LENGTH: 969
<212> TYPE: DNA
<213> ORGANISM: Zea mays
<220> FEATURE:
<223> OTHER INFORMATION: Zea mays (W64) 1-aminocyclopropane-1-
      carboxylate (ACC) oxidase, O20 coding sequence (CDS)

<400> SEQUENCE: 7
atggcagcca cggtgtcctt cccggtggtg aacatggaga agctggagac cgaggagagg     60
gacacggcca tggcggtcat ccgcgacgcc tgcgagaact gggcttctt cgagctgctg    120 aaccatggca tctcgcacga gctgatggac gaggtggagc ggctgaccaa ggcgcactac   180
gccaccttcc gggaggccaa gttccaggag ttcgcggcgc ggacgctggc cgcggccggc   240
gacgagggcg ccgacgtcag cgacgtggac tgggagagca ccttcttcgt ccgccacctc   300
ccggcctcca acctcgccga cctccccgac gtcgacgacc actaccggca agtgatgaag   360
cagttcgcat cggaggtgca gaagctgtcg gagaaggtgc tggacctgct gtgcgagaac   420
ctgggcctgg agcccgggta cctgaaggcg gccttcgcgg ggtcggacgg cggcccgacg   480
ttcggcacca aggtgagcgc gtacccgccg tgcccgcgcc cggacctggt ggccggcctg   540
cgcgcgcaca ccgacgccgg cggcctcatc ctgctgctcc aggacgacca ggtgagcggg   600
ctgcagctgc tcaggggcgg cgacggcggg gagtgggtgg acgtgccgcc gctgcgccac   660
gccatcgtcg ccaacgtcgg cgaccagctg gaggtggtca ccaacgggcg gtacaagagc   720
gcggtgcacc gcgtgctcgc ccgccccgac ggcaaccgca tgtccgtcgc gtccttctac   780
aacccgggcg ccgacgccgt catcttcccg gcccccgcgc tcgtcggcga ggaggagcga   840
gccgagaaga aggccaccac gtacccgagg ttcgtgttcg aggactacat gaacctgtac   900
gcgcgccaca agttcgaggc caaggagccc cggttcgagg ccatgaagtc gtcggccatc   960
gccaccgcg                                                            969

<210> SEQ ID NO 8
<211> LENGTH: 323
<212> TYPE: PRT
<213> ORGANISM: Zea mays
<220> FEATURE:
```

<223> OTHER INFORMATION: Zea mays (W64) 1-aminocyclopropane-1-
carboxylate (ACC) oxidase, O20 protein

<400> SEQUENCE: 8

```
Met Ala Ala Thr Val Ser Phe Pro Val Val Asn Met Glu Lys Leu Glu
 1               5                  10                  15

Thr Glu Glu Arg Asp Thr Ala Met Ala Val Ile Arg Asp Ala Cys Glu
            20                  25                  30

Asn Trp Gly Phe Phe Glu Leu Leu Asn His Gly Ile Ser His Glu Leu
        35                  40                  45

Met Asp Glu Val Glu Arg Leu Thr Lys Ala His Tyr Ala Thr Phe Arg
 50                  55                  60

Glu Ala Lys Phe Gln Glu Phe Ala Ala Arg Thr Leu Ala Ala Ala Gly
 65                  70                  75                  80

Asp Glu Gly Ala Asp Val Ser Asp Val Asp Trp Glu Ser Thr Phe Phe
                85                  90                  95

Val Arg His Leu Pro Ala Ser Asn Leu Ala Asp Leu Pro Asp Val Asp
            100                 105                 110

Asp His Tyr Arg Gln Val Met Lys Gln Phe Ala Ser Glu Val Gln Lys
        115                 120                 125

Leu Ser Glu Lys Val Leu Asp Leu Leu Cys Glu Asn Leu Gly Leu Glu
130                 135                 140

Pro Gly Tyr Leu Lys Ala Phe Ala Gly Ser Asp Gly Gly Pro Thr
145                 150                 155                 160

Phe Gly Thr Lys Val Ser Ala Tyr Pro Pro Cys Pro Arg Pro Asp Leu
                165                 170                 175

Val Ala Gly Leu Arg Ala His Thr Asp Ala Gly Gly Leu Ile Leu Leu
            180                 185                 190

Leu Gln Asp Asp Gln Val Ser Gly Leu Gln Leu Leu Arg Gly Gly Asp
        195                 200                 205

Gly Gly Glu Trp Val Asp Val Pro Pro Leu Arg His Ala Ile Val Ala
210                 215                 220

Asn Val Gly Asp Gln Leu Glu Val Val Thr Asn Gly Arg Tyr Lys Ser
225                 230                 235                 240

Ala Val His Arg Val Leu Ala Arg Pro Asp Gly Asn Arg Met Ser Val
                245                 250                 255

Ala Ser Phe Tyr Asn Pro Gly Ala Asp Ala Val Ile Phe Pro Ala Pro
            260                 265                 270

Ala Leu Val Gly Glu Glu Arg Ala Glu Lys Lys Ala Thr Thr Tyr
        275                 280                 285

Pro Arg Phe Val Phe Glu Asp Tyr Met Asn Leu Tyr Ala Arg His Lys
290                 295                 300

Phe Glu Ala Lys Glu Pro Arg Phe Glu Ala Met Lys Ser Ser Ala Ile
305                 310                 315                 320

Ala Thr Ala
```

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Zea mays
(W64) 1-aminocyclopropane-1-carboxylate (ACC) oxidase,
O20 (ZmACO20) forward primer, ACOF1 primer

<400> SEQUENCE: 9
ctcatcctgc tgctccagga cgac       24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:Zea mays
(W64) 1-aminocyclopropane-1-carboxylate (ACC) oxidase,
O20 (ZmACO20) reverse primer

<400> SEQUENCE: 10
tccacgatac acgcataacc accgt                                      25

<210> SEQ ID NO 11
<211> LENGTH: 942
<212> TYPE: DNA
<213> ORGANISM: Zea mays
<220> FEATURE:
<223> OTHER INFORMATION: Zea mays (B73) 1-aminocyclopropane-1-
carboxylate (ACC) oxidase, O31 coding sequence (CDS)

<400> SEQUENCE: 11
atggtggttc ccgtgatcga cttctccaag ctggacggcg ctgagagggc tgaaaccctg     60
gcgcagatcg ccaatggctg cgaggagtgg ggattcttcc agctcgtgaa ccacggcatc    120
ccgctggagc tgctcgagcg cgtcaagaag gtgtgctccg actgctaccg cctccgggag    180
gccgggttca aggcgtcgga gccggtgcgc acgctggagg cgctcgtcga cgcggagcgg    240
cgcggtgagg tggtggcgcc ggtggacgac ctggactggg aggacatctt ctacatccac    300
gacggatgcc agtggccgtc cgacccgccg gcgttcaagg agaccatgcg cgagtaccgc    360
gccgagctga ggaagctcgc cgagcgagtc atggaggcca tggacgagaa cctcggcctc    420 gccagggca ccatcaagga cgccttctcc ggcggcggcc ggcacgatcc cttcttcggc    480
accaaggtca gccactaccc gccgtgccca cgcccggacc tcatcacggg cctgcgcgcg    540
cacaccgacg ccggcggcgt catcctcctg ttccaggacg acaaggtcgg tggcctggag    600
gtgctcaagg acggcgagtg gaccgacgta cagccgctcg agggcgccat cgtcgtcaac    660
accggcgacc agatcgaggt gctcagcaac gggctgtacc gcagcgcttg gcaccgcgtg    720
ctgcccatgc gcgacggcaa tcgccgctcc atcgcatcct tctacaaccc agccaacgaa    780
gccaccatct cgccggcggc ggtgcaggcc agcggcggtg acgcgtatcc caagtacttg    840
ttcggcgatt acatggacgt gtacgtcaag cagaagttcc aggccaagga gcctaggttc    900
gaagccgtca agacggggc gccaaagtca tctccagcgg ca                        942

<210> SEQ ID NO 12
<211> LENGTH: 314
<212> TYPE: PRT
<213> ORGANISM: Zea mays
<220> FEATURE:
<223> OTHER INFORMATION: Zea mays (B73) 1-aminocyclopropane-1-
carboxylate (ACC) oxidase, O31 protein

<400> SEQUENCE: 12

Met Val Val Pro Val Ile Asp Phe Ser Lys Leu Asp Gly Ala Glu Arg
 1               5                  10                  15

Ala Glu Thr Leu Ala Gln Ile Ala Asn Gly Cys Glu Glu Trp Gly Phe
            20                  25                  30

Phe Gln Leu Val Asn His Gly Ile Pro Leu Glu Leu Leu Glu Arg Val
        35                  40                  45

Lys Lys Val Cys Ser Asp Cys Tyr Arg Leu Arg Glu Ala Gly Phe Lys
    50                  55                  60

```
Ala Ser Glu Pro Val Arg Thr Leu Glu Ala Leu Val Asp Ala Glu Arg
 65                  70                  75                  80

Arg Gly Glu Val Val Ala Pro Val Asp Asp Leu Asp Trp Glu Asp Ile
                 85                  90                  95

Phe Tyr Ile His Asp Gly Cys Gln Trp Pro Ser Asp Pro Ala Phe
            100                 105                 110

Lys Glu Thr Met Arg Glu Tyr Arg Ala Glu Leu Arg Lys Leu Ala Glu
        115                 120                 125

Arg Val Met Glu Ala Met Asp Glu Asn Leu Gly Leu Ala Arg Gly Thr
        130                 135                 140

Ile Lys Asp Ala Phe Ser Gly Gly Arg His Asp Pro Phe Phe Gly
145                 150                 155                 160

Thr Lys Val Ser His Tyr Pro Pro Cys Pro Arg Pro Asp Leu Ile Thr
                165                 170                 175

Gly Leu Arg Ala His Thr Asp Ala Gly Gly Val Ile Leu Leu Phe Gln
            180                 185                 190

Asp Asp Lys Val Gly Gly Leu Glu Val Leu Lys Asp Gly Glu Trp Thr
        195                 200                 205

Asp Val Gln Pro Leu Glu Gly Ala Ile Val Val Asn Thr Gly Asp Gln
        210                 215                 220

Ile Glu Val Leu Ser Asn Gly Leu Tyr Arg Ser Ala Trp His Arg Val
225                 230                 235                 240

Leu Pro Met Arg Asp Gly Asn Arg Arg Ser Ile Ala Ser Phe Tyr Asn
                245                 250                 255

Pro Ala Asn Glu Ala Thr Ile Ser Pro Ala Ala Val Gln Ala Ser Gly
            260                 265                 270

Gly Asp Ala Tyr Pro Lys Tyr Leu Phe Gly Asp Tyr Met Asp Val Tyr
        275                 280                 285

Val Lys Gln Lys Phe Gln Ala Lys Glu Pro Arg Phe Glu Ala Val Lys
        290                 295                 300

Thr Gly Ala Pro Lys Ser Ser Pro Ala Ala
305                 310

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O31 (ZmACO31) forward primer

<400> SEQUENCE: 13
ctcgtcttcg atcaattccc aagt                                          24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O31 (ZmACO31) reverse primer

<400> SEQUENCE: 14
atagcaaaga gggcaactag ctagt                                         25

<210> SEQ ID NO 15
<211> LENGTH: 4336
```

```
<212> TYPE: DNA
<213> ORGANISM: Zea mays
<220> FEATURE:
<223> OTHER INFORMATION: Zea mays (B73) 1-aminocyclopropane-1-
      carboxylate (ACC) oxidase, O35 genomic DNA

<400> SEQUENCE: 15
cttaagattg ggcttcagtg actaacaatc cgcatatata ttcttttggt gctagtttga      60
aaattgaaat cctctccggg atttctgggg attgagactc aatctccagg aatcccgagg     120
tggtttaagt tttaaaacta gtcttaaagt tttaatgcaa taaaatacaa aatttaatgt     180
acttatgtcg gaatttattt ggaacaaata aaaacaggaa tttgctaatt ttggtaggtg     240
gtgcggcggt gaccgaaaaa aacatgaaaa gccgtattca aatctggatt cgttgtggag     300
tacctacgta tgccaatatc tctaaagtat aggattaggc caatagataa ctaggtcata     360
taatagcacc acagccgtat gatatcgtac aatattataa tgtacatcat atatatccag     420
cctaattagc tggggtcagt tgcaataatc ttcagaggac ttgtctgtat ctcgagtagc     480
ccgcataatt gcggctcgcc gtgcccgtgc acacgtctag ttatagatgt gtaaaaaaaa     540
tctgtccact cggtatatgg tccactcagc tcgccgtgca cgcatctagt ttagatgac      600
gcggtgcgat gaaggggtcg cacggaggag gggaggggga gttagggtta gcaggcaagt     660
tgagtggtgt gctggttgtc tagtaaaatc ttagcagact tttgtagatt aggtcatact     720
gtgtcaaact gtcaactgcc gtacacgata ggcgatttgc taaattacca atattattag     780
gccttgttcg gttattccca atacacctgg attgaatgag attggaaaaa attcttaaga     840
actttgaatt gtttgggatt caaacccatc caatcccact caatccacat ggattgagag     900
ctaaccgaac aagcccttag tgggtttcag agattttatc ttcagaccta taaattatag     960
gtgcagatat atagactaaa aaacatagac atagatggta ttatagcaag aaggaacaaa    1020
ttcagtgcta attatttcga atacggtact gcacatccgg actgtcctgt cccagcctct    1080
cccaggttgc atgctcatct acaccgtcga gcgtcgaggc ggctagctct agccgatcag    1140
cgagcatcgc gggctatata cgtccagact gctttcattt gagaatgcgt agtttggctt    1200
cctaatccat ttgagtaaat tatgaaagta atgataaacg taccgtcgcg aggtcactct    1260
ggtaatccaa catttctcgc tcagccgcct ataaattggg ccgcgcgcac cgcctcgctc    1320
tccactcaaa caaactcaag cctgccctgc cctgccttgt taagcaaagc aacccagctg    1380
cgagacacga gagctagcta gagagagatg gcggccacgg tttcctcctt cccggtggtg    1440
aacatggaga agctggagac agaggagagg gccacggcca tggaggtcat ccgcgacggc    1500
tgcgagaact ggggcttctt cgaggtgtgc atatacatac tctgcagact gcttgctgct    1560
cacaccaagc taccacagaa cacaattatt ctactaacca acgcaccaca cctgatcaca    1620
ataagtaatg atctaaccac acagcaggaa gaattactac ttcacttgtt gtttgcctga    1680
cctgccaccc cctgcttct tcaacatcta gagccccttc attctgtcag cacatgcaag    1740
ctgttcgttt cggatcaaat ctatttgttc ggactgctga cagtagaaac cgatactcgt    1800
taaagccagc accaccgttc cagaaaaaga aaagcaaaac aaagtattct agcagcttgc    1860
tttacctaac aaacagcctc cgatcctcga acgtacagat tcctattctc catgccatca    1920
accgccgac caccagctga ttccatcacg tctctctctc accgcgccta gctgatgagc    1980
acacacaaag tagcatctta tctattggtt cgttgatgcc cagctctcga acgaatcacc    2040
atctcatgta ttgtcttgtc cccatcccca tgcatgcagc tgctgaacca cggcatctcg    2100
cacgagctga tggacgaggt ggagcggctg accaaggcgc actacgccac cttccgggag    2160
```

-continued

| | |
|---|---|
| gccaagttcc aggagttcgc ggcccggacg ctggaggccg gcgagaaggg cgccgacgtc | 2220 |
| aaggacgtgg actgggagag caccttcttc gtccgccacc tcccggcctc caacctcgcc | 2280 |
| gacctccccg acgtcgacga ccgctacagg tgcgttcaga cctcaaacac aacactacgt | 2340 |
| gcgtgcgtgc gtgctagcta gctagcttat gcgcgccatt aaattaatga cgtctggcgc | 2400 |
| acagggccgg gccggcataa ttgaaggccc tgtactgttt ttttttcttt tttttctttg | 2460 |
| ttaagaatag atgatacaga ttaatctcat ttattaacag tgattgaatt attaatgtag | 2520 |
| gaaatggctt aataacgata acaaatgatc ttaaagtttg gatttatgc tagcatgtgc | 2580 |
| tagctgcact tcgccatata gccaaaataa gttcatgag agattggtac tcgcttgtta | 2640 |
| cgacaaacac tatgttttat tcttatcgag ctgacttagc tagactttct aatcattact | 2700 |
| aaaatttata ttgattaaat tatcactaac tattattta ggggcccttg aagggagggg | 2760 |
| gccctgttct tgtgcactag tgacacatgc ctcccgcccg ggcctgctgg cgcagtatcg | 2820 |
| tatatttatt agtgtttggc tgctagctgc gacccaatga tcagtcgtct ttgttaatcg | 2880 |
| acttttgtt ggcttctgac ggatgttcta agtgccatgt cacccgcttt tgactgatca | 2940 |
| gtttattta attgatctga ttagtcttag cttgagagtg acttgagtat agcaggctgg | 3000 |
| gatactacct gacctgctcc tacataacgg attaagtaat gtttcaagaa attttgtcca | 3060 |
| tacgcatata attaagttat cattatcaga attctgcctg acgacgacga cgacgacgcg | 3120 |
| aaaacagtta gttatctgtt catctcgttg cctttaattg cttgacaagc tagctagcta | 3180 |
| gctgtacagc agaatgcggt gcgagccccg tagctatgac aaggtcgatc gaatcgcctt | 3240 |
| ttcagcaggc gacagcgcta tttgtccggt ggaattattc cggccgtgtc tcaaagcctt | 3300 |
| ccttccgtac gtgtcgctgc aggcaggtga tggagcagtt cgcatcggag atccgcaagc | 3360 |
| tgtcggagag gctgctggac ctgctgtgcg agaacctggg cctggagccc gggtacctga | 3420 |
| aggcggcctt cgcggggtcg gacgcccga cgttcggcac caaggtgagc gcgtacccgc | 3480 |
| cgtgcccgcg cccggacctc gtcgacgcc tccgcgcgca caccgacgcc ggcggcatcg | 3540 |
| tgctgctgtt ccaggacgac caggtgagcg gcctgcagct gctcaggggc ggggagtggg | 3600 |
| tggacgtgcc gcccatgcgc cacgccatcg tcgccaacgt cggcgaccag ctggaggtga | 3660 |
| tcaccaacgg gcggtacaag agcgtcatgc accgcgtgct cacgcgcccc gacggcaacc | 3720 |
| gcatgtccgt cgcgtccttc tacaacccgg gcgccgacgc cgtcatcttc ccggcccccg | 3780 |
| cgctcgtcgg cgccgccgag gaggaccgcg ccgaggccgc gtacccgagc ttcgtgttcg | 3840 |
| aggactacat gaacctgtac gtgcgccaca gttcgaggc caaggagccc aggttcgagg | 3900 |
| ccatgaagtc ggccatcgcc accgcgtgag agaagactgc cttccgctgc aggcttcctt | 3960 |
| cgtggcgtca agccttgagg cttgaacgaa caacgtacgt ccatgtgctt atagtggcac | 4020 |
| agttatgtgt gtaactaccg atcgtggaac ggcctaatgt atttcggttg cctcagatcg | 4080 |
| atctatatgt gcgtatacat tatgtactga aaagtgtgta gcgtctggtt aatgtatgag | 4140 |
| cagtgtgtat gtgaccggga cccggtgtgt agttgctatt actaccatat ccggtgaatg | 4200 |
| atcaaacctt ttggtgtatt aaaactagat gttcatcccc tcacggacta ccctggtatt | 4260 |
| gacaaccaaa acggaatatg acatatatag taaaaacatg atttcccggc caagaaaggg | 4320 |
| gactattcca actcgg | 4336 |

<210> SEQ ID NO 16
<211> LENGTH: 951
<212> TYPE: DNA
<213> ORGANISM: Zea mays
<220> FEATURE:

```
<223> OTHER INFORMATION: Zea mays (B73) 1-aminocyclopropane-1-
      carboxylate (ACC) oxidase, O35 coding sequence (CDS)
<220> FEATURE:
<221> NAME/KEY: modified_base
<222> LOCATION: (58)
<223> OTHER INFORMATION: n = g, a, c or t

<400> SEQUENCE: 16
atggcggcca cggtttcctc cttcccggtg gtgaacatgg agaagctgga gacagaggag      60
agggccacgg ccatggaggt catccgcgac ggctgcgaga actggggctt cttccagctg     120
ctgaaccacg gcatctcgca cgagctgatg gacgaggtgg agcggctgac caaggcgcac     180
tacgccacct tccgggaggc caagttccag gagttcgcgg cccggacgct ggaggccggc     240
gagaagggcg ccgacgtcaa ggacgtggac tgggagagca ccttcttcgt ccgccacctc     300
ccggcctcca acctcgccga cctccccgac gtcgacgacc gctacaggca ggtgatggag     360
cagttcgcat cggagatccg caagctgtcg gagaggctgc tggacctgct gtgcgagaac     420
ctgggcctgg agcccgggta cctgaaggcg gccttcgcgg ggtcggacgg cccgacgttc     480
ggcaccaagg tgagcgcgta cccgccgtgc ccgcgcccgg acctcgtcga cggcctccgc     540
gcgcacaccg acgccggngg catcgtgctg ctgttccagg acgaccaggt gagcggcctg     600
cagctgctca ggggcgggga gtgggtggac gtgccgccca tgcgccacgc catcgtcgcc     660
aacgtcggcg accagctgga ggtgatcacc aacgggcggt acaagagcgt catgcaccgc     720
gtgctcacgc gccccgacgg caaccgcatg tccgtcgcgt ccttctacaa cccgggcgcc     780
gacgccgtca tcttcccggc ccccgcgctc gtcggcgccg ccgaggagga ccgcgccgag     840
gccgcgtacc cgagcttcgt gttcgaggac tacatgaacc tgtacgtgcg ccacaagttc     900
gaggccaagg agcccaggtt cgaggccatg aagtcggcca tcgccaccgc g              951

<210> SEQ ID NO 17
<211> LENGTH: 317
<212> TYPE: PRT
<213> ORGANISM: Zea mays
<220> FEATURE:
<223> OTHER INFORMATION: Zea mays (B73) 1-aminocyclopropane-1-
      carboxylate (ACC) oxidase, O35 protein

<400> SEQUENCE: 17

Met Ala Ala Thr Val Ser Ser Phe Pro Val Val Asn Met Glu Lys Leu
  1               5                  10                  15

Glu Thr Glu Glu Arg Ala Thr Ala Met Glu Val Ile Arg Asp Gly Cys
             20                  25                  30

Glu Asn Trp Gly Phe Phe Gln Leu Leu Asn His Gly Ile Ser His Glu
         35                  40                  45

Leu Met Asp Glu Val Glu Arg Leu Thr Lys Ala His Tyr Ala Thr Phe
     50                  55                  60

Arg Glu Ala Lys Phe Gln Glu Phe Ala Ala Arg Thr Leu Glu Ala Gly
 65                  70                  75                  80

Glu Lys Gly Ala Asp Val Lys Asp Val Asp Trp Glu Ser Thr Phe Phe
                 85                  90                  95

Val Arg His Leu Pro Ala Ser Asn Leu Ala Asp Leu Pro Asp Val Asp
            100                 105                 110

Asp Arg Tyr Arg Gln Val Met Glu Gln Phe Ala Ser Glu Ile Arg Lys
        115                 120                 125

Leu Ser Glu Arg Leu Leu Asp Leu Leu Cys Glu Asn Leu Gly Leu Glu
    130                 135                 140

Pro Gly Tyr Leu Lys Ala Ala Phe Ala Gly Ser Asp Gly Pro Thr Phe
```

```
                145                 150                 155                 160
Gly Thr Lys Val Ser Ala Tyr Pro Pro Cys Pro Arg Pro Asp Leu Val
                    165                 170                 175

Asp Gly Leu Arg Ala His Thr Asp Ala Gly Gly Ile Val Leu Leu Phe
                180                 185                 190

Gln Asp Asp Gln Val Ser Gly Leu Gln Leu Leu Arg Gly Gly Glu Trp
            195                 200                 205

Val Asp Val Pro Pro Met Arg His Ala Ile Val Ala Asn Val Gly Asp
        210                 215                 220

Gln Leu Glu Val Ile Thr Asn Gly Arg Tyr Lys Ser Val Met His Arg
225                 230                 235                 240

Val Leu Thr Arg Pro Asp Gly Asn Arg Met Ser Val Ala Ser Phe Tyr
                245                 250                 255

Asn Pro Gly Ala Asp Ala Val Ile Phe Pro Ala Pro Ala Leu Val Gly
                260                 265                 270

Ala Ala Glu Glu Asp Arg Ala Glu Ala Tyr Pro Ser Phe Val Phe
            275                 280                 285

Glu Asp Tyr Met Asn Leu Tyr Val Arg His Lys Phe Glu Ala Lys Glu
        290                 295                 300

Pro Arg Phe Glu Ala Met Lys Ser Ala Ile Ala Thr Ala
305                 310                 315

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O35 (ZmACO35) forward primer

<400> SEQUENCE: 18
ctcatcctgc tgctccagga cgac                                              24

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:Zea mays
      (B73) 1-aminocyclopropane-1-carboxylate (ACC) oxidase,
      O35 (ZmACO35) reverse primer

<400> SEQUENCE: 19
acacacataa ctgtgccact ataagca                                           27

<210> SEQ ID NO 20
<211> LENGTH: 7685
<212> TYPE: DNA
<213> ORGANISM: Zea mays
<220> FEATURE:
<223> OTHER INFORMATION: Zea mays ethylene receptor (ethylene response
      sensor receptor, ERS1-like), ERS14 genomic DNA

<400> SEQUENCE: 20
ttttacaaat cgttttgaat aagaattcgg atcaacacct gatattgaag ggggacgaac        60
ttgagtgatt tgactgcatg ctcgacccct tttgatgtac tgaactcctg caatatgtct      120
aaaataccaa ggtaaagaac aacatcgtac tcctcaatgg tatccgggtt ttcaagttcc      180
gtgttcatgt cctcatgcac tttccgagct tgagctggca tattcacccc caactgtaca      240
cggaacctga agcacaata cagaatacac atgaatcggc aacaaaatcc atctagattt      300
```

```
ttttagcaag actgagaaaa ctactctcca acaaatttct atttcaattc catcatttgg      360
gaatgggcaa acattctaat catatggaaa tattcgtgcg agtattgtcc atcaatccag      420
tggtggaaga acataaaaac agtaagagta tgatagtgat tccaatgcaa gtgtataaaa      480
tagacaaacg tataaaaatt tcaatattgt agaagtgaga ttttaaaaat cgttggataa      540
attcaacaaa tatatatcta atattttagc cgcttaaaaa aactttctac aatctcactt      600
ctacaaaaaa tattattaag agtatgtttt tttaattatt attaagagta tggttcaaaa      660
tgaaaattca cttttttttag agtatggttc aaaacgatcc ttttaggtta agtttgaata     720
agacgtgccg gacttaaaat atattatata ctaaacagta ttatagtaaa attaataata     780
attatatttt tttgagatga gtcgatcaaa cttaagatta aaaaattaaa ggaaattaaa     840
aattgaaaca tagggagtat taatttataa actgttggaa agactccaat gagtaatgtc     900
ccatcagata gaggacacc ccctgtcatc tttttggcct accttcgtcg tatctccaag      960
agtctaaatt ttatttttaa aattattatc taaagaatga tttatataaa aacatttat     1020
atattttttc taatctccaa caaattttta tatcttattt gagccattaa tgtttcctat    1080
ctttgactaa caagaaacac ataatagatg atgactatat ttagataatc gtttaaataa    1140
gttgttggag tattttttt ataaaaaatc tctactcata tgaattagaa aaactttgga     1200
gttgcttatg acttttcatg ccttgtctgt agccgcatga tgcagataca atacagtatg    1260
gacacagtgc ttaactaccc cgtatgacca tatcactgca gaagatagcg ttcagatcaa    1320
gacagaaaac aagcaagacg atcttaacca aacagccgtc cactgccttt tctttctccc    1380
gttcaccccg ccgtgcacgc tcttttttgtc cctcgtgccg acgaccgacc gaccgccgcc    1440
gcctcaaggt cttcgtaaag ccactcgccg gcaacgagca gccaccaggt atgccagcac    1500
cttctcttcc attcctgctg tacgaaaccg agcacgcaaa ccctaactta agctaattgg    1560
gtatttgtat tcggatctca tctaattaca ggtgtttaca tgtattatgc ctactaacta    1620
acgctgattt tcgttaaaaa gttatcgggt gtacatgtgt acatccatttt cctttactag   1680
ggccgtttgg aattgcaaat gggagttgga gcggcgaatg acatgtggca tgtcttgtgg    1740
gatttgcatg ctctgccagt acgcgtgctg cgttcatgag cttatgctat tcaaatgcca    1800
tttgctacgc atttatggct atttgggatc gggaactggc gtggcaaaaa cattttatcg    1860
atatgtttct tcttctgcag gaagatgttg tgaggactga tgcaataact aagcttgctg    1920
gatggacgga tgcgattgca tagagccact atggcctacc gatgatcttc tcgtcaagta    1980
tcagtacatc tcagacttct tcatagccct tgcgtacttc tcgattccat ggagctcat     2040
atattttgtg aagaagtcgt ccttcttccc atacagatgg gtcctgatcc agtttggtgc    2100
gtttatagtt ctttgtgggg caacccatct gataaacctg tggacgttca ccacacatac    2160
aaagaccgtt gcgatggtca tgaccatagc gaagatttct acagcagtcg tgtcctgtgc    2220
aactgctttg atgctcgttc atatcattcc cgacttgttg agcgtgaaaa ctagggagtt    2280
gttcttgaag aataaagctg aggagcttga tagagagatg ggacttataa ggacgcaaga    2340
ggagactggt agacatgtta ggatgcttac acatgaaatc agaagtactc ttgatagaca    2400
tacaattttg aagactactc tcgttgagct aggaaggacc ttgggtctgg aagaatgtgc    2460
attgtggatg ccatctcgaa gtggctcaag ccttcagctt tctcatactt tgcgccacca    2520
gattactgtt ggatcatcgg tgccaatgaa tcttcctgtc gtcaatcaag tgttcagtag    2580
caaccgggca atcataatac cccacacatc ttctttggcg cggttcgac ctcttgcagg     2640
gcgatatgtt ccaccagaag tggccgcagt ccgtgtacct cttctacatc tttcaaactt    2700
```

```
tcaaataaat gattggcctg agctctcagc aaaaagcttt gcaatcatgg ttttgatgct    2760
tccatctgat agtgctagaa aattgcatgt gcatgaattg gagctggttg aggtcgttgc    2820
tgatcaggtt cgtgctgtat cttttgctat ggttactata acatactact tccatccaga    2880
gaaggatgta aatttacttc tgtctctatt caattcaagc tatctatact tttactaagt    2940
ttattaaaaa tattatcaat atatatatca tcggataggt gtattttgaa aatatgttcc    3000
atgacaaatc taacaacact tatttgacag tgttttttag ttttagtaa atttagtcac     3060 ggtttgactc ggtactatgc tagaattaca ttcttttccg gatggagtat atgcttgtag    3120
gagaggaaaa acatgtttac atctttcaaa atcatatgat actgctcagt gatcatgatc    3180
aattaaggca tccgttaatt gaataggaaa gtatattcac aggtgcaatg caatgatgac    3240
aagactacct tcaaatcaat acataagttc ttttttgaaa gcattggatt ctgaacccaa    3300
ctacccaaat gcaaaagaca tgtgctcttg cttgttttgc gatatctaca cctttctgaa    3360
agataaaagt ttaaatgggt attgctagca gatctattgt ttatctttt ttgtttcttc     3420 accaggtagc agttgcacta tctcatgcag ctattctcga agagtccatg cgggcacgtg    3480
atttactaat ggagcagaat gttgccctgg atttagctcg aagagaggct gagatggcta    3540
tccgtgctcg caatgatttc ctagctgtta tgaatcacga aatgagaaca cccatgaatg    3600
caataatagc cctttcctcc ttgcttttgg aaactgagct tactcctgag cagcgtctaa    3660
tggtggaaac agtactgaaa agcagcaatt tgttagcaac actcatcaat gatgttctgg    3720
atctttccaa actcgaggat ggaagccttg aactggagat taaagcattc aatcttcatg    3780
ctgttttcaa agaagtatgc accacagcta atactctttc tgctccagat tataggtcac    3840
tttagctttg ctccaagtca aactctaact ttgaccatgt ttttaaaaa aaatatctta    3900 acttccacaa aatcaaataa atgcacaaac aagacatttc atggaggatt aatgaaactg    3960
attgacatta ttgttagtgt atatttctat aagtttgtcc aaagttagaa cttaggtaaa    4020
ggaagtgacc tataattggt aatagaggga gtatcaaaca tctagataca tgatgcaata    4080
gctctaattc ttatttggta ttacaggtga tgggtttcat taaaccaatt gcatctatca    4140
agaggctatc tgtatcggtt atgttggcac cagatctgcc gttatgtgca attggtgatg    4200
aaaagagact catgcaaact attctgaaca tctctggcaa tgctgtaaag tttaccaagg    4260
agggacacat cacgcttgta gcttccattg tgaaggctga ctctttgaga gagttcagaa    4320
ccccagaatt tcatccaact gcaagtgatg aacatttcta tttgaaagtt caggtgatat    4380
tctagaagag gcttgtttga ataattttcc ttgagcttgt caatgagctc atgatctttc    4440
catagtatca ataaaacaag aagatttatc tgcaaatagt tgtatgcact gttccctctt    4500
taataacaat aataacttaa aagatgacct gcatgcgttg tgcagagctc caaaattcaa    4560
aaatgaaact ggagccatcc atttggttgt cccaagtagc agttttgtaa aaccgaattg    4620
cagcctgtcg aaaaatctca actctttcat tgtacaacat ttgtaatctg ttgtcttatc    4680
tccttatgtg tgactgaatt tctcatgcac tctggttttg gatccatcca ctatgttcct    4740
cataatgaag tatttcatgc ttatttagta gcaaagaca atattttttc ttgaaaatcc     4800
tcttaattaa cacgtgcatt ttcttgtatg aatcgttacc tattccttt aatcatgtat     4860 cttggtaatt aattgcattt gcatcattaa acctggctcg actcttgtgt tgcttgatag    4920
ttcatttgtc ttgtctataa actaggtggg tctcagctct gtataggtcc atgtacaatt    4980
ttccaattct tccatcaag tttacaaaaa caggtgggc ctgtccagct gtacctgact       5040
atgatttggg gtgggtgggg tctgaatctt ttacttat cttataatct catggtgtag       5100
```

```
aatttctgct ggttgggcct gatgacattt ggaatctgat tacttcttta caccattgtg   5160
acattagttg actgtcattc actgctttt atttgagttg cctggattga attagtctca   5220
ggactgacat aggataggac ctaatatcgc attagcaaaa gctaaaatgg tctaggatta   5280
gaagtgctat accaaatctt ccatgaactc cagatagccc agagtctttt ataatgccac   5340
acacagagct ttggtatgtt gaaaaaaatc ataggtcaac cgaactaagt tatcacaaca   5400
tttactcaaa ctatatcaga attcagaagg tacagatgct tacataaatt tcattttagt   5460
tgataccacc ggtcctgggt ttcatgctta caactagaaa agggttctat tttttcagat   5520
tatgaacata ccatggaaac atgaagcagg tttttacttt tatatatgct agcaattgtt   5580
atctgttgtg ttgctttaca tttctgttac ttactctttt gcaggtaaaa gatacaggct   5640
gtggagttag tcctcaggat ctacctcatg tattcacaaa gtttgctcat cctcaaagtg   5700
gaggaaaccg agggtttaat ggtagtggtc ttggccttgc catatgcaag aggtagtttg   5760
accttacagc tcctttcttg tagttccttc tgaaaattgt gttctggtgt tttttgtgac   5820
tcttgacttt ctcctacgca gcacatttat ttatttattt tatgcattgc cagtacatgg   5880
ctcattagtg ctaacctggt catcaattct tattagaact catcagcatc tctgcaaaat   5940
tctgcgcagg tttgttagtc ttatgggagg gcacatctgg atcgacagcg aaggaaccgg   6000
aagaggttgc accgcaacat tcgtcatcaa gctcggcgtg tgtgacaaca caaacaccta   6060
ccaaaagcag ctggttcctc taatctggcc aagcagtgca gactccaatt tgtctgctcc   6120
gaaagtgctg cccgacggga gaggatctgt ttccctgaaa tctcggtacc aaagaagcgt   6180
atgagctcag tgtaaatgat tgacggcata gtgccaagta ggggatcgat tagtgccatt   6240
gtctaatttt gtttgtaacc cagtcatagc aacatatagt gtacaaataa tgtaaagcca   6300
atggagactg cagctgtgta tctgggtagc aacgctgact tgctgcattg agtagtatgt   6360
cctaccagcg gattgaattg cttgttctgg ggtgtgcggc gcgcgccccg ttgattgttc   6420
tgttgtaact tgtaatccca tattaatcgt gtaatatgaa attcaatgca aatacacggt   6480
cacaagctgt tttcggtgcc ctcgctccat cagttggttc agatcgtaga tgctgccagt   6540
tgcatgtgtt agataggact ggaaaataag ctcgaggctt gcgagccggc tcgagctcga   6600
agtgtttcgc gagcctcgaa cgagtcgagc tccttctttg agctcgtttt tatagtgagc   6660
cgagccgtct cgttccagct cgcgagcctt acaaaaataa ttaatttata gaataataat   6720
gaatattaga taattttatg gataaatagct cattttttag ttttttgatga tgaatatatt   6780 ataatttata atttaaatta ctcataatgt tgaatgattc tttgatgatg aatatattac   6840
aatttataat ttaaattact cataatgttg aatgatgatt atatatttca aatttatata   6900
atattaattc actaaatagt gcaacaataa ataccataat atggctcgtg agccgagccg   6960
gctcgcgagc caatattgag cagagcagcc tctttcgcta gctcgtggaa tagacaagcc   7020
gagctcgttt aggcaacctc ggctcgtttt cagcccctagt cttagagttg tttggaacct   7080
ctatagctaa taattagttg ctaaaattag cttgggaggt tctaaacacc cacctctgct   7140
cggctcgttc aggcaaggtc aactcggctc gtccagtcct taattttcaa cactcaagta   7200
taattttaga tcactgaatt tgctatttta ttttcttcat atattatttt tattattatt   7260
ttattttttt ttcttataca cattttgggc cttaaatatt attagcacac tgatttcttg   7320
tctatctata tcttttttgga cattttaagc tgcaactagt aaacgggcat cccctgtacg   7380
tatggtatgg gttaggacga ccctgcttcg cttcagcgtg agtgtggcgc caattttgca   7440
tcagcgtttg ctatcatcgt cacgacgaga atgtacggtg aatatacaaa gcacaacaca   7500
```

| | |
|---|---:|
| acaattgtgt atatatagaa taatgagaaa aggcaacctc aacatacgat gcggacgaga | 7560 |
| aaagagcaat tgatgataga ctgataccca ccaccagtac cacagtccac gctccttttc | 7620 |
| ttttcttttt tccctccttt gtattgcaca aatcagtgag cgtgcagtcg ataaagacac | 7680 |
| acttt | 7685 |

<210> SEQ ID NO 21
<211> LENGTH: 1902
<212> TYPE: DNA
<213> ORGANISM: Zea mays
<220> FEATURE:
<223> OTHER INFORMATION: Zea mays ethylene receptor (ethylene response
sensor receptor, ERS1-like), ERS14 coding sequence
(CDS)

<400> SEQUENCE: 21

| | |
|---|---:|
| atggacggat gcgattgcat agagccacta tggcctaccg atgatcttct cgtcaagtat | 60 |
| cagtacatct cagacttctt catagccctt gcgtacttct cgattccatt ggagctcata | 120 |
| tattttgtga agaagtcgtc cttcttccca tacagatggg tcctgatcca gtttggtgcg | 180 |
| tttatagttc tttgtggggc aacccatctg ataaacctgt ggacgttcac cacacataca | 240 |
| aagaccgttg cgatggtcat gaccatagcg aagatttcta cagcagtcgt gtcctgtgca | 300 |
| actgctttga tgctcgttca tatcattccc gacttgttga gcgtgaaaac tagggagttg | 360 |
| ttcttgaaga ataaagctga ggagcttgat agagagatgg gacttataag gacgcaagag | 420 |
| gagactggta gacatgttag gatgcttaca catgaaatca gaagtactct tgatagacat | 480 |
| acaattttga agactactct cgttgagcta ggaaggacct tgggtctgga agaatgtgca | 540 |
| ttgtggatgc catctcgaag tggctcaagc cttcagcttt ctcatacttt gcgccaccag | 600 |
| attactgttg gatcatcggt gccaatgaat cttcctgtcg tcaatcaagt gttcagtagc | 660 |
| aaccgggcaa tcataatacc ccacacatct tctttggcgc gggttcgacc tcttgcaggg | 720 |
| cgatatgttc caccagaagt ggccgcagtc cgtgtacctc ttctacatct ttcaaacttt | 780 |
| caaataaatg attggcctga gctctcagca aaaagctttg caatcatggt tttgatgctt | 840 |
| ccatctgata gtgctagaaa attgcatgtg catgaattgg agctggttga ggtcgttgct | 900 |
| gatcaggtag cagttgcact atctcatgca gctattctcg aagagtccat gcgggcacgt | 960 |
| gatttactaa tggagcagaa tgttgccctg gatttagctc gaagagaggc tgagatggct | 1020 |
| atccgtgctc gcaatgattt cctagctgtt atgaatcacg aaatgagaac acccatgaat | 1080 |
| gcaataatag ccctttcctc cttgcttttg gaaactgagc ttactcctga gcagcgtcta | 1140 |
| atggtggaaa cagtactgaa aagcagcaat ttgttagcaa cactcatcaa tgatgttctg | 1200 |
| gatctttcca aactcgagga tggaagcctt gaactggaga ttaaagcatt caatcttcat | 1260 |
| gctgttttca aagaagtaat gggtttcatt aaaccaattg catctatcaa gaggctatct | 1320 |
| gtatcggtta tgttggcacc agatctgccg ttatgtgcaa ttggtgatga aaagagactc | 1380 |
| atgcaaacta ttctgaacat ctctggcaat gctgtaaagt ttaccaagga gggcacacatc | 1440 |
| acgcttgtag cttccattgt gaaggctgac tctttgagag agttcagaac cccagaattt | 1500 |
| catccaactg caagtgatga acatttctat ttgaaagttc aggtaaaaga tacaggctgt | 1560 |
| ggagttagtc ctcaggatct acctcatgta ttcacaaagt ttgctcatcc tcaaagtgga | 1620 |
| ggaaaccgag ggtttaatgg tagtggtctt ggccttgcca tatgcaagag gtttgttagt | 1680 |
| cttatgggag gcacatctg gatcgacagc gaaggaaccg gaagaggttg caccgcaaca | 1740 |
| ttcgtcatca agctcggcgt gtgtgacaac acaaacacct accaaaagca gctggttcct | 1800 |

```
ctaatctggc caagcagtgc agactccaat ttgtctgctc cgaaagtgct gcccgacggg    1860
agaggatctg tttccctgaa atctcggtac caaagaagcg ta                        1902
```

<210> SEQ ID NO 22
<211> LENGTH: 634
<212> TYPE: PRT
<213> ORGANISM: Zea mays
<220> FEATURE:
<223> OTHER INFORMATION: Zea mays ethylene receptor (ethylene response
      sensor receptor, ERS1-like), ERS14 protein

<400> SEQUENCE: 22

```
Met Asp Gly Cys Asp Cys Ile Glu Pro Leu Trp Pro Thr Asp Asp Leu
 1               5                  10                  15

Leu Val Lys Tyr Gln Tyr Ile Ser Asp Phe Phe Ile Ala Leu Ala Tyr
             20                  25                  30

Phe Ser Ile Pro Leu Glu Leu Ile Tyr Phe Val Lys Lys Ser Ser Phe
         35                  40                  45

Phe Pro Tyr Arg Trp Val Leu Ile Gln Phe Gly Ala Phe Ile Val Leu
     50                  55                  60

Cys Gly Ala Thr His Leu Ile Asn Leu Trp Thr Phe Thr His Thr
 65                  70                  75                  80

Lys Thr Val Ala Met Val Met Thr Ile Ala Lys Ile Ser Thr Ala Val
             85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Glu Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Gly Leu
                165                 170                 175

Glu Glu Cys Ala Leu Trp Met Pro Ser Arg Ser Gly Ser Ser Leu Gln
            180                 185                 190

Leu Ser His Thr Leu Arg His Gln Ile Thr Val Gly Ser Ser Val Pro
        195                 200                 205

Met Asn Leu Pro Val Val Asn Gln Val Phe Ser Ser Asn Arg Ala Ile
    210                 215                 220

Ile Ile Pro His Thr Ser Ser Leu Ala Arg Val Arg Pro Leu Ala Gly
225                 230                 235                 240

Arg Tyr Val Pro Pro Glu Val Ala Val Arg Val Pro Leu Leu His
                245                 250                 255

Leu Ser Asn Phe Gln Ile Asn Asp Trp Pro Glu Leu Ser Ala Lys Ser
            260                 265                 270

Phe Ala Ile Met Val Leu Met Leu Pro Ser Asp Ser Ala Arg Lys Leu
        275                 280                 285

His Val His Glu Leu Glu Leu Val Val Val Ala Asp Gln Val Ala
    290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Met Ala Ile Arg Ala Arg Asn Asp Phe Leu Ala Val Met Asn
```

```
                340             345             350
His Glu Met Arg Thr Pro Met Asn Ala Ile Ile Ala Leu Ser Ser Leu
            355                 360                 365
Leu Leu Glu Thr Glu Leu Thr Pro Glu Gln Arg Leu Met Val Glu Thr
        370                 375                 380
Val Leu Lys Ser Ser Asn Leu Leu Ala Thr Leu Ile Asn Asp Val Leu
385                 390                 395                 400
Asp Leu Ser Lys Leu Glu Asp Gly Ser Leu Leu Glu Ile Lys Ala
                405                 410                 415
Phe Asn Leu His Ala Val Phe Lys Glu Val Met Gly Phe Ile Lys Pro
            420                 425                 430
Ile Ala Ser Ile Lys Arg Leu Ser Val Ser Val Met Leu Ala Pro Asp
            435                 440                 445
Leu Pro Leu Cys Ala Ile Gly Asp Glu Lys Arg Leu Met Gln Thr Ile
        450                 455                 460
Leu Asn Ile Ser Gly Asn Ala Val Lys Phe Thr Lys Glu Gly His Ile
465                 470                 475                 480
Thr Leu Val Ala Ser Ile Val Lys Ala Asp Ser Leu Arg Glu Phe Arg
                485                 490                 495
Thr Pro Glu Phe His Pro Thr Ala Ser Asp Glu His Phe Tyr Leu Lys
            500                 505                 510
Val Gln Val Lys Asp Thr Gly Cys Gly Val Ser Pro Gln Asp Leu Pro
            515                 520                 525
His Val Phe Thr Lys Phe Ala His Pro Gln Ser Gly Gly Asn Arg Gly
        530                 535                 540
Phe Asn Gly Ser Gly Leu Gly Leu Ala Ile Cys Lys Arg Phe Val Ser
545                 550                 555                 560
Leu Met Gly Gly His Ile Trp Ile Asp Ser Glu Gly Thr Gly Arg Gly
                565                 570                 575
Cys Thr Ala Thr Phe Val Ile Lys Leu Gly Val Cys Asn Thr Asn
            580                 585                 590
Thr Tyr Gln Lys Gln Leu Val Pro Leu Ile Trp Pro Ser Ser Ala Asp
            595                 600                 605
Ser Asn Leu Ser Ala Pro Lys Val Leu Pro Asp Gly Arg Gly Ser Val
        610                 615                 620
Ser Leu Lys Ser Arg Tyr Gln Arg Ser Val
625                 630

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:Zea mays
      ethylene receptor (ethylene response sensor
      receptor, ERS1-like, ZmERS14) forward primer

<400> SEQUENCE: 23
gagttagtcc tcaggatcta cctcatgt                                       28

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:Zea mays
      ethylene receptor (ethylene response sensor
      receptor, ERS1-like, ZmERS14) reverse primer
```

```
<400> SEQUENCE: 24
caactcaatc cgctggtagg acatact                                          27

<210> SEQ ID NO 25
<211> LENGTH: 6378
<212> TYPE: DNA
<213> ORGANISM: Zea mays
<220> FEATURE:
<223> OTHER INFORMATION: Zea mays ethylene receptor (ethylene response
      sensor receptor, ERS1-like), ERS25 genomic DNA

<400> SEQUENCE: 25
gacgccgagt tcgatgtgga catccatcgc tcggtggacg accacgatat ccatagcgtg      60
ctggactacc gccgtctgcg cgaggccatc gtcgaggaat gcacgcaggc gcatgtgaac     120
ctgatcgaaa ccctgtccga acaagtcgcc gcgcgcctgt tggccgactt ccaggaaatc     180
cgctcgttgc gcttgcgcat cagcaagccc atggcctttt ccgactgcgc ggcggtaggc     240
gtggaaatcc agatcacccg ctgaccatga acgatattgc tccgcccccc gccgtccgct     300
cccccgaggt ccgctatcgc accgaggccg aggaaaaggc ccgccacgaa ggcaacaagc     360
tgaccaagcg cctggcccgc gaaaccacgc gcgcgctgtc cgactacaac atgattgaag     420
aaggcgaccg cgtgatggtc tgcctgtcgg gcggcaagga ttcctatgcc atgctggaca     480
tcctgctgca attgcagaag cgcgcgccgt caagtttga actgatcgcc gtcaacctgg      540
accagaagca gccgggcttt cccgaccaca tcctgcccca gtacctgaaa gacctgggcg     600
tgcccttcca catcgagacg caggacacgt attccatcgt cacgcgcgtg ctggaagaag     660
gcaagacgat gtgctcgctc tgttcgcgct tgcgtcgcgg cattctgtac cgcgtcgcct     720
cggaactggg cgccaccaag atcgcgctgg gccaccaccg cgacgacatc ctggccacgt     780
tcttcctgaa cctgttctat ggcggcaagg ccaagggcat gccgcccaaa ctggtgtcgg     840
acgacggccg ccacaccgtg atccgtccgc tggcctatgt ggccgaaacg gacctgatcg     900
cctatgcgga gttgaagcaa ttccccatca ttccgtgcaa cctctgcggc tcgcaggaaa     960
acctgaagcg caaggaagtg ggccggatga tctatatata gtcttagggt tgtcatgcga    1020
cctagcaaat aaagaggatg actctggtca ggaacggata taaagcatcg ggccacctcg    1080
ttcgtggctt aatccatatt ttttatttta tatttgttat ctttagacta aaatgtattg    1140 gactttttt tgcttgatcg gatgggattt ttttcatgt cgtggttgtg gtcgcatgaa      1200
gtcatgaaga tgcttgctgg catgttgctg ttgggtagcc catctctgca tgccattgcc    1260
cactcttaca gaactgtagt aacaacagca gctggtgtag agtagctgca gtgagccagt    1320
gaacgcaatg cttagacgac ttacagaaca gcgccggact gccttcaccc tgcctattct    1380
ttcttcccgt tcaccccgcg tgcacgctct ttcccttcct cgtgccgacg accgggcgac    1440
cgccgcgccc cggccgcgc ccccttgtct cgggccactc gccggcaacg agcagccacc     1500
aggtatgcca cccccttctc ccccccttcct gctgtacgaa accgagcacc caaaccctaa   1560
cttaagctta tttggctatt tacattcgga tctgatctag ttacaggagc acacacgtat    1620
tatccctact aaatccgatt ttagtggaaa aagctgtcgg gtgtacatgt gtccacccat    1680
gtcctttacg agttcggccc ttggccgagg tccgtttgga attggaaatg ggaatcagag    1740
gggcgaatgc cgaatgggca tgtcttgcgc aatttccatg ctctgctagt aggcgtgctg    1800
cgttcatgag ctcatactat ccaaatgcca ttcgctacgc atttgcttct atttgagatc    1860
gggaaacggt gtgtcaaaaa cgatttatca atatgttttct tcttctacag gaaatgttgt   1920
gaggactgat gcaataacta agcttgctgg atggacggat gtgattgcat cgagccacta    1980
```

```
tggcctaccg atgatctcct tgtcaagtat cagtacatct cagacttctt catagccctc    2040
gcgtacttct ctattccgtt ggagctcata tatttcgtga agaagtcgtc cttcttcccg    2100
tacagatggg tcttgatcca gtttggtgcg tttatagttc tctgtggggc aacccatctg    2160
ataaacctgt ggacgttcac cacacataca aagaccgttg cgatggtcat gaccatagca    2220
aaggtttcta cagcagttgt gtcctgtgca actgctttga tgcttgttca tatcatcccc    2280
gacttattga gcgtgaaaac tagagagttg ttcctgaaga ataaagctga agagcttgac    2340
agagagatgg gactgataag gacgcaggag gagaccggta gacatgttag gatgcttaca    2400
catgaaatca gaagtactct tgacaggcat atgattttga agactactct tgttgagcta    2460
ggaaggacct tgggtctgga ggaatgtgca ttgtggatgc catctcgaag tggttcaagc    2520
cttcagcttt ctcatacttt gcaccaccag attactgttg gatcatcggt gccaattaat    2580
cttcctgtca tcaatcaagt gttcagtagc aaccgggcaa ttataatacc ccacacatct    2640
cctttggcgc ggattcgacc tcttacaggg cgatatgttc caccagaagt ggctgcagtc    2700
cgtgtacctc ttctccacct ttcaaacttc caaataaatg attggcctga gctttcggca    2760
aaaagctttg caatcatggt tttgatgctt ccatctgata gtgcaagaaa atggcatgta    2820
catgaattgg agctggttga ggttgttgct gatcaggttc gtgctgtatc tctgtctatg    2880
gttactataa catggtacct tcatcctgaa aatgatgtaa atttacttgt ctctattcaa    2940
acaatctata ctttgattaa gttattaaaa agattatcaa taaatatgac atcagatagg    3000
tatattttga aaatatattc catgacatat ttaacaatac ttatttgata gtgtaaatat    3060
tgctattttt aaataaattt ggtcactgtt ttacttggcg ctatgctaga attacattct    3120
tttctggatg gagggagtat atgcttgtag gagaggaaaa acatgtttac atctttcaaa    3180
ttcatatgat actgctcagt tatcatgatc agtcaattaa ggcatccgtt aattgaacag    3240
gaaagtatat tcacaggtgc aatgtaatga tgacaagaat acctttaaat caatacataa    3300
tctctttttt tgaaagcata ggattctgaa cccaactacc gagccacaaa agacacatgc    3360
tcttgctgtt gcgcaatatc tacaccttc tgaaggttaa aagtttaaat tggtagtgct    3420
agcaggtcta ttgtttatct cctttttttg tttcttcatc aggtagcagt tgcactatct    3480
catgcggcta ttcttgaaga gtccatgcga gcacgtgatt tactaatgga gcagaatgtt    3540
gccctggatt tagctcgaag agaggctgag atggctatcc gtgctcgcaa tgattttcta    3600
gctgttatga atcacgaaat gagaacaccc atgaatgcaa taatagccct ttcctccttg    3660
cttttggaaa ctgagcttac tcctgagcag cgtctaatgg tggaaacagt actgaaaagc    3720
agcaatctgt tagcaacact catcaatgat gtgctagatc tttccaaact cgaggatgga    3780
agccttgaac tggagattaa agcattcaat cttcatgctg ttttcaaaga agtatgcacc    3840
atcagttttc taatactctt tccgttccag gttctaggtt actttagctt tgctctaagt    3900
caaactctaa ctttggccaa gttttttagaa aaatatgtca acttctacaa attaaaataa    3960
atgcactaac aagacatgtt atggagaatt catgtgatgt tattgttggt gtattttcct    4020
ataagtttgt tcaaagttag agaaattgga cttaggtaaa gaaagcgact tgtaattagt    4080
aacagaggga gtatcaaaca tctagataca cggtgcaaca actaaaattc ctatttggta    4140
ttacaggtga tgggtttcat taaccaatt gcatctatca agaggctatc tgtatcggtt    4200
atgttggcac cagatttgcc gttatgtgcc attggtgatg aaaagagact catgcaaact    4260
attctgaaca tctctggcaa cgctgtaaag tttaccaagg agggacacat cacacttgta    4320
gcttccattg tgaaggctga ctctttgaga gagttcagaa ccccagaatt tcatccaact    4380
```

-continued

```
gcaagtgatg accatttcta tttgaaagtt caggtaatat tctagaaagg cttgtttgaa    4440
taatcttgga cttgtcaatg agctcatggt ctttccatac tatcaataaa acaaatagaa    4500
ttttttgcaa atggttgtat gcattgtccc tctttaataa caataataac ttaaaaaatg    4560
acctgtatgt gttgtgcaga gcaccaaatt tcaaaaatga aactggagcc atccatttgg    4620
ttgtctcaag tagcagttta gtgaaccctá attgcagctt gtcaaacaat ctcaactatt    4680
tcattgtaca acatttataa tctgttgtct tgtcttctta tttgcgactg aatttctcat    4740
gcactctggt tctggattca ctgtgttcct cacattgaag tatttcatgc ttattcagta    4800
gtagatgata ttttttttcat gaaaatcctc ttgattaata tctgcgtttc cttgtatgat    4860
ttgttacata tttcctttaa ttatgcgtct tggtcattaa ttgcatatgc atcataactt    4920
ggatagaccc ttaagttgtt tgatagtcca tttgtttata aactatgtgg tcgtcagctc    4980
tgtataggtc catgtacaat tttccaattc tttgtaccaa gtttacaaaa gcagacggta    5040
cctgttcaga tgtacctgac tgatgtgtgt gtgtgtgggg ggggagggg gtctgaatcc    5100
ttttctttgt tataatctca aggagtcaag gtggtgtgga atttctacca gtgttgggca    5160
tgatgatttt tggaatccga tttctttacg ccactgtgac cttagttcag tagtcatttg    5220
ttgcgtttta tctgagttgc ctggattgaa ttagtcgcag gactgacata ggactaggac    5280
ctaaggccgc attagcaaaa actcagatgg tctaggatcc gttgacctgc aggtcgaccc    5340
agatcataag tgttatacca aatcttccat gagctccaga tcagccctga tccttgtata    5400
atgctaacac aaaagctttcg tgtgttgaaa aacattccta ggtcaaccat attaagttat    5460
cacaacgttt actcaatata tcacaaggcg cagatgctta tatttgcaga ttatgaacat    5520
gccatggaca aacgaagcag agttttactt ctatgcttag caagtcttat ctattgtgtt    5580
gctttacatt ctctgttact tcacacttct gcaggtaaaa gatacaggct gtggaattgg    5640
tccacaggat ctacctcatg tatttacaaa gtttgctcat cctcaaagcg gaggaaaccg    5700
agggtttaat ggtagtggtc ttggccttgc catatgcaag aggtagttcg atcttacatc    5760
tcctttctgt agttccttct gaatctggtg ttaaggtgct gtttttggtg actcgaagtc    5820
ttcctatgca gcacaattat ttatttattt tgtttaatgc attgccagta tatagggata    5880
cctcggtcat caattctcat tagaactcat cggcatctct gcaaatttct ggtgcaggtt    5940
tgttagtctc atgggagggc acatctggat tgacagcgaa ggaaccggaa gaggttgcac    6000
cgcaacattc gtcgtcaagc tcggcgtgtg tgacaacaca aacacctacc agcagcagct    6060
gatccctcta gtatggccaa gcagcgcaga ctccgatttg cgtgctccga aacctcttcc    6120
ggacgggaga ggatctactc ccttgaaatc tcggtaccaa aggagcgtat gagcctagtg    6180
taaatgattg acggcatagt gccaagtagg ggaccgatta gtgccaccgt ctaattttgt    6240
ttgtaaccct gtcatagcag gcatatgatg tacaaatact gtaaagcaaa tggagactgc    6300
ggccgtgtat ctgggtggca acgctgactt gctgcattga gtggtatata catatgctac    6360
cagcggattg aattgctt                                                   6378
```

<210> SEQ ID NO 26
<211> LENGTH: 1905
<212> TYPE: DNA
<213> ORGANISM: Zea mays
<220> FEATURE:
<223> OTHER INFORMATION: Zea mays ethylene receptor (ethylene response sensor receptor, ERS1-like), ERS25 coding sequence (CDS)

<400> SEQUENCE: 26

```
atggacggat gtgattgcat cgagccacta tggcctaccg atgatctcct tgtcaagtat      60
cagtacatct cagacttctt catagccctc gcgtacttct ctattccgtt ggagctcata     120
tatttcgtga agaagtcgtc cttcttcccg tacagatggg tcttgatcca gtttggtgcg     180
tttatagttc tctgtggggc aacccatctg ataaacctgt ggacgttcac cacacataca     240
aagaccgttg cgatggtcat gaccatagca aaggtttcta cagcagttgt gtcctgtgca     300
actgctttga tgcttgttca tatcatcccc gacttattga gcgtgaaaac tagagagttg     360
ttcctgaaga ataaagctga agagcttgac agagagatgg gactgataag gacgcaggag     420
gagaccggta gacatgttag gatgcttaca catgaaatca aagtactcct tgacaggcat     480
atgattttga agactactct tgttgagcta ggaaggacct tgggtctgga ggaatgtgca     540
ttgtggatgc catctcgaag tggttcaagc cttcagcttt ctcatacttt gcaccaccag     600
attactgttg gatcatcggt gccaattaat cttcctgtca tcaatcaagt gttcagtagc     660
aaccgggcaa ttataatacc ccacacatct cctttggcgc ggattcgacc tcttacaggg     720
cgatatgttc caccagaagt ggctgcagtc cgtgtacctc ttctccacct ttcaaacttc     780
caaataaatg attggcctga gctttcggca aaaagctttg caatcatggt tttgatgctt     840
ccatctgata gtgcaagaaa atggcatgta catgaattgg agctggttga ggttgttgct     900
gatcaggtag cagttgcact atctcatgcg gctattcttg aagagtccat gcgagcacgt     960
gatttactaa tggagcagaa tgttgccctg gatttagctc aagagaggc tgagatggct    1020
atccgtgctc gcaatgattt tctagctgtt atgaatcacg aaatgagaac acccatgaat    1080
gcaataatag ccctttcctc cttgcttttg gaaactgagc ttactcctga gcagcgtcta    1140
atggtggaaa cagtactgaa aagcagcaat ctgttagcaa cactcatcaa tgatgtgcta    1200
gatctttcca aactcgagga tggaagcctt gaactggaga ttaaagcatt caatcttcat    1260
gctgttttca agaagtaat gggtttcatt aaaccaattg catctatcaa gaggctatct    1320
gtatcggtta tgttggcacc agatttgccg ttatgtgcca ttggtgatga aaagagactc    1380
atgcaaacta ttctgaacat ctctggcaac gctgtaaagt ttaccaagga gggacacatc    1440
acacttgtag cttccattgt gaaggctgac tctttgagag agttcagaac cccagaattt    1500
catccaactg caagtgatga ccatttctat ttgaaagttc aggtagtaaa agatacaggc    1560
tgtggaattg gtccacagga tctacctcat gtatttacaa agtttgctca tcctcaaagc    1620
ggaggaaacc gagggtttaa tggtagtggt cttggccttg ccatatgcaa gaggtttgtt    1680
agtctcatgg gagggcacat ctggattgac agcgaaggaa ccggaagagg ttgcaccgca    1740
acattcgtcg tcaagctcgg cgtgtgtgac aacacaaaca cctaccagca gcagctgatc    1800
cctctagtat ggccaagcag cgcagactcc gatttgcgtg ctccgaaacc tcttccggac    1860
gggagaggat ctactccctt gaaatctcgg taccaaagga gcgta                   1905
```

<210> SEQ ID NO 27
<211> LENGTH: 634
<212> TYPE: PRT
<213> ORGANISM: Zea mays
<220> FEATURE:
<223> OTHER INFORMATION: Zea mays ethylene receptor (ethylene response sensor receptor, ERS1-like), ERS25 protein

<400> SEQUENCE: 27

Met Asp Gly Cys Asp Cys Ile Glu Pro Leu Trp Pro Thr Asp Asp Leu
 1               5                  10                  15

Leu Val Lys Tyr Gln Tyr Ile Ser Asp Phe Phe Ile Ala Leu Ala Tyr

```
                20                  25                  30
Phe Ser Ile Pro Leu Glu Leu Ile Tyr Phe Val Lys Lys Ser Ser Phe
            35                  40                  45

Phe Pro Tyr Arg Trp Val Leu Ile Gln Phe Gly Ala Phe Ile Val Leu
            50                  55                  60

Cys Gly Ala Thr His Leu Ile Asn Leu Trp Thr Phe Thr Thr His Thr
65                  70                  75                  80

Lys Thr Val Ala Met Val Met Thr Ile Ala Lys Val Ser Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Glu Glu
            115                 120                 125

Leu Asp Arg Glu Met Gly Leu Ile Arg Thr Gln Glu Glu Thr Gly Arg
            130                 135                 140

His Val Arg Met Leu Thr His Glu Ile Arg Ser Thr Leu Asp Arg His
145                 150                 155                 160

Met Ile Leu Lys Thr Thr Leu Val Glu Leu Gly Arg Thr Leu Gly Leu
                165                 170                 175

Glu Glu Cys Ala Leu Trp Met Pro Ser Arg Gly Ser Ser Leu Gln
            180                 185                 190

Leu Ser His Thr Leu His His Gln Ile Thr Val Gly Ser Ser Val Pro
            195                 200                 205

Ile Asn Leu Pro Val Ile Asn Gln Val Phe Ser Ser Asn Arg Ala Ile
            210                 215                 220

Ile Ile Pro His Thr Ser Pro Leu Ala Arg Ile Arg Pro Leu Thr Gly
225                 230                 235                 240

Arg Tyr Val Pro Pro Glu Val Ala Ala Val Arg Val Pro Leu Leu His
                245                 250                 255

Leu Ser Asn Phe Gln Ile Asn Asp Trp Pro Glu Leu Ser Ala Lys Ser
            260                 265                 270

Phe Ala Ile Met Val Leu Met Leu Pro Ser Asp Ser Ala Arg Lys Trp
            275                 280                 285

His Val His Glu Leu Glu Leu Val Glu Val Ala Asp Gln Val Ala
            290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Met Ala Ile Arg Ala Arg Asn Asp Phe Leu Ala Val Met Asn
            340                 345                 350

His Glu Met Arg Thr Pro Met Asn Ala Ile Ile Ala Leu Ser Ser Leu
            355                 360                 365

Leu Leu Glu Thr Glu Leu Thr Pro Glu Gln Arg Leu Met Val Glu Thr
            370                 375                 380

Val Leu Lys Ser Ser Asn Leu Leu Ala Thr Leu Ile Asn Asp Val Leu
385                 390                 395                 400

Asp Leu Ser Lys Leu Glu Asp Gly Ser Leu Glu Leu Glu Ile Lys Ala
                405                 410                 415

Phe Asn Leu His Ala Val Phe Lys Glu Val Met Gly Phe Ile Lys Pro
            420                 425                 430

Ile Ala Ser Ile Lys Arg Leu Ser Val Ser Val Met Leu Ala Pro Asp
            435                 440                 445
```

```
Leu Pro Leu Cys Ala Ile Gly Asp Glu Lys Arg Leu Met Gln Thr Ile
        450                 455                 460

Leu Asn Ile Ser Gly Asn Ala Val Lys Phe Thr Lys Glu Gly His Ile
465                 470                 475                 480

Thr Leu Val Ala Ser Ile Val Lys Ala Asp Ser Leu Arg Glu Phe Arg
                485                 490                 495

Thr Pro Glu Phe His Pro Thr Ala Ser Asp Asp His Phe Tyr Leu Lys
            500                 505                 510

Val Gln Val Lys Asp Thr Gly Cys Gly Ile Gly Pro Gln Asp Leu Pro
        515                 520                 525

His Val Phe Thr Lys Phe Ala His Pro Gln Ser Gly Gly Asn Arg Gly
        530                 535                 540

Phe Asn Gly Ser Gly Leu Gly Leu Ala Ile Cys Lys Arg Phe Val Ser
545                 550                 555                 560

Leu Met Gly Gly His Ile Trp Ile Asp Ser Glu Gly Thr Gly Arg Gly
                565                 570                 575

Cys Thr Ala Thr Phe Val Val Lys Leu Gly Val Cys Asp Asn Thr Asn
                580                 585                 590

Thr Tyr Gln Gln Gln Leu Ile Pro Leu Val Trp Pro Ser Ser Ala Asp
            595                 600                 605

Ser Asp Leu Arg Ala Pro Lys Pro Leu Pro Asp Gly Arg Gly Ser Thr
        610                 615                 620

Pro Leu Lys Ser Arg Tyr Gln Arg Ser Val
625                 630

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:Zea mays
      ethylene receptor (ethylene response sensor
      receptor, ERS1-like, ZmERS25) forward primer

<400> SEQUENCE: 28
gagttagtcc tcaggatcta cctcatgt                                      28

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:Zea mays
      ethylene receptor (ethylene response sensor
      receptor, ERS1-like, ZmERS25) reverse primer

<400> SEQUENCE: 29
caattcaatc cgctggtagc atatgt                                        26

<210> SEQ ID NO 30
<211> LENGTH: 5707
<212> TYPE: DNA
<213> ORGANISM: Zea mays
<220> FEATURE:
<223> OTHER INFORMATION: Zea mays ethylene receptor (ethylene
      resistant receptor, ETR2-like), ETR9 genomic DNA

<400> SEQUENCE: 30
tatacaccac agcaaaatgg tgtggtagag aggaagaaca ggacgctgat cgacatggcg      60
agaatgatgc ttggagagtt caagacgccc gagcggtttt tgtcggaaga tgtgaacaca     120
gcctgccatg ccataaacca gctctatctg catcgtctcc tcaagaagac ctcctacgaa     180
```

```
ctccttatcg gtaacaaacc caatgtctct tactttcgtg tatttgggag caaatgctac    240
attctggtga agaaaggtag acattctaaa tttgctccca aagcagtaga agggttctta    300
ctagggtatg actcaaatac aaaggcgtat agagtcttca acaaatcatc ggattagtt    360 gaagtctcta gcgacattgt atttgatgag actaatggct ctccaagaga gcaagttgat    420
cttgatgatg tagatgaaga agaaataacg acgaccgcaa tgcgcacgat ggcgataggc    480
gatgtgcgac cacaggaact acaggaacaa gataaaccat cttcctcgac aatggtgcat    540
cccccaactc aagacgttga acaagtacat caagaagagg ggcaagatca agggggagca    600
caagaagaac aggttatgga ggaagaagca ccatgggccc cttcaactca gtccgagca    660 acgatccaaa gacatcaccc cgtcgatcaa attctgggtg acatcatcaa gggagtaact    720
actcgctcac gtttagctaa tttttgtgag cattactcgt tggtctcttc tattgagcct    780
ttcagggtag aagaggcctt gcaggatccg gactgggtgt tggccatgca ggaagagctc    840
aacaacttca agagaaatga agtctggagc ctggtgccac gtccaaagca aaatgttgtg    900
ggaaccaagt gggtgttccg gaacaagcaa gatgagcacg gggtggtgac aagaaacaag    960
gctcgacttg tggcaaaagg ttatgcccaa gtcgcaggtt tggatttcga ggagactttt   1020
gctcatgttg ctaggctaga gtcaattagg attttattag cctatgctgc tcaccactct   1080
tttaggctgt tccaaatgga cgtgaagagc gctttcctca acgggccaat taaggaggag   1140
gtatacgtgg aacaaccctc tggctttaag gatgacaggt atcatgacca tgtgtataag   1200
ctctctaagg cgctctatgg acttaagcaa gccccaagag catggtatga atgccttaga   1260
gatttcttaa ttgctaatgc cttcaaggtt gggaaagctg atcccactct ttttaccaag   1320
acttgtgatg gtgatctctt tgtgtgccaa atttatgtcg atgacataat atttggttct   1380
actaatcaaa agtcttgtga ggagtttagc agggtgatga tgcaaaagtt cgagatgtcg   1440
atgatgggcg agttgaccta cttccttggg ttccaagtga agcaactcaa agacggcaca   1500
ttcatctccc aaatgaagta cactcaggtc ttctcaagag gtttgggatg aaggacgcca   1560
agcccgcgaa gacactaatg ggaactgacg ggcatattga cctcaacaaa ggaggtaagt   1620
ccgttgatcc gtagccagcc cacgtgtaga cggttatggt gctagtaccg gtgccaacgc   1680
tgtgtttctt ggcgggcgtt gctgctcctc ctccgcttga ggattgctgc tgcatccggc   1740
aggagggatg gtcggaggcg gaaggtgggc ggcttttgac actcctccgt tcttcttcgt   1800
tctaccaatt caataactat gtttggattt atcggagggg tttatcggat ttggctaaat   1860
cccctactgc ccgaattttg gcggactggt gattcgattt tggccgatag atagatttcg   1920
atgctacttt taggaaagac taatcttcac agggggggcct atccgtccca agcaacgat   1980 ttgctttacg ccagatcttg attttgtgtg ccgcagtttg attaactgaa aatctgtgat   2040
ggccgtctgg tgaatgcagg agcgtcggca cccgcagcgt ggaatcgacg acgggcgcct   2100
ccagtcggtt cagaaatgcg caaatgcgcg tctgaatgaa gcctggttgg aggtggtaga   2160
cccgatggtg gtgggaacgg cactgctgcg cggggtttcc tccgcgtgga tcctcctgtt   2220
cctctcctcc ctgctcctct cgccgtcagc ggcgtctgtc gatttcggcc actgcggcgg   2280
ctgcgacgac gccgacgacg gcgccctctc cagcacctat aacatcctgc aatgccagaa   2340
ggtcagcgac ttcctcatcg ccgcggccta cttctccatc ccgctcgagc tgctctactt   2400
cgccaccctg ctccgacctct tcccctcaa atggatcgtg ctgcagttcg gcgccttcat   2460
cgtgctctgc ggcctcacgc acctcatcac tgtgttcacc tacgagccgc actccttcca   2520
cctcgtactc gcccttaccg tcgccaagtt cctgacggca ctggtctcct tcgcgacggc   2580
```

```
catcaccctg ctgacgctga taccacagct cctgagggtg aaggtcaggg aaaacttcct    2640
gatgaacaag gcgcgtgagc tggaccggga ggtgggggagg atgaaaagga aagaagaggc   2700
gagctggcat gtgcgcatgc tcacacagga gatccgcaag tcgctcgaca gacataccat    2760
cttgtacacc accatggttg agctctcgaa ggcactggaa ctgcagaatt gtgctgtctg    2820
gatgcctgat gagaccagga gcacgatgat cttaacacat cagctgaggg aaagggatat    2880
aatggaccca cagaaacact cgattcctat tgatgatccg gatgttcaag aaataaaggc    2940
aaccaaggat gcaaaagttc ttggcccaga ttcggcgcta gggggtttcta gccgaagcaa   3000 gcatgaagca gggcctgtgg ctgcaataag gatgccgatg ttaagggtgt caaatttcaa    3060
aggagggact ccggaagtga tgcagacgag ctatgctatc ttggttctgg ttttgcctaa    3120
tgatggttca ttagggtggg gtcgaagaga gttggagatt gttgaggtag ttgctgacca    3180
agttgcagtc gctctgtcac atgctgcact cctagaggag tctcagctga tgcgagagaa    3240
gcttgccgag cagcataggg acttgctgca ggcaaaggat gaagccatga gggcagggga    3300
cgctaggaat tccttccaga ctgcaatgta cgatggaatg cgaaggccaa tgcactcaat    3360
ccttggtctc gtctcaatga tgcaacagga gagcatgaat ccagagcaaa ggcttgtgat    3420
ggatgccatt gccaagacaa gcagtgttgc atccacactg atgaacgatg tgatgcaaac    3480
atcgacaatg aactgtgagc acttgtcttt ggtcaggagg ccgttcaacc ttcattcctt    3540
cattaaagaa gttgttggag tggtcagatg tctaactggt tgcaagggtg tggagtttga    3600
gtttcaagtg gagaattctt tgccagaaag gatcattggt gatgagaaga gagtcttcca    3660
tattgtcctg cacatggtag gcactctaac agaccgatgt aatgctggct gtatctcatt    3720
atatgtaaat gtccataatg aggttgaaga taggcataat catgactgga tgctgcgaag    3780
agcaaacttc tctgggggct atgtatgtgt gaaatttgag attaggatta gaaaatcaaa    3840
gggctatctg ttgagttcat caagcagtca gataagtcag ggatccaaac ccaacaattc    3900
tgagatgggg cttagcttca atatgtgcaa gaagattgtg caggtaaatc aaaataatag    3960
aatatcttaa gcatttatac ccgcaaattt ttttgtacag ctaggcacta gcagcttaga    4020
cttggccgtc acatagatag tttgctatac accaattgaa ctgccaaact acagaatgtg    4080
tttagtggct atagtgtggc cttttttgtgc aagtgcttgg aatatttatt atctcacctc    4140
aaactgggca tactgagagg acatattggt ccttatgttg aacttacgtt ttagtcataa    4200 ctattttat ggtatttctt ccgtagtatg tgtgacttgc atagatatat ttaattggta    4260
tgcttgtagt agcccgaacc tcagcgactc tatttgattg ttatgttttg gtttgcaatt    4320
tgttcatcca gttgtggaag tggccaatgt atacttgatt tgatgtgcaa tcattagtgt    4380
gcttactgat acgagccctc ctttgtgctg cagatgatga atggcaatat ttggtcagta    4440
tcagattcta aaagcatcgg agaaactatc atgctagtcc tccagttcca gttggaacct    4500
gtgactccgg tctctggagc gtcctcagat ttgtacagat catccgcaat tcccaacttt    4560
aatgggctca gagtcctcct tgcggacagc gactgcacca accgagctgt aactcacagg    4620
ctcctagaga agcttggttg ccgagtcctt tcggtcgctt ctggcgtcca atgcatcagc    4680
tccttcgctg cggagtcgtc cttccagctg gtggttcttg atcttgacat gcagacgatg    4740
gatggattcg aagtagcccg cgcgatcagg aagttcagta gcaatagttg gctgccgttg    4800
attattgccc tagcagcaag aatcgacgac aacatccggg atcgttgcca gaggtcagga    4860
gtaaatggcc tgatccagaa accggtcaca ttagccgcgc tggagatgaa actgtataga    4920
gtccttcaga acaattaaaa gagcctgacg gttctcattt ctttcaatct caatagattg    4980
```

-continued

| | |
|---|---|
| ctatagcttg atcggtaact aatttctgcc aggttagctc catacaatca caaaaaaaaa | 5040 |
| aacattttga ggcaaaaggg aaatgtatag gaagctgaaa gcatcgcttt ctgcttggtt | 5100 |
| cctcggtgaa ggaggaggag gacgactacg acaggaaggt acaaaaaact tggagagatc | 5160 |
| atactgttag aacttagacc cattcatctg taaaccctca gataagcaaa gaattagatt | 5220 |
| catgcactaa cactaaccac gatataatta gtttggacga aatccatgag ctgttgagtt | 5280 |
| tgtgattggg actcagaatg gatgggggtt cagtgaatgc agcggcatat gtgtctacag | 5340 |
| gggggaaaaa ggaacttttg ttattggtta gacatgctgc aaaagcaggc tggatgagat | 5400 |
| tgcagacaag aaggcagacg atgcggctga tgctgacctt ttttacatta cagacttggg | 5460 |
| ctggttctgg tcagcgaacc cttgcttgct tatacgatat cctctgttcc ttacacgata | 5520 |
| tccttctaga aacactttaa gatataaact agtttttttt aagcacgtta gcatcagtgg | 5580 |
| aacagtttgg gtagtaaaaa tctggtgcat tggcacctaa gcttctttgg tcacctcaag | 5640 |
| agctctcaac aatcagagcg attgtctaat gagaatccac ggccagattt ggtgttttga | 5700 |
| cccggtt | 5707 |

<210> SEQ ID NO 31
<211> LENGTH: 2301
<212> TYPE: DNA
<213> ORGANISM: Zea mays
<220> FEATURE:
<223> OTHER INFORMATION: Zea mays ethylene receptor (ethylene resistant receptor, ETR2-like), ETR9 coding sequence (CDS)

<400> SEQUENCE: 31

| | |
|---|---|
| atggtggtgg gaacggcact gctgcgcggg gtttcctccg cgtggatcct cctgttcctc | 60 |
| tcctccctgc tcctctcgcc gtcagcggcg tctgtcgatt tcggccactg cggcggctgc | 120 |
| gacgacgccg acgacggcgc cctctccagc acctataaca tcctgcaatg ccagaaggtc | 180 |
| agcgacttcc tcatcgccgc ggcctacttc tccatcccgc tcgagctgct ctacttcgcc | 240 |
| acctgctccg acctcttccc cctcaaatgg atcgtgctgc agttcggcgc cttcatcgtg | 300 |
| ctctgcggcc tcacgcacct catcactgtg ttcacctacg agccgcactc cttccacctc | 360 |
| gtactcgccc ttaccgtcgc caagttcctg acggcactgg tctccttcgc gacggccatc | 420 |
| accctgctga cgctgatacc acagctcctg agggtgaagg tcaggaaaa cttcctgatg | 480 |
| aacaaggcgc gtgagctgga ccgggaggtg gggaggatga aaggaaaga gaggcgagc | 540 |
| tggcatgtgc gcatgctcac acaggagatc cgcaagtcgc tcgacagaca taccatcttg | 600 |
| tacaccacca tggttgagct ctcgaaggca ctggaactgc agaattgtgc tgtctggatg | 660 |
| cctgatgaga ccaggagcac gatgatctta acacatcagc tgagggaaag ggatataatg | 720 |
| gacccacaga aacactcgat tcctattgat gatccggatg ttcaagaaat aaaggcaacc | 780 |
| aaggatgcaa aagttcttgg cccagattcg gcgctagggg tttctagccg aagcaagcat | 840 |
| gaagcagggc ctgtggctgc aataaggatg ccgatgttaa gggtgtcaaa tttcaaagga | 900 |
| gggactccgg aagtgatgca gacgagctat gctatcttgg ttctggtttt gcctaatgat | 960 |
| ggttcattag ggtggggtcg aagagagttg gagattgttg aggtagttgc tgaccaagtt | 1020 |
| gcagtcgctc tgtcacatgc tgcactccta gaggagtctc agctgatgcg agagaagctt | 1080 |
| gccgagcagc ataggggactt gctgcaggca aaggatgaag ccatgagggc aggggacgct | 1140 |
| aggaattcct tccagactgc aatgtacgat ggaatgcgaa ggccaatgca ctcaatcctt | 1200 |
| ggtctcgtct caatgatgca acaggagagc atgaatccag agcaaaggct tgtgatggat | 1260 |

```
gccattgcca agacaagcag tgttgcatcc acactgatga acgatgtgat gcaaacatcg    1320
acaatgaact gtgagcactt gtctttggtc aggaggccgt tcaaccttca ttccttcatt    1380
aaagaagttg ttggagtggt cagatgtcta actggttgca agggtgtgga gtttgagttt    1440
caagtggaga attctttgcc agaaaggatc attggtgatg agaagagagt cttccatatt    1500
gtcctgcaca tggtaggcac tctaacagac cgatgtaatg ctggctgtat ctcattatat    1560
gtaaatgtcc ataatgaggt tgaagatagg cataatcatg actggatgct gcgaagagca    1620
aacttctctg ggggctatgt atgtgtgaaa tttgagatta ggattagaaa atcaaagggc    1680
tatctgttga gttcatcaag cagtcagata agtcagggat ccaaacccaa caattctgag    1740
atggggctta gcttcaatat gtgcaagaag attgtgcaga tgatgaatgg caatatttgg    1800
tcagtatcag attctaaaag catcggagaa actatcatgc tagtcctcca gttccagttg    1860
gaacctgtga ctccggtctc tggagcgtcc tcagatttgt acagatcatc cgcaattccc    1920
aactttaatg ggctcagagt cctccttgcg gacagcgact gcaccaaccg agctgtaact    1980
cacaggctcc tagagaagct tggttgccga gtcctttcgg tcgcttctgg cgtccaatgc    2040
atcagctcct tcgctgcgga gtcgtccttc cagctggtgg ttcttgatct tgacatgcag    2100
acgatggatg gattcgaagt agcccgcgcg atcaggaagt tcagtagcaa tagttggctg    2160
ccgttgatta ttgccctagc agcaagaatc gacgacaaca tccgggatcg ttgccagagg    2220
tcaggagtaa atggcctgat ccagaaaccg gtcacattag ccgcgctggg agatgaactg    2280
tatagagtcc ttcagaacaa t                                              2301
```

<210> SEQ ID NO 32
<211> LENGTH: 767
<212> TYPE: PRT
<213> ORGANISM: Zea mays
<220> FEATURE:
<223> OTHER INFORMATION: Zea mays ethylene receptor (ethylene resistant receptor, ETR2-like), ETR9 protein

<400> SEQUENCE: 32

```
Met Val Val Gly Thr Ala Leu Leu Arg Gly Val Ser Ser Ala Trp Ile
 1               5                  10                  15
Leu Leu Phe Leu Ser Ser Leu Leu Leu Ser Pro Ser Ala Ala Ser Val
                20                  25                  30
Asp Phe Gly His Cys Gly Gly Cys Asp Asp Ala Asp Gly Ala Leu
             35                  40                  45
Ser Ser Thr Tyr Asn Ile Leu Gln Cys Gln Lys Val Ser Asp Phe Leu
         50                  55                  60
Ile Ala Ala Ala Tyr Phe Ser Ile Pro Leu Glu Leu Tyr Phe Ala
 65                  70                  75                  80
Thr Cys Ser Asp Leu Phe Pro Leu Lys Trp Ile Val Leu Gln Phe Gly
                 85                  90                  95
Ala Phe Ile Val Leu Cys Gly Leu Thr His Leu Ile Thr Val Phe Thr
                100                 105                 110
Tyr Glu Pro His Ser Phe His Leu Val Leu Ala Leu Thr Val Ala Lys
            115                 120                 125
Phe Leu Thr Ala Leu Val Ser Phe Ala Thr Ala Ile Thr Leu Leu Thr
        130                 135                 140
Leu Ile Pro Gln Leu Leu Arg Val Lys Val Arg Glu Asn Phe Leu Met
145                 150                 155                 160
Asn Lys Ala Arg Glu Leu Asp Arg Glu Val Gly Arg Met Lys Arg Lys
                165                 170                 175
```

```
Glu Glu Ala Ser Trp His Val Arg Met Leu Thr Gln Glu Ile Arg Lys
            180                 185                 190

Ser Leu Asp Arg His Thr Ile Leu Tyr Thr Thr Met Val Glu Leu Ser
        195                 200                 205

Lys Ala Leu Glu Leu Gln Asn Cys Ala Val Trp Met Pro Asp Glu Thr
    210                 215                 220

Arg Ser Thr Met Ile Leu Thr His Gln Leu Arg Glu Arg Asp Ile Met
225                 230                 235                 240

Asp Pro Gln Lys His Ser Ile Pro Ile Asp Asp Pro Val Gln Glu
                245                 250                 255

Ile Lys Ala Thr Lys Asp Ala Lys Val Leu Gly Pro Ser Ala Leu
                260                 265                 270

Gly Val Ser Ser Arg Ser Lys His Glu Ala Gly Pro Val Ala Ala Ile
        275                 280                 285

Arg Met Pro Met Leu Arg Val Ser Asn Phe Lys Gly Gly Thr Pro Glu
        290                 295                 300

Val Met Gln Thr Ser Tyr Ala Ile Leu Val Leu Val Leu Pro Asn Asp
305                 310                 315                 320

Gly Ser Leu Gly Trp Gly Arg Arg Glu Leu Glu Ile Val Glu Val Val
                325                 330                 335

Ala Asp Gln Val Ala Val Ala Leu Ser His Ala Ala Leu Leu Glu Glu
        340                 345                 350

Ser Gln Leu Met Arg Glu Lys Leu Ala Glu Gln His Arg Asp Leu Leu
        355                 360                 365

Gln Ala Lys Asp Glu Ala Met Arg Ala Gly Asp Ala Arg Asn Ser Phe
    370                 375                 380

Gln Thr Ala Met Tyr Asp Gly Met Arg Arg Pro Met His Ser Ile Leu
385                 390                 395                 400

Gly Leu Val Ser Met Met Gln Gln Glu Ser Met Asn Pro Glu Gln Arg
                405                 410                 415

Leu Val Met Asp Ala Ile Ala Lys Thr Ser Ser Val Ala Ser Thr Leu
        420                 425                 430

Met Asn Asp Val Met Gln Thr Ser Thr Met Asn Cys Glu His Leu Ser
        435                 440                 445

Leu Val Arg Arg Pro Phe Asn Leu His Ser Phe Ile Lys Glu Val Val
    450                 455                 460

Gly Val Val Arg Cys Leu Thr Gly Cys Lys Gly Val Glu Phe Glu Phe
465                 470                 475                 480

Gln Val Glu Asn Ser Leu Pro Glu Arg Ile Ile Gly Asp Glu Lys Arg
                485                 490                 495

Val Phe His Ile Val Leu His Met Val Gly Thr Leu Thr Asp Arg Cys
                500                 505                 510

Asn Ala Gly Cys Ile Ser Leu Tyr Val Asn Val His Asn Glu Val Glu
        515                 520                 525

Asp Arg His Asn His Asp Trp Met Leu Arg Arg Ala Asn Phe Ser Gly
        530                 535                 540

Gly Tyr Val Cys Val Lys Phe Glu Ile Arg Ile Arg Lys Ser Lys Gly
545                 550                 555                 560

Tyr Leu Leu Ser Ser Ser Ser Ser Gln Ile Ser Gln Gly Ser Lys Pro
                565                 570                 575

Asn Asn Ser Glu Met Gly Leu Ser Phe Asn Met Cys Lys Lys Ile Val
        580                 585                 590

Gln Met Met Asn Gly Asn Ile Trp Ser Val Ser Asp Ser Lys Ser Ile
    595                 600                 605
```

```
Gly Glu Thr Ile Met Leu Val Leu Gln Phe Gln Leu Glu Pro Val Thr
    610                 615                 620

Pro Val Ser Gly Ala Ser Ser Asp Leu Tyr Arg Ser Ser Ala Ile Pro
625                 630                 635                 640

Asn Phe Asn Gly Leu Arg Val Leu Leu Ala Asp Ser Asp Cys Thr Asn
                645                 650                 655

Arg Ala Val Thr His Arg Leu Leu Glu Lys Leu Gly Cys Arg Val Leu
            660                 665                 670

Ser Val Ala Ser Gly Val Gln Cys Ile Ser Ser Phe Ala Ala Glu Ser
        675                 680                 685

Ser Phe Gln Leu Val Val Leu Asp Leu Asp Met Gln Thr Met Asp Gly
    690                 695                 700

Phe Glu Val Ala Arg Ala Ile Arg Lys Phe Ser Ser Asn Ser Trp Leu
705                 710                 715                 720

Pro Leu Ile Ile Ala Leu Ala Ala Arg Ile Asp Asp Asn Ile Arg Asp
                725                 730                 735

Arg Cys Gln Arg Ser Gly Val Asn Gly Leu Ile Gln Lys Pro Val Thr
            740                 745                 750

Leu Ala Ala Leu Gly Asp Glu Leu Tyr Arg Val Leu Gln Asn Asn
        755                 760                 765

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:Zea mays
      ethylene receptor (ethylene resistant receptor,
      ETR2-like ZmETR9) ETR9 forward primer

<400> SEQUENCE: 33
gctatgtatg tgtgaaattt gagattagga                                    30

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence:Zea mays
      ethylene receptor (ethylene resistant receptor,
      ETR2-like ZmETR9) ETR9 reverse primer

<400> SEQUENCE: 34
agctaacctg gcagaaatta gttaccga                                      28

<210> SEQ ID NO 35
<211> LENGTH: 5573
<212> TYPE: DNA
<213> ORGANISM: Zea mays
<220> FEATURE:
<223> OTHER INFORMATION: Zea mays ethylene receptor (ethylene
      resistant receptor, ETR2-like), ETR40 genomic DNA

<400> SEQUENCE: 35
aaactgcgca actcgtgaaa ggtaggcgga tctgggtcga cctgcaggtc aacggatcag    60
actccaaggc ctacaacaag catatcgac cccgattcta gcaataaaag acaaggttcg    120
tcttcacccc tactttccta tgccaattat ccggttggtg aggtgacaca gtaaccaatg    180
aggtgggtgt acgaatggga ggacattaag tactaccaaa tgttggtgga gtcatggatt    240
acgacttctt cgtggaccga tcagacttgg acagggtaca atgcacaatt gatacatgag    300
```

```
caaggtatta tgttgctatc aacggaggag tataatatgg cacaagcaca atatcagtgg    360
aatgcaccat gtgtgaatga tctttgacgg agcaacaact gtgaactatg aatggtgtat    420
ttttatcttc gtcattgttt gtgaactatg aaactgctaa atattattat taaaattgtg    480
atattgttta gggtcatctt ttgtttaaat tatggagcct taatatgctt tatttacaaa    540
atacatatag ctcggtcttt atttctatgc tgtcgattta tcaggccaaa aaccgattaa    600
tcagtcttat cgatttatgg gttttgaatt aaaattttt gaccaattcc tacctatttt     660
caccggtatc gatgggcaca tgttttcaca atttcacccc tcagatcttg ttcggttatt    720
ttcaatctat atagattgga agtaattgat tcaaattgaa agaaatttta acttactaag    780
attaaaattc actaaatctt tctcaatcca tataaattag gatagaaccg aacaaaccct    840
caaccggttt agtgaacccc gccggagaga caacccaacc cccctgctcg acccgctgaa    900
ctgccgaagc atcgcctact cttcctactc agctccgctg gtccggtcgt cgcgtagcgc    960
cctcaccccc agccaccccc accacgaagg ccgcgcgctc cccgccttcc gacgtcgctc   1020
tctccgccca gctcaagcgc ccagcggtga gggaagggaa ggaaaaacag accttttttt   1080
ttcttctcgg cggcctcgtg actatggatc cgccgagctc cggtctcccg ccggtgccga   1140
ggtttcctgg ctcgatccgt gaccggccca cgtggagacg gtgctggtgc tagtaccggt   1200
gcctccaccg tgtttcttgg cgaccttact acctcctctc ctcctctgga agattgctgc   1260
tgcagcctgc aggaaagatg gccgaacgcc gaaggtgggc agcgttagtt actcctccat   1320
gcttttttcc ttcagttcaa caaatatgtt tggatttttt tttaccggac tgtggaatgc   1380
ttcgagctcg ggggtttatc ggatttgggc tgttctaaat ctcctaccta ctctggccca   1440
tattttacc ttctggagta cgtgtataac aagatccatg gtggactgat ggattcggtt    1500
ttgaccgata catgtatttc gatgctattt tttggaagga ttaaatcttc aacacgtgcc   1560
caagcccaac cgcccaaagg catcgatttg cttttcgcca gatcttgatt tgtgtgccgc   1620
ggtttgattg attgcaaagc tgtgatgtta actgcgttca atttgtactt atactacatc   1680
tgatgaatgc aggagcgtcg gcgcgtgcag tgtggaatcg acgccgagcg cctccagtcg   1740
gtgcaggaat gcgcaaatgc acgtctgaat gaagcctggt tggtggtaga gccgatggtg   1800
gtgggaacgg cgccgtgcgg ggtctccgtc tcctccgtgt ggatcctcct gctcctttcc   1860
tccctgctcc tctcgccgtc ggcggcgtcc gtcgatttcg gccactgcgg ctgcgacgac   1920
gccgacgacg gcgccctctc gagcacctac aacatcctgc aatgccagaa ggtcagcgac   1980
ttcctcatcg ccgcggccta cttctccatc ccgctcgagc tgctctactt cgccacctgc   2040
tccgaccttt tccccctcaa atggatcgtg ctgcagttcg gcgccttcat cgtgctctgc   2100
ggcctcacgc acctcatcac cgtgttcacc tacgacccgc actccttcca cctcgtgctc   2160
gccctcaccg tcgccaagtt catgacggca ctagtctcct tcgccacagc catcacgctg   2220
ctgacactga taccgcagct cctgagggtg aaggtcaggg aaaacttcct ggtgaacaag   2280
gcacgtgagc tggaccggga ggtggggatg atgaaaatga aagaagaggc gagctggcat   2340
gtgcgtatgc tcacacagga gatccgcaag tcgctcgaca ggcacaccat cttgtacacc   2400
accatggttg agctctcgaa agcgctggaa ctgcagaatt gtgctgtctg gatgcccgat   2460
gaaaccagga gcgagatgat cttaactcat cagccagggg aaagggatat aatgaccag    2520
cagaactgct cgattcctat tgatgatcca gatgttcaag aaataaaggc taccaaggac   2580
gcaaaagttc ttgggccaga ttcggcacta ggggttgcta cccgcaagct tgacgtgggg   2640
cctgtggctg caataaggat gccgatgtta agggtgtcaa atttcaaagg agggactcca   2700
```

```
gaagtgatgc agacgagcta tgctatcttg gttctggttt tgcctaatga tggttcattg    2760
gggtggggta agagagagtt ggagattgtt gaagtagttg ctgaccaagt tgcggtcgct    2820
ttgtcacatg ctgcactcct agaggagtct cagctgatgc gagagaaact tgctgagcag    2880
tatagggact tgctgcaggc aaagcatgaa gccatgaggg caggggaagc tcggaattcc    2940
ttccagactg caatgtacga cggaatgcga aggccaatgc actcaatcct tggtcttgtc    3000
tcaatgatgc aacaggagag catgaatcca gagcaaaggg ttgtgatgga tgccattgcc    3060
aagacaagca gtgttgcgtc cacactgatg aatgatgtga tgcaaacatc gacaatgaac    3120
tgtgagcact tgtctttggt gaggaggccg ttcaatcttc attcttttat taaagaagct    3180
gttggagtgg tcagatgtct aactggttgc aagggtgtag agtttgagtt tcaagtggat    3240
aattctttgc cagaaaggat cattggtgat gagaagagag tcttccacat tgtcctgcac    3300
atggtaggca ccctaataaa ccgatgtaat gtcggctgta tctcgttata tgtcaatggt    3360
cataatgagg ttgaagagag gcataatcat gactggatgc tgcggagaac aaacttctct    3420
gggggctatg tttgtgtgaa atttgagatt aggattagaa aatccaagga ctatcttttg    3480
agttcaaacg gtcagataag tcatgggtcc aaaccaaaca attctgagat ggggcttagc    3540
ttcaatatgt gcaagaagat tgtgcaggta aatcgaaata ataaaacatc tcaagcattt    3600
acatccaata ggaagaaaac tatattgtca tctcgtttat gtcactcgct cctggtgctt    3660
ctcaggctct gtatatatat tgctgataat gcttggttag gtttgacttc tatgcaaggt    3720
taatattgtt aaagcgacaa caatttatta gattgtggtg gttctgttac cctacttgac    3780
tcagtttatc ttcgattact tggaccttcc agactttgac agatgctaga aaatattag    3840 cggttctttg atctcgagtg acacaaattt ttttagaacc tgttgactgt tctccatctc    3900
tcgtattttt tgtacagctg gggactagca tcttaggcct taggcttggt cgtcacatag    3960
ctagttggcc acacaccaat ttgaacaaga cagaatatgt ttggcggcca tagtgtggcc    4020
ttttatgcaa gcccttggaa tatttattat ctcataaaaa actgggtaaa ccgtgagaac    4080
atattggccc ttttgttgaa ctgatgcttt agtaattagt cataattatt ttatggtatt    4140
tttttctgga agcttgcatg gtttcgcgta aatatatttc gtctagttat gctagtagta    4200
gcccaaacct cagcgactct atttgattgt tatgattcgg tcagcaattt gttcattagc    4260
tgtgggaatg gtcaatgcgc acttgatttg atgtacagtc attagtacgc tgatgtgagc    4320
ccttatttct gctgcagatg atgaacggca acatttggtc agtatcagat tctaaaagcg    4380
ttggagaaac catcatgctg gtcctccagt tccagctgca gcctctgact gcggtctcct    4440
ccgcggcgtc ttcagacttg agccgatcgt ccgcaatccc caacttcaac gggctcagag    4500
tcctcctggc ggacagcgac gacaccaaca gagcagtaac acacaggctc tggagaagc    4560 tcggctgccg ggtccttctg gtcgcctccg gtgtccaatg cacgagctcc ttcgccgccg    4620
agccgtcctt ccagctggtg gtcctggacc tcgccttgca gaggacggac gggctcgaag    4680
tggcccgcgc gatcaggaag ttcagtagca atagctggct gccgctgatc gtcgccctag    4740
ctgcgaggat cgatgacaag gtccgagacg gatgccagag gtcggggata agcggcctga    4800
tccagaaacc ggccacgtta gctgcgctgg gagatgagct gtatagggtc cttcagaaca    4860
gttgaaagtg ccgcctgatg gttctcattg ctttcagaat tctcaataga ccgctgtagc    4920
ttggttagat ccatacattc acaaaacatt tgggggcagg cgaagggaaa tgtataggaa    4980
aagctggaag accgctgctt ctcgcttggt tcctcagtag tgaaggacga cggtgacagg    5040
aaggtacaga attttggaga gatcatactg gtagagctta gactcattca tttgtaaaac    5100
```

-continued

```
cctcggataa tccaaggttt agattcttgc actagcacta accacggtat aaatagtttg      5160
gacgaaatcc atggatgggt tcagtgaatg ctggcatagt agatgcctaa aggggggcaag     5220 gaacttttgt tatcggttag acatgctgaa aagcaggccg gatgagattg cggacaggaa     5280
ggcagctgat acggccgatg ctgaccttgt atcttgttga agattaaata ctatggtagt     5340
agtacttgca gtcttgatct ggtgggtagt gctggtgctc ctgctgcatt tcttacttgc     5400
ttggcctgct tctggccagc aaactcctgc ttgccatctt cttagcactg attcctatgg     5460
tttttttaat agggtatcct ttcaactgtt gagacacatt accacacata tataaaaaac     5520
atttttaatc ccttgctacc gaagcttcag atgtcatctc aagagctatt cta            5573
```

<210> SEQ ID NO 36
<211> LENGTH: 2298
<212> TYPE: DNA
<213> ORGANISM: Zea mays
<220> FEATURE:
<223> OTHER INFORMATION: Zea mays ethylene receptor (ethylene
      resistant receptor, ETR2-like), ETR40 coding sequence (CDS)

<400> SEQUENCE: 36

```
atggtggtgg gaacggcgcc gtgcggggtc tccgtctcct ccgtgtggat cctcctgctc       60
ctttcctccc tgctcctctc gccgtcggcg gcgtccgtcg atttcggcca ctgcggctgc      120
gacgacgccg acgacggcgc cctctcgagc acctacaaca tcctgcaatg ccagaaggtc      180
agcgacttcc tcatcgccgc ggcctacttc tccatcccgc tcgagctgct ctacttcgcc      240
acctgctccg acctttttccc cctcaaatgg atcgtgctgc agttcggcgc cttcatcgtg      300
ctctgcggcc tcacgcacct catcaccgtg ttcacctacg acccgcactc cttccacctc      360
gtgctcgccc tcaccgtcgc caagttcatg acggcactag tctccttcgc cacagccatc      420
acgctgctga cactgatacc gcagctcctg agggtgaagg tcagggaaaa cttcctggtg      480
aacaaggcac gtgagctgga ccgggaggtg gggatgatga aaatgaaaga agaggcgagc      540
tggcatgtgc gtatgctcac acaggagatc cgcaagtcgc tcgacaggca caccatcttg      600
tacaccacca tggttgagct ctcgaaagcg ctggaactgc agaattgtgc tgtctggatg      660
cccgatgaaa ccaggagcga atgatctta actcatcagc caagggaaag ggatataatg      720
gaccagcaga actgctcgat tcctattgat gatccagatg ttcaagaaat aaaggctacc      780
aaggacgcaa agttcttggg ccagattcgg gcactagggg ttgctacccg caagcttgac      840
gtggggcctg tggctgcaat aaggatgccg atgttaaggg tgtcaaattt caaaggaggg      900
actccagaag tgatgcagac gagctatgct atcttggttc tggttttgcc taatgatggt      960
tcattggggt ggggtagaag agagttggag attgttgaag tagttgctga ccaagttgcg     1020
gtcgctttgt cacatgctgc actcctagag gagtctcagc tgatgcgaga gaaacttgct     1080
gagcagtata gggacttgct gcaggcaaag catgaagcca tgagggcagg ggaagctcgg     1140
aattccttcc agactgcaat gtacgacgga atgcgaaggc caatgcactc aatccttggt     1200
cttgtctcaa tgatgcaaca ggagagcatg aatccagagc aaagggttgt gatggatgcc     1260
attgccaaga caagcagtgt tgcgtccaca ctgatgaatg atgtgatgca aacatcgaca     1320
atgaactgtg agcacttgtc tttggtgagg aggccgttca atcttcattc tttttattaaa     1380 gaagctgttg gagtggtcag atgtctaact ggttgcaagg gtgtagagtt tgagtttcaa     1440
gtggataatt cttttgccaga aaggatcatt ggtgatgaga agagagtctt ccacattgtc     1500
ctgcacatgt taggcaccct aataaaccga tgtaatgtcg gctgtatctc gttatatgtc     1560
aatggtcata tgaggttgga agagaggcat aatcatgact ggatgctgcg gagaacaaac     1620
```

-continued

```
ttctctgggg gctatgtttg tgtgaaattt gagattagga ttagaaaatc caaggactat    1680
cttttgagtt caaacggtca gataagtcat gggtccaaac caaacaattc tgagatgggg    1740
cttagcttca atatgtgcaa gaagattgtg cagatgatga acggcaacat ttggtcagta    1800
tcagattcta aaagcgttgg agaaaccatc atgctggtcc tccagttcca gctgcagcct    1860
ctgactgcgg tctcctccgc ggcgtcttca gacttgagcc gatcgtccgc aatccccaac    1920
ttcaacgggc tcagagtcct cctggcggac agcgacgaca ccaacagagc agtaacacac    1980
aggctcctgg agaagctcgg ctgccgggtc ctttcggtcg cctccggtgt ccaatgcacg    2040
agctccttcg ccgccgagcc gtccttccag ctggtggtcc tggacctcgc cttgcagagg    2100
acggacgggc tcgaagtggc ccgcgcgatc aggaagttca gtagcaatag ctggctgccg    2160
ctgatcgtcg ccctagctgc gaggatcgat gacaaggtcc gagacggatg ccagaggtcg    2220
gggataagcg gcctgatcca gaaaccggcc acgttagctg cgctgggaga tgagctgtat    2280
agggtccttc agaacagt                                                  2298
```

<210> SEQ ID NO 37
<211> LENGTH: 766
<212> TYPE: PRT
<213> ORGANISM: Zea mays
<220> FEATURE:
<223> OTHER INFORMATION: Zea mays ethylene receptor (ethylene resistant receptor, ETR2-like), ETR40 protein

<400> SEQUENCE: 37

```
Met Val Val Gly Thr Ala Pro Cys Gly Val Ser Val Ser Ser Val Trp
  1               5                  10                  15

Ile Leu Leu Leu Leu Ser Ser Leu Leu Leu Ser Pro Ser Ala Ala Ser
                 20                  25                  30

Val Asp Phe Gly His Cys Gly Cys Asp Asp Ala Asp Asp Gly Ala Leu
             35                  40                  45

Ser Ser Thr Tyr Asn Ile Leu Gln Cys Gln Lys Val Ser Asp Phe Leu
         50                  55                  60

Ile Ala Ala Ala Tyr Phe Ser Ile Pro Leu Glu Leu Leu Tyr Phe Ala
 65                  70                  75                  80

Thr Cys Ser Asp Leu Phe Pro Leu Lys Trp Ile Val Leu Gln Phe Gly
                 85                  90                  95

Ala Phe Ile Val Leu Cys Gly Leu Thr His Leu Ile Thr Val Phe Thr
            100                 105                 110

Tyr Asp Pro His Ser Phe His Leu Val Leu Ala Leu Thr Val Ala Lys
        115                 120                 125

Phe Met Thr Ala Leu Val Ser Phe Ala Thr Ala Ile Thr Leu Leu Thr
    130                 135                 140

Leu Ile Pro Gln Leu Leu Arg Val Lys Val Arg Glu Asn Phe Leu Val
145                 150                 155                 160

Asn Lys Ala Arg Glu Leu Asp Arg Glu Val Gly Met Met Lys Met Lys
                165                 170                 175

Glu Glu Ala Ser Trp His Val Arg Met Leu Thr Gln Glu Ile Arg Lys
            180                 185                 190

Ser Leu Asp Arg His Thr Ile Leu Tyr Thr Thr Met Val Glu Leu Ser
        195                 200                 205

Lys Ala Leu Glu Leu Gln Asn Cys Ala Val Trp Met Pro Asp Glu Thr
    210                 215                 220

Arg Ser Glu Met Ile Leu Thr His Gln Pro Arg Glu Arg Asp Ile Met
225                 230                 235                 240
```

```
Asp Gln Gln Asn Cys Ser Ile Pro Ile Asp Asp Pro Asp Val Gln Glu
                245                 250                 255

Ile Lys Ala Thr Lys Asp Ala Lys Val Leu Gly Pro Asp Ser Ala Leu
            260                 265                 270

Gly Val Ala Thr Arg Lys Leu Asp Val Gly Pro Val Ala Ala Ile Arg
        275                 280                 285

Met Pro Met Leu Arg Val Ser Asn Phe Lys Gly Gly Thr Pro Glu Val
    290                 295                 300

Met Gln Thr Ser Tyr Ala Ile Leu Val Leu Val Leu Pro Asn Asp Gly
305                 310                 315                 320

Ser Leu Gly Trp Gly Arg Arg Glu Leu Glu Ile Val Glu Val Val Ala
                325                 330                 335

Asp Gln Val Ala Val Ala Leu Ser His Ala Ala Leu Leu Glu Glu Ser
                340                 345                 350

Gln Leu Met Arg Glu Lys Leu Ala Glu Gln Tyr Arg Asp Leu Leu Gln
            355                 360                 365

Ala Lys His Glu Ala Met Arg Ala Gly Glu Ala Arg Asn Ser Phe Gln
        370                 375                 380

Thr Ala Met Tyr Asp Gly Met Arg Arg Pro Met His Ser Ile Leu Gly
385                 390                 395                 400

Leu Val Ser Met Met Gln Gln Glu Ser Met Asn Pro Glu Gln Arg Val
                405                 410                 415

Val Met Asp Ala Ile Ala Lys Thr Ser Ser Val Ala Ser Thr Leu Met
                420                 425                 430

Asn Asp Val Met Gln Thr Ser Thr Met Asn Cys Glu His Leu Ser Leu
            435                 440                 445

Val Arg Arg Pro Phe Asn Leu His Ser Phe Ile Lys Glu Ala Val Gly
        450                 455                 460

Val Val Arg Cys Leu Thr Gly Cys Lys Gly Val Glu Phe Glu Phe Gln
465                 470                 475                 480

Val Asp Asn Ser Leu Pro Glu Arg Ile Ile Gly Asp Glu Lys Arg Val
                485                 490                 495

Phe His Ile Val Leu His Met Val Gly Thr Leu Ile Asn Arg Cys Asn
                500                 505                 510

Val Gly Cys Ile Ser Leu Tyr Val Asn Gly His Asn Glu Val Glu Glu
            515                 520                 525

Arg His Asn His Asp Trp Met Leu Arg Arg Thr Asn Phe Ser Gly Gly
        530                 535                 540

Tyr Val Cys Val Lys Phe Glu Ile Arg Ile Arg Lys Ser Lys Asp Tyr
545                 550                 555                 560

Leu Leu Ser Ser Asn Gly Gln Ile Ser His Gly Ser Lys Pro Asn Asn
                565                 570                 575

Ser Glu Met Gly Leu Ser Phe Asn Met Cys Lys Lys Ile Val Gln Met
            580                 585                 590

Met Asn Gly Asn Ile Trp Ser Val Ser Asp Ser Lys Ser Val Gly Glu
        595                 600                 605

Thr Ile Met Leu Val Leu Gln Phe Gln Leu Gln Pro Leu Thr Ala Val
610                 615                 620

Ser Ser Ala Ala Ser Ser Asp Leu Ser Arg Ser Ser Ala Ile Pro Asn
625                 630                 635                 640

Phe Asn Gly Leu Arg Val Leu Ala Asp Ser Asp Asp Thr Asn Arg
                645                 650                 655

Ala Val Thr His Arg Leu Leu Glu Lys Leu Gly Cys Arg Val Leu Ser
```

```
                660              665                670
Val Ala Ser Gly Val Gln Cys Thr Ser Ser Phe Ala Ala Glu Pro Ser
            675                 680                 685

Phe Gln Leu Val Val Leu Asp Leu Ala Leu Gln Arg Thr Asp Gly Leu
        690                 695                 700

Glu Val Ala Arg Ala Ile Arg Lys Phe Ser Ser Asn Ser Trp Leu Pro
705                 710                 715                 720

Leu Ile Val Ala Leu Ala Ala Arg Ile Asp Asp Lys Val Arg Asp Gly
                725                 730                 735

Cys Gln Arg Ser Gly Ile Ser Gly Leu Ile Gln Lys Pro Ala Thr Leu
            740                 745                 750

Ala Ala Leu Gly Asp Glu Leu Tyr Arg Val Leu Gln Asn Ser
            755                 760                 765

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:Zea mays
      ethylene receptor (ethylene resistant receptor,
      ETR2-like, ZmETR40) ETR40 forward primer

<400> SEQUENCE: 38
gctatgtatg tgtgaaattt gagattagga                                    30

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence:Zea mays
      ethylene receptor (ethylene resistant receptor,
      ETR2-like, ZmETR40) ETR40 reverse primer

<400> SEQUENCE: 39
aagctacagc ggtctattga gaattct                                       27

<210> SEQ ID NO 40
<211> LENGTH: 8237
<212> TYPE: DNA
<213> ORGANISM: Zea mays
<220> FEATURE:
<223> OTHER INFORMATION: Zea mays ethylene receptor (ethylene
      insensitive receptor, EIN2-like), E2-25 genomic DNA
<220> FEATURE:
<221> NAME/KEY: modified_base
<222> LOCATION: (126)
<223> OTHER INFORMATION: n = g, a, c or t

<400> SEQUENCE: 40
aaacccactc ttgccacccc gtgacagcag gaaacagtac acagtagcgc ataaccttcc    60
aagaaaattt aattaataaa cccgaagaag ccaagaggga agggaaaaaa aaagaaagaa   120
aaaaanctga cacataagaa aagagcagcg agcaagctga aggtgaaagc cacagcagct   180
cgtccccttc ccccacttc ttcctcagat aaggagaggc cccaggccag agaaaaaagc    240
atcgaatttc cccccgttaa ttggcctgag ccctcagccg tctaccagca gcagctagag   300
gtacgattct cgcattgctt gctccctgcg cctgccctcg attttgctg ttttttcgag    360 ctcctcttcc agttcttttg ccgtgttgga accgcatcta tgcagcctag cgcggggtac   420
tagcgtgatt cggtcagtgg atcccgtcgg gctgctgctt cctcgcggct gatttgcgag   480
aggaagcagg tccccgggaa gcgatctcat ttttcgttat ttttttagct ccctacacca   540
```

-continued

```
aagaccagag tcagatccga ggctacccgc cgccccggca aggattttac ccggccggag     600
ctctgcaaca tcggtgggat cgatggctgc gacctccacg agctccggtg cccacgaatc     660
gaagtcagca gcgccgtgtg gactgagtca cgtgcctggt tcgccgtcct gtccgacgct     720
tctcacctcg agagcccgtc gctgttgcct cggactcgag ggagctggcg gcgcaaacgc     780
cgtgcggcca aaatcgagat ccccaccatc cgaatcgagg tcctctctac cagaatcagt     840
tcccgccgcc gcgtcgaggt agctgtcacc caaattgagc tttccgtcgc tgctggatgt     900
gttggaatcg gaagcttcgg gcgcatagct tgagctcgct caagtgtatc gagcaagcaa     960
accaagcgtt gggggtcttg ctttgcgcct ttgccgcgct agcttagcct atctatccgt    1020
gctaggaatc cccctccctt tcggtgtgat gttttttgact tgccactgcc tggtgttgct    1080
ggggctgctt ttctcttctc ctttggggct ctgaatgaag actgaagaaa tcgaagaga     1140 ggaaagctac gcctgagtcg gggaacgcct acgaagtaag ttttggctta aaggtggaag    1200
cttttgaggt ttctccttgc gaaataaatg cttttttcga tgttatttga tggatttggt    1260
tggtactcgg tcaaaaggtg ttcttggttt gcccttttcta tgctctggct gctgttgcaa    1320
ctgcaacttc cctttccctt agagtttggc gctctaaaag ttggttcact ttgcacgaag    1380
gatttctgtt tcttgttgct gattgggttg tttggatcta tctgcaggca gacaagctag    1440
gttttactgc ttcattgagc acaaagatcc gctgacctct tgctcttggt aaaaatccaa    1500
cctttcttgt attgttttct tcctgggaaa acctccttgt ggtgcataaa cttcgtagta    1560
cactctgcca tttctggaga ggaagctgag aactactatc catatctggc acgacccttg    1620
tcaagaacca tggctgttca catgccatga agctgcttga actggaggca cctaaatgct    1680
gtggattgtt cctatgcaga tgattggatc agtggtttca ggcttcgggg ggttcgatca    1740
gatgttgtat gaataatagc aggattgctt gagagactat agtttgggta ctgtttgctt    1800
ctgtatttac tggtacggtt tcctactgat ctgcggctgc gcaggaaggc attctctttt    1860
ttgccgtacc atggatgcac cggatgttca acagagcatg ggatataagg agtccagggg    1920
tggtatgcct aagttttttcc atgcccttgg accagcactc ctgatttcaa tgggttacat    1980
tgatctcggg aagtgggtgg cagccgttga agctggttct tgttttggat cgacctggt     2040 gttgctggcc ctccttttca atttcactgc cattgtatgt cagtaccttg ctgcttgcat    2100
tggcactgtc acagggaaga atcttgcaga ggtatcggtt taccgatgtt gttccttggt    2160
tttgctggcc ttctattgag atttagttca gtaaatcttt gtttccattt cacaacgcta    2220
tatgatggct tcatattgag ctggacttga aggaacttag aagagcaggg agtagggaaa    2280
ctacatgcga gatattcaat ttatgcgaat tgttgataaa caaatggat caattcactt     2340 gccttgttaa ataattcttt tccatctgta gttcaattat actccctctg ttccacaata    2400
gaagtcgttt tagactttca acaaattcat tcaataattg atgtatatgt tatgtaatgt    2460
gtctagattc gttgccattc atttgaatat agacataaaa agaagaccta aaacgactac    2520
taatttggta cagagggagt agtactgttg gatgtagaag ggcttctttt tggaggaaaa    2580
tatatctttt atctcatctt acttgttctt gatattcctt tcaagttgct aacttttca     2640 tgccttcaca tgaaacaaag atatgccacc aagagtacaa ccagccaaca tgtatattcc    2700
ttggtgttca agctggattg tctttgttga cgtcagagct gagtatggta cttgcagatt    2760
tagttggatg tctctcatac cttttatgtt taaattgtga attctcatcc tgcaaagcaa    2820
tgttacatga tgtagttctg acatgctaga ttctgttggc tatatctgga attttcagat    2880
ttttggcata gcactcggat tcaacctcct gtttgaatat gatgatctca tcacagggat    2940
```

```
atgctttgca acagtggtac ctaatctgct accatatgct atatcccacc tggtaaggtt   3000
actacttcaa gaaagatact tgaacagatg ctgatacact aatgtgactt tatgtttgct   3060
agttacttac cctttatgtc tgctctaggg aaagaagatg aagggacaa taaatgcctg    3120 catagcagga tttgcacttc ttagttatgt gcttggctta ttggttagcc agccacaaat   3180
tcctctcacg atgaatgtaa tattcccaa gatcagtggt gagagtgctt actctctgat    3240
ggcgcttctt ggtgcaaaca taatggcaca caacttctac attcattcat cagttgtcca   3300
ggtaaattgt ttgattagtg cccttggact taaaatttag tgggcaacgc cttgccagaa   3360
atacttcaaa ccatacattt acatttattt caattttagc ttgttgtatg gagtttgtaa   3420
agtcctaaga gtgagcgaga tcattatatt tgaacttctg ttcatgccag ttgaatattg   3480
gatacaattt gaaaattata tttatttcct ttattatttt gatgatttgt gggtacacca   3540
catcgaaata aaacaagatg taattaatcg cgtttcaatt gtttggataa cttcatacaa   3600
gtttccaccg caggatccac actttgttta tctgtacaca ttgtgctcag cttttggaat   3660
tttttgttta gttcatgaaa ttttgtgtct tatgtttggg tttgtagcat atcacaaaac   3720
atcaaaattg taccatttct aacttttcac atcatgttca ttggaaaata ttgacatgtg   3780
caaaaaatgc aagtagtgac agtttgcgta ctttgcagtc gtttgttttc actgaattgt   3840
catcagtttc tgcgtgtttt ttaatcaaga aacattgtat ttgcagggtc agaaaaagtc   3900
atctgcagtt ggtcttggag ccttatttca cgaccacctt ttttcaatat tgttcatttt   3960
tactggaatc tttatggtga actatgttct aatgaactct gcagcagcgg aatctactaa   4020
tactcttctc attaccttcc aagatgttgt agagctaatg aatcaggtaa gcagctaaat   4080
ttcctagttg tttattctct gtgctaagtt tctgctgaat atttttattta ggaagatatc   4140 ctactccgct atagaaaact gaattttga gtactttgca gatatttgta aaccctctgg   4200
caccaactat atttttagtg gttcttctct tctccagcca catcatctcg ctgacatctg   4260
ctatcggtag ccaagtgatt tcacaccatt tattcggtat aaaccttcct ctttctggac   4320
atcgtctcct actgaaggtt tttgccatag ttcctactct gtactgggcg aaagttgcag   4380
gagctgaagg gatataccaa ttattaatta tatgccagat tattcaagcc atgcttcttc   4440
catcttcagt cgtcccactt tttcgtgttg cttcatcaag atcaataatg ggagcccata   4500
gagtgtcttt gcatctggag atactggttt ttcttgcatt tctccttatg ctattttcaa   4560
atatcatatt tgtggcagaa atgctatttg gcgacagtgg gtggatgaac aatctgaaag   4620
gatatactgg aagccctgtg gtgctcccat ataccgtttt agttttagtt gcacttatat   4680
ctgtggcttt ttcactgtac ctggctgtta caccattgag atctggaagt catgaagctg   4740
aatcccatga atggtctgtg cattctcaga gagaactctt gaatacttct caagaaaggg   4800
aagatgttaa ggtggacaat gttacatatg aggaagatca aagatcagat gttgtcccctt  4860 ctcccaggga tgtgcctgac agccatccgg aactggcctt ggactatatt gatacttctg   4920
acactgctgt agaatctgat cacgactctc aacaatctac tgcttatgca tccactgctc   4980
ctgaaacctg ctcctcccg tcgtttactc gcgaggagtc aaaatcagtt gttgcagtca    5040
actggccgga gcctttggag aaggttccta cttctactgt gatggaggaa agcacagtag   5100
aaaatgtggt ctctaggatc acgactgaaa gagatgtttt agtagaaaca gatgttgtct   5160
cgggcaagga taaggaagat atccgtactt tggagtctga gaagtcaatt gttgatagca   5220
ccccatatgt gtctgatgac ggtccgccat cccttacttt cagcagggga aagggctcag   5280
atgcaggaaa tggcagtggt agtctctcaa ggttatctgg tttgggccgt gcagcaagga   5340
```

```
gacagctagc tgctactctt gatgagttct gggggcatct gtttgattac catggtaagc   5400
tcactcaaga agctagcacc aaaaagtttg gtatcttgct tgggatagac cttagaacac   5460
ctagcacatc tgtaagaacg gataaacaag ctgctgaaat acttaagagc ccactggtga   5520
gagactcaat gcggggggca gcttttttgt caagctcagt ggacatgatg tcccctaaga   5580
atgaaacgtc gaatttggaa cttgcatatg ggcttcagag gggacctggc atgggattgt   5640
caagctggtc tcagggtatg cagctaccaa atacacagct gcagagctca agcaatagcc   5700
tacttgagca gagtgcaaga ttaaactcaa attttagttc atcttattca gacaacaatc   5760
agttctacca acctgcaaca attcatggat accagctcac atcttacctg aaacagatga   5820
atgccagccc aagcctttac tctagcatgc cgctggaccc acaacggctt ccaaaatcat   5880
ctgtgtctgc tgtgccaaac tatgctgatt ccatgatgca tgctcgtaat cataacctgc   5940
ttgcttcact gggtggtact actacacagc ttcctgcaac atcccgcgta ggctcaatga   6000
tgcctgaaag atcgtattat gatccttcca gcgttgatgg gaatgaaaac gctggttcac   6060
ctgcttactc aaaaaagtac cacagctcac ctgatatgtc tggaataatc gctgcaagta   6120
gagctgcact cttgaatgaa gcaaagttgg gtgctgccat tggaccacag tcatacctca   6180
gcaggctggc ggcagaaaga tctcaatatg caagctcaac agccaggccc gcggctccat   6240
tagcatttga cgagctttca cctcctaagc tccagagtga tatcttctcg gcgcagtcaa   6300
gcatgagacc aagtgctaga tcccttgggg ctaagcaacc atttgagcaa ttgttcggca   6360
tgtcaagtgc agagctcagt aaaggtgact tcaatcttcc aggcagatca ggtggcgtgg   6420
ccaaggatga tttctcttat aaggaatctg agacgaagct tcttcagtcc ctcaggctct   6480
gcatcatgaa gctccttaag ctagagggat cagggtggcg gttcaagcaa atggtggtt    6540 gtgatgaaga tctaatcgac cgagtcgctg cagccgagaa gctattgatg caagggactg   6600
ccgagaatca actgctgctt catggtggtg atctccagca acattcttcc gaccaggccg   6660
gcatccagta catgcgcacg cttcccaact gcggggagga ctgtgtttgg cgcgcgtcac   6720
tcgtcgttag tttcggtgtc tggtgtgtcc gccgagtgct ggacatgtct ctggtggaaa   6780
gcaggccaga acttggggc aagtatacct atgtccttaa ccgtcttcag gtgagttgtt    6840
atggtcctga actagtttaa ctttttttt tgcaatcgat aatatcctgt ttttaatact     6900
tgcttacaat taggggtgga caatcatctg aaatggcatt acaatataga aaacaaaagg   6960
actggcccag gattttcccg tatttatgaa gatatctagt agcacaaaaa aatagctgtg   7020
aaatcagtta aaaatgacat ttttttttaat gtttgcgtga attcagaaac gttctaaaac   7080
ggtatcatat tatagaaaac gagaatgaag gatttgtgct gttcacttaa cagtgattca   7140
ttttatgttt gtgcagggga tcttggaccc tgcgttctcc aagcctcggg gtgctctgac   7200
aatatgcacc tgccttcaga aagacaccag agtgcgcaat agcccacccc acagtgggct   7260
aacagccatg ggcccggtcc ccacaccgat ccggggcgcc ttcacgaccg caggcgtggt   7320
tctggagatg atcaaggacg tggaggctgc ggtctcaggc cgcaagggca ggagcggcac   7380
ggcggcgggc gacgtcgcct tccccaaggg gaaggagaac ctggcctccg tgctgaagcg   7440
gtacaagcgg cggctcgcca gcaagggcca gtagcgcgcg ggtgtcagac aggcaggcga   7500
tcgcaagcaa tgttaggagg agcctgacta ttgttctcca gggggggctgc cactggcgcc   7560 ggcctccctg agccctggat ttttttcgttg cacgacgttc ctagggaccg gtggttgccc   7620
gatggtcgtc ttggtcccctt ccagcaggtt tttttttttcc ttccctcttt ctgtgggttt   7680 cttttttgtgg gctttgtgat gttttgaaag gggcaactag ggtatgtgct cagaaggact   7740
```

| | |
|---|---:|
| caagatgtac acgcgaagat gtactagtct gctgatgcag cgttgtaaag tccacactct | 7800 |
| gcaggttaac ccttttgggg gccgtcaagt gttagtgcgt gccctatgta tgttaatcac | 7860 |
| ccctgcagag aggttgcgaa tactgaacta ctcacagacc tgcacctgtc gagatcgttt | 7920 |
| gtaatatccg acgtcttgtt cagaattgtt ctcactcttt tttgcccgtt gtgtaattta | 7980 |
| ccctgaaggg acttcaagta cgtgcttcgg caagcacggt cttgaaagaa aaaaaactgt | 8040 |
| tagcatcagt gagctgcctg ttgagcagta aaagagaata caatgtgagc tctcaactca | 8100 |
| aaagcgagat gtgtcacgcg cgtatctcaa gaagcattgg gccaaagctt tttatgccag | 8160 |
| gcaagagaga tgcttccaaa tggccggtcc gaaatgcagg aaatgatgag taatatggtt | 8220 |
| tggcaaacca cttccgt | 8237 |

<210> SEQ ID NO 41
<211> LENGTH: 3765
<212> TYPE: DNA
<213> ORGANISM: Zea mays
<220> FEATURE:
<223> OTHER INFORMATION: Zea mays ethylene receptor (ethylene
      insensitive receptor, EIN2-like), E2-25 coding sequence (CDS)

<400> SEQUENCE: 41

| | |
|---|---:|
| atggatgcac cggatgttca acagagcatg ggatataagg agtccagggg tggtatgcct | 60 |
| aagttttttcc atgcccttgg accagcactc ctgatttcaa tgggttacat tgatctcggg | 120 |
| aagtgggtgg cagccgttga agctggttct tgttttggat tcgacctggt gttgctggct | 180 |
| ctccttttca atttcactgc cattgtatgt cagtaccttg ctgcttgcat tggcactgtc | 240 |
| acagggaaga tcttgcaga gatatgccac caagagtaca accagccaac atgtatattc | 300 |
| cttggtgttc aagctggatt tgtctttgttg acgtcagagc tgagtatgat ttttggcata | 360 |
| gcactcggat tcaacctcct gtttgaatat gatgatctca tcacagggat atgcttttgca | 420 |
| acagtgatgg aagggacaat aaatgcctgc atagcaggat ttgcacttct tagttatgtg | 480 |
| cttggcttat tggttagcca gccacaaatt cctctcacga tgaatgtaat attccccaag | 540 |
| atcagtggtg agagtgctta ctctctgatg gcgcttcttg gtgcaaacat aatggcacac | 600 |
| aacttctaca ttcattcatc aggtcagaaa aagtcatctg cagttggtct tggagcctta | 660 |
| tttcacgacc accttttttc aatattgttc attttactg gaatctttat ggtgaactat | 720 |
| gttctaatga actctgcagc agcggaatct actaatactc ttctcattac cttccaagat | 780 |
| gttgtagagc taatgaatca gatatttgta aaccctctgg caccaactat attttagtg | 840 |
| gttcttctct tctccagcca catcatctcg ctgacatctg ctatcggtag ccaagtgatt | 900 |
| tcacaccatt tattcggtat aaaccttcct cttctggac atcgtctcct actgaaggtt | 960 |
| tttgccatag ttcctactct gtactgggcg aaagttgcag gagctgaagg gatataccaa | 1020 |
| ttattaatta tatgccagat tattcaagcc atgcttcttc catcttcagt cgtcccactt | 1080 |
| tttcgtgttg cttcatcaag atcaataatg ggagcccata gagtgtcttt gcatctggag | 1140 |
| atactggttt tccttgcatt tctccttatg ctattttcaa atatcatatt tgtggcagaa | 1200 |
| atgctatttg gcgacagtgg gtggatgaac aatctgaaag gatatactgg aagccctgtg | 1260 |
| gtgctcccat ataccgtttt agttttagtt gcacttatat ctgtggcttt ttcactgtac | 1320 |
| ctggctgtta caccattgag atctggaagt catgaagctg aatcccatga atggtctgtg | 1380 |
| cattctcaga gagaactctt gaatacttct caagaaaggg aagatgttaa ggtggacaat | 1440 |
| gttacatatg aggaagatca aagatcagat gttgtccctt ctcccaggga tgtgcctgac | 1500 |

```
agccatccgg aactggcctt ggactatatt gatacttctg acactgctgt agaatctgat    1560
cacgactctc aacaatctac tgcttatgca tccactgctc ctgaaacctg ctcctccccg    1620
tcgtttactc gcgaggagtc aaaatcagtt gttgcagtca actggccgga gcctttggag    1680
aaggttccta cttctactgt gatggaggaa agcacagtag aaaatgtggt ctctaggatc    1740
acgactgaaa gagatgtttt agtagaaaca gatgttgtct cgggcaagga taaggaagat    1800
atccgtactt tggagtctga gaagtcaatt gttgatagca ccccatatgt gtctgatgac    1860
ggtccgccat cccttacttt cagcagggga aagggctcag atgcaggaaa tggcagtggt    1920
agtctctcaa ggttatctgg tttgggccgt gcagcaagga gacagctagc tgctactctt    1980
gatgagttct gggggcatct gtttgattac catggtaagc tcactcaaga agctagcacc    2040
aaaaagtttg gtatcttgct tgggatagac cttagaacac ctagcacatc tgtaagaacg    2100
gataaacaag ctgctgaaat acttaagagc ccactggtga gagactcaat gcggggggca    2160
gcttttttgt caagctcagt ggacatgatg tcccctaaga atgaaacgtc gaatttggaa    2220
cttgcatatg ggcttcagag gggacctggc atgggattgt caagctggtc tcagggtatg    2280
cagctaccaa atacacagct gcagagctca agcaatagcc tacttgagca gagtgcaaga    2340
ttaaactcaa attttagttc atcttattca gacaacaatc agttctacca acctgcaaca    2400
attcatggat accagctcac atcttacctg aaacagatga atgccagccc aagcctttac    2460
tctagcatgc cgctggaccc acaacggctt ccaaaatcat ctgtgtctgc tgtgccaaac    2520
tatgctgatt ccatgatgca tgctcgtaat cataacctgc ttgcttcact gggtggtact    2580
actacacagc ttcctgcaac atcccgcgta ggctcaatga tgcctgaaag atcgtattat    2640
gatccttcca gcgttgatgg gaatgaaaac gctggttcac ctgcttactc aaaaaagtac    2700
cacagctcac ctgatatgtc tggaataatc gctgcaagta gagctgcact cttgaatgaa    2760
gcaaagttgg gtgctgccat ggaccacag tcatacctca gcaggctggc ggcagaaaga    2820
tctcaatatg caagctcaac agccaggccc gcggctccat tagcatttga cgagctttca    2880
cctcctaagc tccagagtga tatcttctcg gcgcagtcaa gcatgagacc aagtgctaga    2940
tccctttggg ctaagcaacc atttgagcaa ttgttcggca tgtcaagtgc agagctcagt    3000
aaaggtgact tcaatcttcc aggcagatca ggtggcgtgg ccaaggatga tttctcttat    3060
aaggaatctg agacgaagct tcttcagtcc ctcaggctct gcatcatgaa gctccttaag    3120
ctagagggat cagggtggct gttcaagcaa aatggtggtt gtgatgaaga tctaatcgac    3180
cgagtcgctg cagccgagaa gctattgatg caagggactg ccgagaatca actgctgctt    3240
catggtggtg atctccagca acattcttcc gaccaggccg gcatccagta catgcgcacg    3300
cttcccaact gcggggagga ctgtgtttgg cgcgcgtcac tcgtcgttag tttcggtgtc    3360
tggtgtgtcc gccgagtgct ggacatgtct ctggtggaaa gcaggccaga actttgggc    3420 aagtatacct atgtccttaa ccgtcttcag gggatcttgg accctgcgtt ctccaagcct    3480
cggggtgctc tgacaatatg cacctgcctt cagaaagaca ccagagtgcg caatagccca    3540
ccccacagtg ggctaacagc catggggccg gtccccacac cgatccgggg cgccttcacg    3600
accgcaggcg tggttctgga gatgatcaag gacgtggagg ctgcggtctc aggccgcaag    3660
ggcaggagcg gcacgcggc gggcgacgtc gccttcccca aggggaagga gaacctggcc    3720
tccgtgctga gcggtacaa gcggcggctc gccagcaagg gccag                     3765
```

<210> SEQ ID NO 42
<211> LENGTH: 1255
<212> TYPE: PRT

<213> ORGANISM: Zea mays
<220> FEATURE:
<223> OTHER INFORMATION: Zea mays ethylene receptor (ethylene
      insensitive receptor, EIN2-like), E2-25 protein

<400> SEQUENCE: 42

```
Met Asp Ala Pro Asp Val Gln Gln Ser Met Gly Tyr Lys Glu Ser Arg
 1               5                  10                  15

Gly Gly Met Pro Lys Phe Phe His Ala Leu Gly Pro Ala Leu Leu Ile
            20                  25                  30

Ser Met Gly Tyr Ile Asp Leu Gly Lys Trp Val Ala Ala Val Glu Ala
        35                  40                  45

Gly Ser Cys Phe Gly Phe Asp Leu Val Leu Ala Leu Leu Phe Asn
    50                  55                  60

Phe Thr Ala Ile Val Cys Gln Tyr Leu Ala Ala Cys Ile Gly Thr Val
 65                  70                  75                  80

Thr Gly Lys Asn Leu Ala Glu Ile Cys His Gln Glu Tyr Asn Gln Pro
                85                  90                  95

Thr Cys Ile Phe Leu Gly Val Gln Ala Gly Leu Ser Leu Leu Thr Ser
            100                 105                 110

Glu Leu Ser Met Ile Phe Gly Ile Ala Leu Gly Phe Asn Leu Leu Phe
        115                 120                 125

Glu Tyr Asp Asp Leu Ile Thr Gly Ile Cys Phe Ala Thr Val Met Glu
    130                 135                 140

Gly Thr Ile Asn Ala Cys Ile Ala Gly Phe Ala Leu Leu Ser Tyr Val
145                 150                 155                 160

Leu Gly Leu Leu Val Ser Gln Pro Gln Ile Pro Leu Thr Met Asn Val
                165                 170                 175

Ile Phe Pro Lys Ile Ser Gly Glu Ser Ala Tyr Ser Leu Met Ala Leu
            180                 185                 190

Leu Gly Ala Asn Ile Met Ala His Asn Phe Tyr Ile His Ser Ser Gly
        195                 200                 205

Gln Lys Lys Ser Ser Ala Val Gly Leu Gly Ala Leu Phe His Asp His
    210                 215                 220

Leu Phe Ser Ile Leu Phe Ile Phe Thr Gly Ile Phe Met Val Asn Tyr
225                 230                 235                 240

Val Leu Met Asn Ser Ala Ala Ala Glu Ser Thr Asn Thr Leu Leu Ile
                245                 250                 255

Thr Phe Gln Asp Val Val Glu Leu Met Asn Gln Ile Phe Val Asn Pro
            260                 265                 270

Leu Ala Pro Thr Ile Phe Leu Val Val Leu Leu Phe Ser Ser His Ile
        275                 280                 285

Ile Ser Leu Thr Ser Ala Ile Gly Ser Gln Val Ile Ser His His Leu
    290                 295                 300

Phe Gly Ile Asn Leu Pro Leu Ser Gly His Arg Leu Leu Lys Val
305                 310                 315                 320

Phe Ala Ile Val Pro Thr Leu Tyr Trp Ala Lys Val Ala Gly Ala Glu
                325                 330                 335

Gly Ile Tyr Gln Leu Ile Ile Cys Gln Ile Ile Gln Ala Met Leu
            340                 345                 350

Leu Pro Ser Ser Val Val Pro Leu Phe Arg Val Ala Ser Ser Arg Ser
        355                 360                 365

Ile Met Gly Ala His Arg Val Ser Leu His Leu Glu Ile Leu Val Phe
    370                 375                 380

Leu Ala Phe Leu Leu Met Leu Phe Ser Asn Ile Ile Phe Val Ala Glu
```

```
            385                 390                 395                 400
Met Leu Phe Gly Asp Ser Gly Trp Met Asn Asn Leu Lys Gly Tyr Thr
                    405                 410                 415
Gly Ser Pro Val Val Leu Pro Tyr Thr Val Leu Val Leu Val Ala Leu
                420                 425                 430
Ile Ser Val Ala Phe Ser Leu Tyr Leu Ala Val Thr Pro Leu Arg Ser
            435                 440                 445
Gly Ser His Glu Ala Glu Ser His Glu Trp Ser Val His Ser Gln Arg
        450                 455                 460
Glu Leu Leu Asn Thr Ser Gln Glu Arg Glu Asp Val Lys Val Asp Asn
465                 470                 475                 480
Val Thr Tyr Glu Glu Asp Gln Arg Ser Asp Val Val Pro Ser Pro Arg
                485                 490                 495
Asp Val Pro Asp Ser His Pro Glu Leu Ala Leu Asp Tyr Ile Asp Thr
            500                 505                 510
Ser Asp Thr Ala Val Glu Ser Asp His Asp Ser Gln Gln Ser Thr Ala
        515                 520                 525
Tyr Ala Ser Thr Ala Pro Glu Thr Cys Ser Ser Pro Ser Phe Thr Arg
    530                 535                 540
Glu Glu Ser Lys Ser Val Val Ala Val Asn Trp Pro Glu Pro Leu Glu
545                 550                 555                 560
Lys Val Pro Thr Ser Thr Val Met Glu Glu Ser Thr Val Glu Asn Val
                565                 570                 575
Val Ser Arg Ile Thr Thr Glu Arg Asp Val Leu Val Gly Thr Asp Val
            580                 585                 590
Val Ser Gly Lys Asp Lys Glu Asp Ile Arg Thr Leu Glu Ser Glu Lys
        595                 600                 605
Ser Ile Val Asp Ser Thr Pro Tyr Val Ser Asp Gly Pro Pro Ser
    610                 615                 620
Leu Thr Phe Ser Arg Gly Lys Gly Ser Asp Ala Gly Asn Gly Ser Gly
625                 630                 635                 640
Ser Leu Ser Arg Leu Ser Gly Leu Gly Arg Ala Ala Arg Arg Gln Leu
                645                 650                 655
Ala Ala Thr Leu Asp Glu Phe Trp Gly His Leu Phe Asp Tyr His Gly
                660                 665                 670
Lys Leu Thr Gln Glu Ala Ser Thr Lys Lys Phe Gly Ile Leu Leu Gly
            675                 680                 685
Ile Asp Leu Arg Thr Pro Ser Thr Ser Val Arg Thr Asp Lys Gln Ala
        690                 695                 700
Ala Glu Ile Leu Lys Ser Pro Leu Val Arg Asp Ser Met Arg Gly Ala
705                 710                 715                 720
Ala Phe Leu Ser Ser Ser Val Asp Met Met Ser Pro Lys Asn Glu Thr
                725                 730                 735
Ser Asn Leu Glu Leu Ala Tyr Gly Leu Gln Arg Gly Pro Gly Met Gly
            740                 745                 750
Leu Ser Ser Trp Ser Gln Gly Met Gln Leu Pro Asn Thr Gln Leu Gln
        755                 760                 765
Ser Ser Ser Asn Ser Leu Leu Glu Gln Ser Ala Arg Leu Asn Ser Asn
    770                 775                 780
Phe Ser Ser Ser Tyr Ser Asp Asn Asn Gln Phe Tyr Gln Pro Ala Thr
785                 790                 795                 800
Ile His Gly Tyr Gln Leu Thr Ser Tyr Leu Lys Gln Met Asn Ala Ser
                805                 810                 815
```

-continued

```
Pro Ser Leu Tyr Ser Ser Met Pro Leu Asp Pro Gln Arg Leu Pro Lys
            820                 825                 830

Ser Ser Val Ser Ala Val Pro Asn Tyr Ala Asp Ser Met Met His Ala
        835                 840                 845

Arg Asn His Asn Leu Leu Ala Ser Leu Gly Gly Thr Thr Thr Gln Leu
    850                 855                 860

Pro Ala Thr Ser Arg Val Gly Ser Met Met Pro Glu Arg Ser Tyr Tyr
865                 870                 875                 880

Asp Pro Ser Ser Val Asp Gly Asn Glu Asn Ala Gly Ser Pro Ala Tyr
                885                 890                 895

Ser Lys Lys Tyr His Ser Ser Pro Asp Met Ser Gly Ile Ile Ala Ala
            900                 905                 910

Ser Arg Ala Ala Leu Leu Asn Glu Ala Lys Leu Gly Ala Ala Ile Gly
        915                 920                 925

Pro Gln Ser Tyr Leu Ser Arg Leu Ala Ala Glu Arg Ser Gln Tyr Ala
    930                 935                 940

Ser Ser Thr Ala Arg Pro Ala Ala Pro Leu Ala Phe Asp Glu Leu Ser
945                 950                 955                 960

Pro Pro Lys Leu Gln Ser Asp Ile Phe Ser Ala Gln Ser Ser Met Arg
                965                 970                 975

Pro Ser Ala Arg Ser Leu Trp Ala Lys Gln Pro Phe Glu Gln Leu Phe
            980                 985                 990

Gly Met Ser Ser Ala Glu Leu Ser Lys Gly Asp Phe Asn Leu Pro Gly
        995                 1000                1005

Arg Ser Gly Gly Val Ala Lys Asp Asp Phe Ser Tyr Lys Glu Ser Glu
    1010                1015                1020

Thr Lys Leu Leu Gln Ser Leu Arg Leu Cys Ile Met Lys Leu Leu Lys
1025                1030                1035                1040

Leu Glu Gly Ser Gly Trp Leu Phe Lys Gln Asn Gly Gly Cys Asp Glu
                1045                1050                1055

Asp Leu Ile Asp Arg Val Ala Ala Ala Glu Lys Leu Leu Met Gln Gly
            1060                1065                1070

Thr Ala Glu Asn Gln Leu Leu Leu His Gly Gly Asp Leu Gln Gln His
        1075                1080                1085

Ser Ser Asp Gln Ala Gly Ile Gln Tyr Met Arg Thr Leu Pro Asn Cys
    1090                1095                1100

Gly Glu Asp Cys Val Trp Arg Ala Ser Leu Val Val Ser Phe Gly Val
1105                1110                1115                1120

Trp Cys Val Arg Arg Val Leu Asp Met Ser Leu Val Glu Ser Arg Pro
                1125                1130                1135

Glu Leu Trp Gly Lys Tyr Thr Tyr Val Leu Asn Arg Leu Gln Gly Ile
            1140                1145                1150

Leu Asp Pro Ala Phe Ser Lys Pro Arg Gly Ala Leu Thr Ile Cys Thr
        1155                1160                1165

Cys Leu Gln Lys Asp Thr Arg Val Arg Asn Ser Pro Pro His Ser Gly
    1170                1175                1180

Leu Thr Ala Met Gly Pro Val Pro Thr Pro Ile Arg Gly Ala Phe Thr
1185                1190                1195                1200

Thr Ala Gly Val Val Leu Glu Met Ile Lys Asp Val Glu Ala Ala Val
                1205                1210                1215

Ser Gly Arg Lys Gly Arg Ser Gly Thr Ala Ala Gly Asp Val Ala Phe
            1220                1225                1230

Pro Lys Gly Lys Glu Asn Leu Ala Ser Val Leu Lys Arg Tyr Lys Arg
        1235                1240                1245
```

Arg Leu Ala Ser Lys Gly Gln
　　1250　　　　　　　　1255

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN2-like, ZmEIN2-25) E2-25 forward primer

<400> SEQUENCE: 43
tgggtggtac tactacacag cttcct                                          26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN2-like, ZmEIN2-25) E2-25 reverse primer

<400> SEQUENCE: 44
aggcttggag aacgcagggt ccaaga                                          26

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN3-like, ZmEIN3-2) EIN3-2 forward primer

<400> SEQUENCE: 45 accccccgtac aagaagcctc atga                                           24

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN3-like, ZmEIN3-2) EIN3-2 reverse primer

<400> SEQUENCE: 46
gtttatggct ggccggacat acaagt                                          26

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:Zea mays
      ethylene receptor (ethylene insensitive receptor,
      EIN3-like, ZmEIN3-3) EIN3-3 forward primer

<400> SEQUENCE: 47 accccccgtac aagaagcctc atga                                           24

<210> SEQ ID NO 48
<211> LENGTH: 29
<212> TYPE: DNA
<213> ORGANISM: Artificial Sequence
<220> FEATURE:

-continued

```
<223> OTHER INFORMATION: Description of Artificial Sequence:Zea mays
      ethylene receptor (ethylene insensitive receptor,
      EIN3-like, ZmEIN3-3) EIN3-3 reverse primer

<400> SEQUENCE: 48
acgaccaaga ccctatagac tcgacactc                                      29

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:
      oligo-dT(20) primer

<400> SEQUENCE: 49
tttttttttt tttttttttt                                                20

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence:
      ACOR1 primer

<400> SEQUENCE: 50
cctcgaaccg tggctccttg gcctcgaact t                                   31
```

MAIZE ETR2 GENE AND USES THEREOF

CROSS-REFERENCES TO RELATED APPLICATIONS

This application is a divisional application of U.S. patent application Ser. No. 10/876,086, filed Jun. 23, 2004, which has issued as U.S. Pat. No. 7,504,557, which claims the benefit of U.S. Provisional Application No. 60/480,960, filed Jun. 23, 2003. Each of the aforementioned applications are incorporated by reference herein.

FIELD OF THE INVENTION

The present invention is directed to plant genetic engineering. In particular, it is directed to producing green leaves in maize through inhibition of ethylene. The genes involved in producing this phenotype include 1-Aminocyclopropane-1-Carboxylate ("ACC") oxidase, ACC deaminase, ethylene response sensor ("ERS"), ethylene resistant ("ETR"), and ethylene insensitive ("EIN").

BACKGROUND OF THE INVENTION

Programmed cell death (PCD) is integral to the development of multicellular organisms including plants. Numerous reports of plant PCD have appeared in the literature in the last 5 years and include examples that occur as part of the response to pathogen attack: e.g., the hypersensitive response (reviewed in Greenberg, et al., *Proc. Natl. Acad. Sci. USA* 93:12094-12097 (1996); Pennell and Lamb, et al., *Plant Cell* 9:1157-1168 (1997); Richberg et al., *Curr. Op. Biol.* 1:480-485 (1998); Lam et al., *Curr. Op. Biol.* 2:502-507 (1999)); the response to abiotic stress: e.g., formation of aerenchyma in hypoxic roots (reviewed in Drew, *Annu. Rev. Plant Physiol. Plant Mol. Biol.* 48:223-250 (1997); Drew et al., *Trends Plant Sci.* 5:123-127 (2000)); or as part of a normal developmental program: e.g., endosperm cell death during tracheary differentiation (Fukuda, *Plant Cell* 9:1147-1156 (1997); Groover and Jones, *Plant Physiol.* 119:375-384 (1999)), cereal seed development (Young et al., *Plant Physiol.* 119:737-751 (1997); Young and Gallie, *Plant Mol. Biol.* 39:915-926 (1999); Young and Gallie, *Plant Mol. Biol.* 42:397-414 (2000)), or aleurone cell death during late cereal seed germination (Kuo et al., *Plant Cell* 8:259-269 (1996); Bethke et al., *Plant Cell* 11:1033-1045 (1999); Wang et al., *Plant Mol. Biol.* 32:1125-1134 (1996)). During maize kernel development, the endosperm undergoes a progressive cell death that engulfs the entire tissue, leaving only the aleurone layer viable at maturity (Bartels et al., *Planta* 175:485-492 (1988); Kowles and Phillips, *Int. Rev. Cytol.* 112:97-136 (1988); Lopes and Larkins, *Plant Cell* 5:1383-1399 (1993); Young et al., *Plant Physiol.* 119:737-751 (1997); Young and Gallie, *Plant Mol. Biol.* 39:915-926 (1999)).

Ethylene is known to be a regulator of PCD during plant development (Campbell and Drew, *Planta* 157:350-357 (1983); Drew et al., *Planta* 147:83-88 (1979); He et al., *Plant Physiol.* 112:1679-1685 (1996)) and plays a role in orchestrating programmed cell death in developing cereal endosperm: exogenous ethylene can accelerate the onset of the cell death program in developing endosperm whereas inhibitors of ethylene biosynthesis or perception delay the program (Young et al., *Plant Physiol.* 119:737-751 (1997); Young and Gallie, *Plant Mol. Biol.* 39:915-926 (1999); Young and Gallie, *Plant Mol. Biol.* 42:397-414 (2000)). Ethylene controls many aspects of plant growth and development such as fruit development, root and leaf growth and seed germination. Ethylene is generated from methionine by conversion of S-adenosyl-L-methionine to the cyclic amino acid 1-aminocyclopropane-1-carboxylic acid (ACC) which is facilitated by ACC synthase (Yang and Hoffman, *Annu. Rev. Plant Physiol.* 35:155-189 (1984)). Ethylene ($C_2H_4$) is then produced from the oxidation of ACC through the action of ACC oxidase. ACC synthase and ACC oxidase are encoded by multigene families in which individual members exhibit tissue-specific regulation and/or are induced in response to environmental and chemical stimuli. (reviewed in Fluhr and Mattoo, *Crit. Rev. Plant Sci.* 15: 479-523 (1996); Kende, *Annu. Rev. Plant Physiol.* 44:283-307 (1993); Zarembinski and Theologis, *Plant Mol. Biol.* 26:1579-1597 (1994)).

Enzymes that degrade the compounds produced by the ethylene biosynthesis pathway are also known. Two enzymes in particular, ACC deaminase and ACC malonyl transferase, are commonly found in bacteria and can lower the concentration of ACC in the cell. ACC deaminase accomplishes this by converting ACC to α-ketobutyrate and ammonia. Nucleic acids encoding this enzyme have been used to control fruit ripening in plants (U.S. Pat. No. 5,702,933). Endogenous ACC concentration is also lowered by forming the metabolically inert compound, N-malonyl-ACC, in a reaction catalyzed by ACC N-malonyltransferase (MTase). (Liu et al., *Phytochemistry* 40:691-697 (1995)).

Ethylene perception involves membrane-localized receptors that, in *Arabidopsis*, include ETR1, ERS1, ETR2, ERS2 and EIN4 (Chang et al., *Science* 262:539-544 (1993); Hua et al., *Science* 269:1712-1714 (1995), Hua et al., *Plant Cell* 10:1321-1332 (1998), Sakai et al., *Proc. Natl. Acad. Sci. USA* 95:5812-5817 (1998)). ETR1, ETR2 and EIN4 are composed of three domains, an N-terminal ethylene binding domain (Schaller and Bleeker, *Science* 270:1809-1811 (1995)), a putative histidine protein kinase domain, and a C-terminal received domain whereas ERS1 and ERS2 lack the receiver domain. These genes have been grouped into two subfamilies based on homology, where ETR1 and ERS1 comprise one subfamily and ETR2, ERS2, and EIN4 comprise the other (Hua et al., *Plant Cell* 10:1321-1332 (1998)). These receptors exhibit sequence similarity to bacterial two-component regulators (Chang et al., *Science* 262:539-544 (1993)) which act as sensors and transducers of environmental signals (Parkinson and Kofoid, *Annu. Rev. Genet.* 26:71-112 (1992)) and as sensors in yeast and *Dictyostelium* that are involved in osmotic regulation (Maeda et al., *Nature* 369:242-245 (1994); Schuster et al., *EMBO J.* 15:3880-3889 (1996)).

In *Arabidopsis*, analysis of loss-of-function mutants has revealed that ethylene inhibits the signaling activity of these receptors and subsequently their ability to activate CTR1, a negative regulator of ethylene responses that is related to mammalian RAF-type serine/threonine kinases (Kieber et al., *Cell* 72:427-441 (1993)). Current understanding of the ethylene signal transduction pathway suggests that ethylene binding to the receptor inhibits its own kinase activity, resulting in decreased activity of CTR1, and consequently, an increase in EIN2 activity (which acts downstream of CTR1) that ultimately leads to an increase in ethylene responsiveness (Bleeker and Schaller, *Plant Physiol.* 111:653-660 (1996); Hua and Meyerowitz, *Cell* 72:427-441 (1998)). Differential expression of members of the ethylene receptor family has been observed, both developmentally and in response to ethylene (Hua et al., *Plant Cell* 10:1321-1332 (1998); Lashbrook et al., *The Plant J.* 15:243-252 (1998)).

Because ethylene plays such a large role in plant growth and development, the identification of genes involved in the ethylene synthesis pathway is useful for creating plants with phenotypes associated with an altered ethylene-related process, such as plants having staygreen traits. The synthesis of ethylene, its perception by ethylene receptors, and its downstream signaling components have been identified in *Arabidopsis* and some other plant species. Prior to the advent of the present invention, however, no maize gene involved in ethylene bioysnthesis or signal transduction had been reported. Accordingly, a need exists for the identification of genes involved in the maize ethylene biosynthesis and signal transduction pathways. This invention meets this and other needs by providing, ACC oxidase, ACC deaminase, ERS1, ETR2, and EIN2 as well as methods of their use.

BRIEF SUMMARY OF THE INVENTION

The present invention provides compositions and methods which affect ethylene biosynthesis or the signal transduction pathway of ethylene in plants.

In a first aspect, the invention provides for an isolated nucleic acid which can encode a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41) wherein the isolated nucleic acid is at least 90% identical to the polynucleotide sequence.

In a second aspect, the invention provides a recombinant expression cassette comprising a promoter sequence operably linked to a nucleic acid sequence encoding a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41), wherein the isolated nucleic acid is at least 90% identical to the polynucleotide sequence or a fragment thereof.

In a third aspect, the invention provides a transgenic plant comprising a recombinant expression cassette comprising a promoter sequence operably linked to a nucleic acid sequence encoding a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41), wherein the isolated nucleic acid is at least 90% identical to the polynucleotide sequence or a fragment thereof.

In a fourth aspect, the invention provides a method of inhibiting ACC oxidase, or EIN2 activity in a plant, the method comprising introducing a construct comprising a promoter operably linked to a nucleic acid sequence encoding a polynucleotide sequence such as ACC oxidase (represented by SEQ ID NOs: 2, 7, 11, and 16), or EIN2 (represented by SEQ ID NO: 41) wherein the isolated nucleic acid is at least 90% identical to the polynucleotide sequence or a fragment thereof.

In a fifth aspect, the invention provides a method of increasing ACC deaminase, ERS, or ETR activity in a plant, the method comprising introducing a construct comprising a promoter operably linked to a nucleic acid sequence encoding a polynucleotide sequence such as ACC deaminase, ERS (represented by SEQ ID NOs: 21 and 26), or ETR (represented by SEQ ID NOs: 31 and 36) wherein the isolated nucleic acid is at least 90% identical to the polynucleotide sequence or a fragment thereof.

Other objects, advantages and embodiments of the invention will be apparent from review of the Detailed Description that follows.

BRIEF DESCRIPTION OF THE DRAWINGS

NOT APPLICABLE

DETAILED DESCRIPTION OF THE INVENTION

A. Introduction

The present invention provides new methods of delaying senescence in a maize plant by inhibiting ACC oxidase, or EIN2 activity in the plant. The delay in senescence can also be achieved through the production of ACC deaminase, mutated ETR1 and ERS2 proteins, as well as overexpression of wild-type ETR1 and ERS2 proteins. The present invention also provides methods for selecting for a maize plant with a delayed senescence pattern or characteristic. A delayed senescence pattern will result in a maize plant with an altered phenotype as compared to a wild type plant. An altered phenotype includes, but is not limited to, staygreen traits, e.g., leaves that remain green late in the growing season, improved drought tolerance, improved silage, increased grain yield, and increased tolerance to planting at higher densities, and kernels with multiple embryos. Accordingly, by inhibiting ACC oxidase, or EIN2 activity in a plant, or through the production of ACC deaminase, mutated ETR1 and ERS2 proteins, as well as overexpression of wild-type ETR1 and ERS2 proteins, a plant with increased biomass and/or yield can be identified.

B. Definitions

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read through by a polymerase and do not alter the expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid and hemizygous.

The phrase "host cell" refers to a cell from any organism. Preferred host cells are derived from plants, bacteria, yeast, fungi, insects or other animals. Methods for introducing polynucleotide sequences into various types of host cells are well known in the art.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like.

An "ACC oxidase polynucleotide" is a nucleic acid sequence comprising a coding region of about 50 to about 6800 nucleotides, sometimes from about 100 to about 3000 nucleotides and sometimes from about 300 to about 1300 nucleotides, which hybridizes to SEQ ID NOs: 2, 7, 12, and 17 under stringent conditions (as defined below), which comprises at least 20, typically 50, contiguous nucleotides of these sequences, or which encodes an ACC oxidase polypeptide or fragment of at least 15 contiguous amino acids thereof. ACC oxidase polynucleotides are typically at least about 90% identical to the exemplified seqeunces.

An "ACC oxidase polypeptide" or "ACC oxidase protein" has a sequence of about 50 to about 400, sometimes 100 to 150, and preferably between 310 and 330 amino acid residues encoded by an ACC oxidase polynucleotide. ACC oxidase polypeptides are involved in ethylene biosynthesis and are exemplified by SEQ ID NOs: 3, 8, 12, and 17.

An "ERS1 polynucleotide" is a nucleic acid sequence comprising a coding region of about 50 to about 4000 nucleotides, sometimes from about 1000 to about 3000 nucleotides and sometimes from about 1600 to about 2000 nucleotides, which hybridizes to SEQ ID NOs: 21 or 26 under stringent conditions (as defined below), which comprises at least 20, typically 50, contiguous nucleotides of these sequences, or which encodes an ERS1 polypeptide or fragment of at least 15 contiguous amino acids thereof. ERS1 polynucleotides are typically at least about 90% identical to the exemplified seqeunces.

An "ERS1 polypeptide" or "ERS1 protein" has a sequence of about 75 to about 1000, sometimes 200 to 700, and preferably 634 amino acid residues encoded by an ERS1 polynucleotide. ERS1 polypeptides are involved in ethylene biosynthesis and are exemplified by SEQ ID NOs: 22 and 27.

An "ETR2 polynucleotide" is a nucleic acid sequence comprising a coding region of about 50 to about 6800 nucleotides, sometimes from about 1000 to about 3000 nucleotides and sometimes from about 2200 to about 2400 nucleotides, which hybridizes to SEQ ID NOs: 31 or 36 under stringent conditions (as defined below), which comprises at least 20, typically 50, contiguous nucleotides of these sequences, or which encodes an ETR2 polypeptide or fragment of at least 15 contiguous amino acids thereof. ETR2 polynucleotides are typically at least about 90% identical to the exemplified seqeunces.

An "ETR2 polypeptide" or "ETR2 protein" has a sequence of about 100 to about 900, sometimes 300 to 800, and preferably between 765 and 770 amino acid residues encoded by an ETR2 polynucleotide. ETR2 polypeptides are involved in ethylene biosynthesis and are exemplified by SEQ ID NOs: 32 and 37.

An "EIN2 polynucleotide" is a nucleic acid sequence comprising a coding region of about 1000 to about 9000 nucleotides, sometimes from about 5000 to about 8500 nucleotides and sometimes from about 8100 to about 8400 nucleotides, which hybridizes to SEQ ID NO: 42 under stringent conditions (as defined below), which comprises at least 20, typically 50, contiguous nucleotides of these sequences, or which encodes an EIN2 polypeptide or fragment of at least 15 contiguous amino acids thereof. EIN2 polynucleotides are typically at least about 90% identical to the exemplified seqeunces.

An "EIN2 polypeptide" or "EIN2 protein" has a sequence of about 50 to about 1500, sometimes 500 to 1400, and preferably 1255 amino acid residues encoded by an EIN2 polynucleotide. EIN2 polypeptides are involved in ethylene biosynthesis and are exemplified by SEQ ID NO: 42.

"Increased or enhanced expression or activity" of a particular polypeptide or nucleic acid of the invention refers to an augmented change in activity of the polypeptide. Examples of such increased activity or expression include the following: Activity of the polypeptide or expression of the gene encoding the polypeptide is increased above the level (or is present for a loner period of time) of that in wild-type, non-transgenic control plants. Activity of a polypeptide or expression of a gene is present in an organ, tissue or cell where it is not normally detected in wild-type, non-transgenic control plants (i.e. spatial distribution of a polypeptide or expression of the gene encoding the polypeptide is altered).

"Decreased expression or activity" of a polypeptide or nucleic acid of the invention refers to a decrease in activity of the polypeptide. Examples of such decreased activity or expression include the following: Activity of the polypeptide or expression of the gene is decreased below the level of that in a wild-type, non-transgenic control plant.

The term "reproductive structures" or "reproductive tissues" as used herein includes fruit, ovules, seeds, pollen, flowers, or flower parts such as pistils, stamens, anthers, sepals, petals, carpels, or any embryonic tissue.

The term "vegetative structures" or "vegetative tissues" as used herein includes leaves, stems, tubers, roots, vascular tissue, or root and shoot meristem.

An "expression cassette" refers to a nucleic acid construct, which when introduced into a host cell, results in transcription and/or translation of a RNA or polypeptide, respectively. Antisense or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy, a number of polynucleotide sequences will encode the same polypeptide. These variants are specifically covered by the term "polynucleotide sequence from a gene of the invention". In addition, the term specifically includes sequences (e.g., full length sequences) substantially identical (determined as described below) with a gene sequence encoding an peptide of the invention, and that encode proteins that retain the function of a peptide of the invention.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman, *Add. APL. Math.* 2:482 (1981), by the homology alignment algorithm of Needle man and Wunsch, *J. Mol. Biol.* 48:443 (1970), by the search for similarity method of Pearson and Lipman, *Proc. Natl. Acad. Sci. U.S.A.* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 85% sequence identity. Alternatively, percent identity can be any integer from 85% to 100%. More preferred embodiments include at least: 85%, 90%, 95%, or 99%. compared to a reference sequence using the programs described herein; preferably BLAST using standard parameters, as described below. Accordingly, sequences encoding a polypeptide used in the methods of the present invention include nucleic acid sequences that have substantial identity to the sequences disclosed here. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 90%. Preferred percent identity of polypeptides can be any integer from 90% to 100%. More preferred embodiments include at least 90%, 95%, or 99%. Polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. or 65° C.

For the purposes of this disclosure, stringent conditions for hybridizations are those which include at least one wash in 0.2×SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions.

The phrase "phenotype associated with an ethylene-related process" refers to a phenotype that is modulated by ethylene. Exemplary phenotypes include, but are not limited to, staygreen traits, such as improved drought tolerance, improved silage, leaves that stay green later in the season, and increased tolerance to planting at higher densities. Modulation of ethylene-related processes can result from, e.g., overproduction of ethylene, underproduction of ethylene, increased sensitivity to ethylene in a cell or decreased sensitivity to ethylene in a cell.

The term "staygreen" refers to the ability of a hybrid plant to maintain plant health later into the growing season as compared to a wild type plant. Staygreen traits have been associated with increased grain yield, improved drought tolerance, improved silage and an increase in tolerance to planting at higher densities.

C. Isolation of Nucleic Acids used in the Present Invention

The invention provides for an isolated nucleic acid which can encode a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41) wherein the isolated nucleic acid is at least 90% identical to the polynucleotide sequence. In an exemplary embodiment, the polynucleotide sequence is selected from the group consisting of SEQ ID NOs: 2, 7, 11, 16, 21, 26, 31, 36 and 41.

The isolation of nucleic acids used in the present invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of embryo-specific cDNAs, mRNA is isolated from embryos and a cDNA library that contains the gene transcripts is prepared from the mRNA.

The cDNA or genomic library can then be screened using a probe based upon the sequence of a cloned embryo-specific gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes encoding polypeptides of the invention from plant tissues are generated from comparisons of the sequences provided herein. For a general overview of PCR see PCR Protocols: A Guide to Methods and Applications. (Innis, M., Gelfand, D., Sninsky, J. and White, T., eds.), Academic Press, San Diego (1990). For example, appropriate primers for amplification of the genomic region of ACC oxidase include the following primer pairs: SEQ ID NO: 4 and SEQ ID NO: 5. The other primers disclosed here also are conveniently used by one of skill to prepare of the nucleic acids of the invention. The amplification conditions are typically as follows. Reaction components: 10 mM Tris HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per mL Taq polymerase. Program: 96° C. for 3 min., 30 cycles of 96° C. for 45 sec., 50° C. for 60 sec., 72° C. for 60 sec., followed by 72° C. for 5 min.

Polynucleotides may also be synthesized by well-known techniques as described in the technical literature. See, e.g., Carruthers et al., *Cold Spring Harbor Symp. Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

The genus of sequences of the present invention include genes and gene products identified and characterized by analysis using the nucleic acid sequences, including SEQ ID NOs: 1-2, 6-7, 11, 15-16, 20-21, 25-26, 30-31, 35-36, and 40-41, and protein sequences, including SEQ ID NOs: 3, 8, 12, 17, 22, 27, 32, 37, and 42. Sequences encoding the polynucleotides used in the present invention include nucleic acid sequences having substantial identity to SEQ ID NOs: 1-2, 6-7, 11, 15-16, 20-21, 25-26, 30-31, 35-36, and 40-41. Sequences encoding the polypeptides used in the present invention include polypeptide sequences having substantial identity to SEQ ID NOs: 3, 8, 12, 17, 22, 27, 32, 37, and 42.

Once a nucleic acid is isolated using the method described above, standard methods can be used to determine if the nucleic acid encodes ACC oxidase, ERS, ETR, or EIN2 polypeptides. A nucleic acid that encodes a polypeptide of the invention can be used to create a transgenic plant having staygreen traits. A transgenic plant having enhanced or increased expression to, for example, ACC oxidase polypeptide identical or substantially identical to SEQ ID NOs: 3, 8, 12, or 17 will display a phenotype associated with an altered ethylene process within the plant, e.g., delayed senescence.

Using standard methods, the skilled practitioner can compare the sequence of a putative nucleic acid sequence thought to encode, for example, an ACC oxidase polypeptide to a nucleic acid sequence encoding an ACC oxidase polypeptide to determine if the putative nucleic acid encodes an actual ACC oxidase polypeptide. A nucleic acid that encodes an ACC oxidase polypeptide, e.g., nucleic acids comprising sequences identical or substantially identical to SEQ ID NOs: 1-2, 6-7, 11, 15-16 can be used in the methods of the present invention.

D. Enhancing Expression of the Peptides of the Invention

Using specified promoters, the skilled practitioner can direct the expression of an ACC oxidase, ACC deaminase, ERS, ETR, or EIN2 peptide and create a plant with desirable phenotypic characteristics, e.g., staygreen traits. The skilled practitioner can choose from a variety of known promoters, whether constitutive, inducible, tissue-specific, and the like to drive expression of the gene encoding an ACC oxidase, ACC deaminase, ERS, ETR, or EIN2 peptide.

Any phenotypic characteristic caused by alteration of an ethylene-related process in a plant can be selected for in the present invention. For example, after introducing a polynucleotide encoding an ACC oxidase polypeptide, operably linked to a desirable promoter, e.g., constitutive, tissue specific, or inducible, in a plant, and regenerating the plant by standard procedures, a skilled practitioner can use standard methods to determine if the transgenic plant is a transgenic plant of the present invention, e.g., by comparing the transgenic plant to a wild type plant and looking for a phenotype associated with an altered ethylene-related process.

Enhancing or increasing expression of endogenous genes encoding enzymes involved in the ethylene biosynthesis pathway such as ACC oxidase may modulate an ethylene-related process in a plant by a variety of pathways. Alternatively, heterologous genes, such as ACC deaminase can be used. The particular pathway used to modulate an ethylene-related process is not critical to the present invention. For example, overexpression of an ACC oxidase polypeptide in a plant may affect ethylene-related processes by increasing ethylene levels in a plant and increasing sensitivity to ethylene in a plant.

Enhancing or increasing expression of genes encoding enzymes involved in ethylene signal transduction such as ERS, ETR, or EIN2 may also modulate an ethylene-related process in a plant by a variety of pathways. For example, increased expression of wild-type ERS or ETR subunits can increase the population of active ERS and ETR receptors in the plant cell and therefore inhibit ethylene detection and prevent the onset of senescence. In another example, enhancing the expression of genes encoding dominant negative mutations in ERS and ETR subunits can inhibit ethylene detection and prevent the onset of senescence.

Any number of means well known in the art can be used to modulate activity of an ACC oxidase, ERS, ETR, or EIN2 peptide in a plant. For example, the sequences, as described herein, can be used to prepare expression cassettes that enhance or increase endogenous gene expression. Where overexpression of a gene is desired, the desired gene from a different species may be used to decrease potential sense suppression effects. For example, enhanced expression of polynucleotides encoding ERS or ETR peptides are useful, for example, in order to increase the population of ERS or ETR receptors on the cell surface which will correspondingly lead to an increase in staygreen traits.

Any organ can be targeted for overexpression of a peptide of the invention such as shoot vegetative organs/structures (e.g., leaves, stems, and tubers), roots, flowers, and floral or reproductive organs/structures (e.g., bracts, sepals, petals, stamens, carpels, anthers and ovules), seed (including embryo, endosperm, and seed coat) and fruit. Vascular or provascular tissues may be targeted. Alternatively, one or several genes described in the present invention may be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed.

E. Inhibiting Expression of the Peptides of the Invention

In some embodiments of the present invention, ethylene-related processes are modulated by inhibiting gene expression in a plant. As noted above, the invention provides a method of inhibiting ACC oxidase, or EIN2 activity in a plant, the method comprising introducing a construct comprising a promoter operably linked to a nucleic acid sequence encoding a polynucleotide sequence such as ACC oxidase (represented by SEQ ID NOs: 2, 7, 11, and 16), or EIN2 (represented by SEQ ID NO: 41) wherein the isolated nucleic acid is at least 90% identical to the polynucleotide sequence.

For example, expression cassettes of the invention can be used to suppress endogenous expression of genes encoding an ACC oxidase protein. For example, in some embodiments, the present invention provides methods of delaying senescence in a plant by decreasing expression of a gene encoding an ACC oxidase polypeptide in a plant. A plant with delayed senescence possesses phenotypic characteristics that are recognizable to the skilled practitioner, e.g., abnormal developmental patterns such as the presence of staygreen traits. The affected plant part can be a reproductive plant part or vegetative plant part. For example, the plant part may include leaves, but can also include fruit, ovules, seeds, pollen, embryonic tissue, flowers, flower parts such as pistils, stamens, sepals, petals, carpels, stems, tubers, roots, vascular tissue, provascular tissue or root or stem meristem. For example, in some embodiments of the present invention, a tissue specific promoter, such as a seed specific promoter, can be used to create a transgenic plant with altered seed characteristics as compared to a wild type plant. A plant with altered seed characteristics, for example, may have greater seed yield.

A number of methods can be used to inhibit gene expression in a plant. The ability to inhibit gene function in a variety of organisms using double stranded RNA (also referred to as RNAi) is well known (Ding, *Current Opinions in Biotechnology* 1:152-156 (2000)). Expression cassettes encoding RNAi typically comprise a polynucleotide sequence at least substantially identical to the target gene linked to a complementary polynucleotide sequence. The sequence and its complement are often connected through a linker sequence that allows the transcribed RNA molecule to fold over such that the two sequences hybridize to each other. RNAi has been shown to inhibit genetic function in plants (see Chuang et al., *Proc. Natl. Acad. Sci. USA* 97:4985-4990 (2000)).

In addition, antisense technology can be conveniently used. To accomplish this, a nucleic acid segment at least substantially identical to the desired gene is cloned and operably linked to a promoter such that the antisense strand of RNA will be transcribed. The expression cassette is then transformed into a plant and the antisense strand of RNA is produced. In plant cells, it has been suggested that antisense RNA inhibits gene expression by preventing the accumulation of mRNA which encodes the protein of interest, see, e.g., Sheehy et al., *Proc. Natl. Acad. Sci. USA,* 85:8805 8809 (1988), and Hiatt et al., U.S. Pat. No. 4,801,340.

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990), and U.S. Pat. Nos. 5,034,323, 5,231,020, and 5,283,184.

For these techniques (RNAi, antisense or sense suppression), the introduced sequence in the expression cassette need not have absolute identity to the target gene. In addition, the sequence need not be full length, relative to either the primary transcription product or fully processed mRNA. One of skill in the art will also recognize that using these technologies families of genes can be suppressed with a transcript. For instance, if a transcript is designed to have a sequence that is conserved among a family of genes, then multiple members of a gene family can be suppressed. Conversely, if the goal is to only suppress one member of a homologous gene family, then the transcript should be targeted to sequences with the most variance between family members.

Gene expression can also be inactivated using recombinant DNA techniques by transforming plant cells with constructs comprising transposons or T-DNA sequences. Mutants prepared by these methods are identified according to standard techniques. For instance, mutants can be detected by PCR or by detecting the presence or absence of ACC oxidase mRNA, e.g., by northern blots or reverse transcriptase PCR (RT-PCR).

Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs. The design and use of target RNA-specific ribozymes is described in Haseloff et al. *Nature,* 334:585-591 (1988).

Oligonucleotide-based triple-helix formation can also be used to disrupt gene expression. Triplex DNA can inhibit DNA transcription and replication, generate site-specific mutations, cleave DNA, and induce homologous recombination (see, e.g., Havre and Glazer, *J. Virology* 67:7324-7331 (1993); Scanlon et al., *FASEB J.* 9:1288-1296 (1995); Giovannangeli et al., *Biochemistry* 35:10539-10548 (1996); Chan and Glazer, *J. Mol. Medicine* (Berlin) 75:267-282 (1997)). Triple helix DNAs can be used to target the same sequences identified for antisense regulation.

Methods for introducing genetic mutations described can also be used to select for plants with decreased expression of the peptides of the invention, such as ACC oxidase, or EIN2.

Another strategy is to inhibit the ability of a peptide of the invention to interact with itself or with other proteins. This can be achieved, for instance, using antibodies specific to the peptide of the invention. For example, cell-specific expression of antibodies can be used to inactivate functional domains through antibody:antigen recognition (see, Hupp et al., *Cell* 83:237-245 (1995)).

Alternatively, dominant negative mutants of peptides of the invention can be prepared by expressing a transgene that encodes a truncated peptide. Use of dominant negative mutants to produce inactive target genes in transgenic plants is described in Mizukami et al., *Plant Cell* 8:831-845 (1996). In this approach, non-functional, mutant peptides of the invention which retain the ability to interact with wild-type subunits are introduced into a plant. This approach can be used to decrease ethylene sensitivity in plants by introducing dominant negative mutants of ethylene receptors into plants. For example, an altered *Arabidopsis* ERS gene can be used to confer dominant ethylene insensitivity (Hua et al, *Science* 269:1712-4 (1995)). An ETR1 mutant from *Arabidopsis* has also been used (Wilkinson et al, *Nat Biotechnol.* 15:444-7 (1997) and Chang et at *Science.* 262:539-44 (1993)).

F. Inserting Non-Maize ACC-Modulating Enzymes

Another method of the invention involves modulating ethylene production in maize through the introduction of non-maize genes. In one embodiment of the invention, these genes encode products which increase ethylene production or increase transcription of senescence factors. In another embodiment, these genes encode products which decrease ethylene production or decrease transcription of senescence factors.

One method for inhibition involves the consumption of an intermediate in the ethylene pathway. ACC is an ethylene precursor that is metabolized by several enzymes, such as ACC deaminase or ACC malonyl transferase. The ACC deaminase enzyme metabolizes ACC by converting it to α-ketobutyrate and ammonia. Thus, an ACC deaminase enzyme which possesses sufficient kinetic capabilities can inhibit the synthesis of ethylene by removing ACC from the metabolic pool in the tissues where the ACC deaminase is located.

ACC deaminase is not known in the art to be produced or expressed naturally in maize. Therefore, in order to pursue a method of inhibiting ethylene synthesis in plants by degrading ACC, an ACC deaminase encoding gene must be identified and then be made capable of being expressed in maize. Methods describing the identification, isolation, and introduction of an ACC deaminase gene into a plant are discussed in U.S. Pat. No. 5,702,933.

G. Preparation of Recombinant Vectors

The invention provides a recombinant expression cassette comprising a promoter sequence operably linked to a nucleic acid sequence encoding a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41) wherein the isolated nucleic acid is at least 90% identical to the polynucleotide sequence.

To use isolated sequences in the above techniques, recombinant DNA vectors suitable for transformation of plant cells are prepared. Techniques for transforming a wide variety of higher plant species are well known and described in the technical and scientific literature, e.g., Weising et al., *Ann.* *Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation.

Alternatively, the plant promoter may direct expression of the polynucleotide of the invention in a specific tissue (tissue-specific promoters, organ-specific promoters) or specific environmental condition (inducible promoters).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Nucleic acid sequences of the invention, e.g., nucleic acid sequences that encode ACC oxidase, ACC deaminase, ERS1, ETR2, or EIN2 proteins, are expressed recombinantly in plant cells to enhance and increase levels of endogenous plant transcription factors. For example, ACC oxidase nucleic acid sequences of the invention are expressed recombinantly in plant cells to enhance and increase levels of endogenous ACC oxidase polypeptides. A variety of different expression constructs, such as expression cassettes and vectors suitable for transformation of plant cells can be prepared. Techniques for transforming a wide variety of higher plant species are well known and described in the technical and scientific literature, e.g., Weising et al., *Ann. Rev. Genet.* 22:421-477 (1988). A DNA sequence coding for a polypeptide described in the present invention, e.g., a cDNA sequence encoding a full length ACC oxidase protein, can be combined with cis-acting (promoter and enhancer) transcriptional regulatory sequences to direct the timing, tissue type and levels of transcription in the intended tissues of the transformed plant. Translational control elements can also be used.

The invention provides a nucleic acid encoding an ACC oxidase, ACC deaminase, ERS1, ETR2, or EIN2 polypeptide operably linked to a promoter which, in some embodiments, is capable of driving the transcription of the coding sequence in plants. The promoter can be, e.g., derived from plant or viral sources. The promoter can be, e.g., constitutively active, inducible, or tissue specific. In construction of recombinant expression cassettes, vectors, transgenics, of the invention, different promoters can be chosen and employed to differentially direct gene expression, e.g., in some or all tissues of a plant or animal. Typically, as discussed above, desired promoters are identified by analyzing the 5' sequences of a genomic clone corresponding to the embryo-specific genes described here.

1. Constitutive Promoters

A promoter fragment can be employed which will direct expression of a nucleic acid encoding an ACC oxidase, ACC deaminase, ERS1, ETR2, or EIN2 protein in all transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless, *Arch. Virol.* 142:183-191 (1997)); the 1'- or 2'-promoter derived from T-DNA of *Agrobacterium tumefaciens* (see, e.g., Mengiste (1997) supra; O'Grady, *Plant Mol. Biol.* 29:99-108 (1995); the promoter of the tobacco mosaic virus; the promoter of Figwort mosaic virus (see, e.g., Maiti, *Transgenic Res.* 6:143-156 (1997)); actin promoters, such as the *Arabidopsis* actin gene promoter (see, e.g., Huang, *Plant Mol. Biol.* 33:125-139 (1997)); alcohol dehydrogenase (Adh) gene promoters (see, e.g., Millar, *Plant Mol. Biol.* 31:897-904 (1996)); ACT11 from *Arabidopsis* (Huang et al., *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al., *Plant Physiol.* 104:1167-1176 (1994)), GPc1 from maize (GenBank No. X15596, Martinez et al., *J. Mol. Riot* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf et al., *Plant Mol. Biol.* 29:637-646 (1995).

2. Inducible Promoters

Alternatively, a plant promoter may direct expression of the nucleic acids described in the present invention, e.g., nucleic acids encoding an ACC oxidase, ACC deaminase, ERS1, ETR2, or EIN2 protein, under the influence of changing environmental conditions or developmental conditions. Examples of environmental conditions that may effect transcription by inducible promoters include anaerobic conditions, elevated temperature, drought, or the presence of light. Example of developmental conditions that may effect transcription by inducible promoters include senescence. Such promoters are referred to herein as "inducible" promoters. For example, the invention incorporates the drought-inducible promoter of maize (Busk (1997) supra); the cold, drought, and high salt inducible promoter from potato (Kirch et al., *Plant Mol. Biol.* 33:897 909 (1997)). Examples of developmental conditions include cell aging, and embryogenesis. For example, the invention incorporates the senescence inducible promoter of *Arabidopsis*, SAG 12, (Gan and Amasino, *Science* 270:1986-1988 (1995)) and the embryogenesis related promoters of LEC1 (Lotan et al., *Cell,* 93:1195-1205 (1998)), LEC2 (Stone et al., *Proc. Natl. Acad. Sci. USA* 98:11806-11811 (2001)), FUS3 (Luerssen, *Plant J.* 15:755-764 (1998)), AtSERK1 (Hecht et al., *Plant Physiol* 127:803-816 (2001)), and AGL15 (Heck et al., *Plant Cell* 7:1271-1282 (1995)).

Alternatively, plant promoters which are inducible upon exposure to plant hormones, such as auxins or cytokinins, are used to express the nucleic acids of the invention. For example, the invention can use the auxin response elements E1 promoter fragment (AuxREs) in the soybean (*Glycine max* L.) (Liu, *Plant Physiol.* 115:397-407 (1997)); the auxin-responsive *Arabidopsis* GST6 promoter (also responsive to salicylic acid and hydrogen peroxide) (Chen, *Plant J.* 10: 955-966 (1996)); the auxin-inducible parC promoter from tobacco (Sakai, *Plant Cell Physiol.* 37:906-913 (1996)); a plant biotin response element (Streit, *Mol. Plant Microbe Interact.* 10:933-937 (1997)); and, the promoter responsive to the stress hormone abscisic acid (Sheen, *Science* 274:1900-1902 (1996)). The invention can also use the cytokinin inducible promoters of ARR5 (Brandstatter and Kieber, *Plant Cell* 10:1009-1019 (1998)), ARR6 (Brandstatter and Kieber, *Plant Cell* 10:1009-1019 (1998)), ARR2 (Hwang and Sheen, *Nature* 413:383-389 (2001)), the ethylene responsive promoter of ERF1 (Solano et al., *Genes Dev.* 12:3703-3714 (1998)), and the β-estradiol inducible promoter of XVE (Zuo et al., *Plant J* 24:265-273 (2000)).

Plant promoters which are inducible upon exposure to chemicals reagents which can be applied to the plant, such as herbicides or antibiotics, are also used to express the nucleic acids of the invention. For example, the maize In2 2 promoter, activated by benzenesulfonamide herbicide safeners, can be used (De Veylder, *Plant Cell Physiol.* 38:568-577 (1997)) as well as the promoter of the glucocorticoid receptor protein fusion inducible by dexamethasone application (Aoyama, *Plant J.* 11:605-612 (1997)); application of different herbicide safeners induces distinct gene expression patterns, including expression in the root, hydathodes, and the shoot apical meristem. The coding sequence of the described nucleic acids can also be under the control of, e.g., a tetracycline inducible promoter, e.g., as described with transgenic tobacco plants containing the *Avena sativa* L. (oat) arginine decarboxylase gene (Masgrau, *Plant J.* 11:465-473 (1997)); or, a salicylic acid responsive element (Stange, *Plant J.* 11:1315-1324 (1997)).

3. Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, anthers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, anther-specific or some combination thereof.

Suitable seed-specific promoters are derived from the following genes: MAC1 from maize (Sheridan, *Genetics* 142: 1009-1020 (1996)); Cat3 from maize (GenBank No. L05934, Abler *Plant Mol. Biol.* 22:10131-10138 (1993)); vivparous-1 from *Arabidopsis* (Genbank No. U93215); atmyc1 from *Arabidopsis* (Urao, *Plant Mol. Biol.* 32:571-576 (1996); Conceicao *Plant* 5:493-505 (1994)); napA and BnCysP1 from *Brassica napus* (GenBank No. J02798, Josefsson, *JBL* 26:12196-12201 (1987), Wan et al., *Plant J* 30:1-10 (2002)); and the napin gene family from *Brassica napus* (Sjodahl, *Planta* 197: 264-271 (1995)). Fruit specific promoters include the promoter from the CYP78A9 gene (Ito and Meyerowitz, *Plant Cell* 12:1541-1550 (2000)).

The ovule-specific BEL1 gene described in Reiser, *Cell* 83:735-742 (1995), GenBank No. U39944, can also be used. See also Ray, *Proc. Natl. Acad. Sci. USA* 91:5761-5765 (1994). The egg and central cell specific FIE1 promoter is also a useful reproductive tissue-specific promoter.

Sepal and petal specific promoters are also used to express nucleic acids of the invention in a reproductive tissue-specific manner. For example, the *Arabidopsis* floral homeotic gene APETALA1 (AP1) encodes a putative transcription factor that is expressed in young flower primordia, and later becomes localized to sepals and petals (see, e.g., Gustafson Brown, *Cell* 76:131-143 (1994); Mandel, *Nature* 360:273-277(1992)). A related promoter, for AP2, a floral homeotic gene that is necessary for the normal development of sepals and petals in floral whorls, is also useful (see, e.g., Drews, *Cell* 65:991-1002 (1991); Bowman, *Plant Cell* 3:749-758 (1991)). Another useful promoter is that controlling the expression of the unusual floral organs (ufo) gene of *Arabidopsis*, whose expression is restricted to the junction between sepal and petal primordia (Bossinger, *Development* 122:1093-1102 (1996)).

A maize pollen specific promoter has been identified in maize (Guerrero, *Mol. Gen. Genet.* 224:161-168 (1990)). Other genes specifically expressed in pollen are described, e.g., by Wakeley, *Plant Mol. Biol.* 37:187-192 (1998); Ficker, *Mol. Gen. Genet.* 257:132-142 (1998); Kulikauskas, *Plant Mol. Biol.* 34:809-814 (1997); Treacy, *Plant Mol. Biol.* 34:603-611 (1997).

Promoters specific for pistil and silique valves, inflorescence meristems, cauline leaves, and the vasculature of stem and floral pedicels include promoters from the FUL gene Mandel and Yanofsky, *Plant Cell,* 7:1763-1771 (1995). Promoters specific for developing carpels, placenta, septum, and ovules are also used to express LEC2 nucleic acids in a tissue-specific manner. They include promoters from the SHP1 and SHP2 genes (Flanagan et al. *Plant J* 10:343-353 (1996), Savidge et al., *Plant Cell* 7(6):721-733 (1995)). Promoters specific for the anther tapetum may be derived from the TA29 gene (Goldberg et al., *Philos Trans. R. Soc. Lond. B. Biol. Sci.* 350:5-17 (1995)).

Other suitable promoters include those from genes encoding embryonic storage proteins. For example, the gene encoding the 2S storage protein from *Brassica napus*, Dasgupta, *Gene* 133:301-302 (1993); the 2s seed storage protein gene family from *Arabidopsis*; the gene encoding oleosin 20 kD from *Brassica napus*, GenBank No. M63985; the genes encoding oleosin A, Genbank No. U09118, and, oleosin B, Genbank No. U09119, from soybean; the gene encoding oleosin from *Arabidopsis*, Genbank No. Z17657; the gene encoding oleosin 18 kD from maize, GenBank No. J05212, Lee, *Plant Mol. Biol.* 26:1981-1987 (1994); and, the gene encoding low molecular weight sulphur rich protein from soybean, Choi, *Mol Gen, Genet.* 246:266-268 (1995), can be used. The tissue specific E8 promoter from tomato is particularly useful for directing gene expression so that a desired gene product is located in fruits. Suitable promoters may also include those from genes expressed in vascular tissue, such as the ATHB-8, AtPIN1, AtP5K1 or TED3 genes (Baima et al., *Plant Physiol.* 126:643-655 (2001), Galaweiler et al., *Science* 282:2226-2230 (1998), Elge et al., *Plant J.* 26:561-571 (2001), Igarashi et al., *Plant Mol. Biol.* 36:917-927 (1998)).

A tomato promoter active during fruit ripening, senescence and abscission of leaves and, to a lesser extent, of flowers can be used (Blume, *Plant J.* 12:731-746 (1997)). Other exemplary promoters include the pistil specific promoter in the potato (*Solanum tuberosum* L.) SK2 gene, encoding a pistil specific basic endochitinase (Ficker, *Plant Mol. Biol.* 35:425-431 (1997)); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots.

A variety of promoters specifically active in vegetative tissues, such as leaves, stems, roots and tubers, can also be used to express the nucleic acids used in the methods of the invention. For example, promoters controlling patatin, the major storage protein of the potato tuber, can be used, e.g., Kim, *Plant Mol. Biol.* 26:603-615 (1994); Martin, *Plant J.* 11:53-62 (1997). The ORF13 promoter from *Agrobacterium rhizogenes* which exhibits high activity in roots can also be used (Hansen, *Mol. Gen. Genet.* 254:337-343 (1997)). Other useful vegetative tissue-specific promoters include: the tarin promoter of the gene encoding a globulin from a major taro (*Colocasia esculenta* L. Schott) corm protein family, tarin (Bezerra, *Plant Mol. Biol.* 28:137-144 (1995)); the curculin promoter active during taro corm development (de Castro, *Plant Cell* 4:1549-1559 (1992)) and the promoter for the tobacco root specific gene TobRB7, whose expression is localized to root meristem and immature central cylinder regions (Yamamoto, *Plant Cell* 3:371-382 (1991)).

Leaf-specific promoters, such as the ribulose biphosphate carboxylase (RBCS) promoters can be used. For example, the tomato RBCS1, RBCS2 and RBCS3A genes are expressed in leaves and light grown seedlings, only RBCS1 and RBCS2 are expressed in developing tomato fruits (Meier, *FEBS Lett.* 415:91-95 (1997)). A ribulose bisphosphate carboxylase promoters expressed almost exclusively in mesophyll cells in leaf blades and leaf sheaths at high levels, described by Matsuoka, *Plant J.* 6:311-319 (1994), can be used. Another leaf-specific promoter is the light harvesting chlorophyll a/b binding protein gene promoter, see, e.g., Shiina, *Plant Physiol.* 115:477-483 (1997); Casal, *Plant Physiol.* 116:1533-1538 (1998). The *Arabidopsis thaliana* myb-related gene promoter (Atmyb5) described by Li, *FEBS Lett.* 379:117-121 (1996), is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16-cell stage of embryo development and persists beyond the heart stage. A leaf promoter identified in maize by Busk, *Plant J.* 11:1285-1295 (1997), can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio, *Cell* 86:423-433 (1996); and, Long, *Nature* 379:66-69 (1996); can be used. Another useful promoter is that which controls the expression of 3 hydroxy 3 methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, *Plant Cell.* 7:517-527 (1995)). Also useful are kn1 related genes from maize and other species which show meristem specific expression, see, e.g., Granger, *Plant Mol. Biol.* 31:373-378 (1996); Kerstetter, *Plant Cell* 6:1877-1887 (1994); Hake, *Philos. Trans. R. Soc. Lond. B. Biol. Sci.* 350:45-51 (1995). For example, the *Arabidopsis thaliana* KNAT1 or KNAT2 promoters. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln, *Plant Cell* 6:1859-1876 (1994)).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a nucleic acid described in the present invention is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai, *Proc. Natl. Acad. Sci. USA* 92:1679-1683 (1995)) the rice tungro bacilliform virus (RTBV), which replicates only in phloem cells in infected rice plants, with its promoter which drives strong phloem specific reporter gene expression; the cassava vein mosaic virus (CVMV) promoter, with highest activity in vascular elements, in leaf mesophyll cells, and in root tips (Verdaguer, *Plant Mol. Biol.* 31:1129-1139 (1996)).

H. Production of Transgenic Plants

In a further aspect, the invention provides a transgenic plant comprising a recombinant expression cassette comprising a promoter sequence operably linked to a nucleic acid sequence encoding a polynucleotide sequence such as ACC oxidase (represented by SEQ ID NOs: 2, 7, 11, and 16), ERS (represented by SEQ ID NOs: 21 and 26), ETR (represented by SEQ ID NOs: 31 and 36), or EIN2 (represented by SEQ ID NO: 41), wherein the isolated nucleic acid is at least 90% identical to the polynucleotide sequence.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistics, e.g., DNA particle bombardment.

Microinjection techniques are known in the art and well described in the scientific and patent literature. The introduction of DNA constructs using polyethylene glycol precipitation is described in Paszkowski et al. *Embo J.* 3:2717-2722 (1984). Electroporation techniques are described in Fromm et al. *Proc. Natl. Acad. Sci. USA* 82:5824 (1985). Biolistic transformation techniques are described in Klein et al. *Nature* 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as decreased farnesyltransferase activity. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are generally in Klee et al., *Ann. Rev, of Plant Phys.* 38:467-486 (1987).

The nucleic acids of the invention can be used to confer desired traits on essentially any plant, including maize. Thus, the invention has use over a broad range of plants, including species from the genera *Anacardium, Arachis, Asparagus, Atropa, Avena, Brassica, Chlamydomonas, Chlorella, Citrus, Citrullus, Capsicum, Carthamus, Cocos, Coffea, Cucumis, Cucurbita, Cyrtomium, Daucus, Elaeis, Fragaria, Glycine, Gossypium, Helianthus, Heterocallis, Hordeum, Hyoscyamus, Lactuca, Laminaria, Linum, Lolium, Lupinus, Lycopersicon, Macrocystis, Malus, Manihot, Majorana, Medicago, Nereocystis, Nicotiana, Olea, Oryza, Osmunda, Panieum, Pannesetum, Persea, Phaseolus, Pistachia, Pisum, Pyrus, Polypodium, Prunus, Pteridium, Raphanus, Ricinus, Secale, Senecio, Sinapis, Solanum, Sorghum, Theobromus, Trigonella, Triticum, Vicia, Vitis, Vigna*, and *Zea*.

I. Detection of the Transgenic Plants of the Present Invention

In another aspect, the invention provides a method of modulating ACC oxidase, ERS, ETR, or EIN2 activity in a plant. In an exemplary embodiment, the method further comprises selecting a plant with a phenotype of delayed senescence in its reproductive plant structure. In another exemplary embodiment, the reproductive structure is a seed. In yet another exemplary embodiment, the phenotype is multiple embryos in a single seed. In yet another exemplary embodiment, the construct is introduced by a sexual cross.

In some embodiments, screening further comprises detecting a plant having a desirable phenotype. For example, leaf color can be examined to determine if the photosynthetic life-span of the plant has been affected. Plants with extended photosynthetic life cycles are characterized by leaves that stay green for a longer duration of time as compared to wild type plants. In addition, chlorophyll levels can be measured using well known techniques. Plants that tolerate denser planting can be selected by testing the ability of the plant to grow at higher density. The size of plant vegetative and reproductive structures can be examined to determine if they are larger or smaller than those of a wild type plants. Transgenic plants of the present invention may possess larger fruit, ovules, seeds, pollen, embryonic tissue, flowers, flower parts such as pistils, stamens, sepals, petals, carpels, leaves, stems, tubers, roots, vascular tissue, provascular tissue or root or stem meristems. The resultant transgenic plants can be assayed for increased drought tolerance. Methods for assaying for increased drought tolerance are known and include measuring transpiration rate of transgenic plants, stomatal conductance, rate of water loss in a detached leaf assay or examining leaf turgor. Transgenic plants with decreased transpiration rates, for example, have increased drought tolerance.

Means for detecting and quantifying mRNA or proteins are well known in the art, e.g., Northern Blots, Western Blots or activity assays. For example, after introduction of the expression cassette into a plant, the plants are screened for the presence of the transgene and crossed to an inbred or hybrid line. Progeny plants are then screened for the presence of the transgene and self-pollinated. Progeny from the self-pollinated plants are grown. The resultant transgenic plants can be examined for any of the phenotypic characteristics associated with altered ethylene-related processes, e.g., characteristics associated with staygreen traits or delayed senescence. For example, using the methods of the present invention, inhibition of the nucleic acids or proteins described in the present invention may delay senescence in cells of a vegetative or reproductive plant structure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Examples

Standard methods were used to prepare the nucleic acid sequences disclosed here. The methods are described briefly below.

*Cloning—A Laboratory Manual, Cold Spring Harbor Laboratory*, Cold Spring Harbor, N.Y., (1989).

RT-PCR Analysis

Fifty μg total RNA was treated with RQ1 (Promega) DNase enzyme to ensure that no contaminating DNA was present. Two μg total RNA was used directly for cDNA synthesis using the OMNISCRIPT (Qiagen) reverse transcriptase kit with oligo-dT(20) (SEQ ID NO:49) as the primer.

Analysis of transcript abundance was accomplished using the QUANTITECT SYBR GREEN (Quiagen) PCR kit. Reactions contained 1× buffer, 0.5 μl of the reverse transcription reaction (equivalent to 50 ng total RNA) and 0.25 μM (final concentration) forward and reverse primers (see table below) in a total reaction volume of 25 μl.

| GENE | FORWARD PRIMER (5'-3') | SEQ ID | REVERSE PRIMER (5'-3') | SEQ ID |
|---|---|---|---|---|
| ZmACO15 | ctcgtcttcgatcaattcccaagt | 4 | tacattatcattatttctccggctgt | 5 |
| ZmACO31 | ctcgtcttcgatcaattcccaagt | 13 | atagcaaagagggcaactagctagt | 14 |
| ZmACO20 | ctcatcctgctgctccaggacgac | 9 | tccacgatacacgcataaccaccgt | 10 |
| ZmACO35 | ctcatcctgctgctccaggacgac | 18 | acacacataactgtgccactataagca | 19 |
| ZmERS14 | gagttagtcctcaggatctacctcatgt | 23 | caactcaatccgctggtaggacatact | 24 |
| ZmERS25 | gagttagtcctcaggatctacctcatgt | 28 | caattcaatccgctggtagcatatgt | 29 |
| ZmETR9 | gctatgtatgtgtgaaatttgagattagga | 33 | agctaacctggcagaaattagttaccga | 34 |
| ZmETR40 | gctatgtatgtgtgaaatttgagattagga | 38 | aagctacagcggtctattgagaattct | 39 |
| ZmEIN2-25 | tgggtggtactactacacagcttcct | 43 | aggcttggagaacgcagggtccaaga | 44 |
| ZmEIN3-2 | accccgtacaagaagcctcatga | 45 | gtttatggctggccggacatacaagt | 46 |
| ZmEIN3-3 | accccgtacaagaagcctcatga | 47 | acgaccaagaccctatagactcgacactc | 48 |

DNA and RNA Purification

For total nucleic acid isolation, leaves of B73 were collected at the indicated times, quick-frozen in liquid nitrogen and ground to a fine powder. Ten mL of extraction buffer [100 mM Tris (pH 8.0), 50 mM EDTA, 200 mM NaCl, 1% SDS, 10 μl/mL β-mercaptoethanol] was added and mixed thoroughly until thawed. Ten mL of Phenol/Chloroform (1:1, vol:vol) was added and mixed thoroughly. Samples were centrifuged 10 min at 8,000 rpm, the supernatant removed to a new tube and the nucleic acid precipitated at −20° C. following addition of 1/10 vol 3M sodium acetate and 1 vol isopropanol. Total nucleic acid was pelleted by centrifugation at 8,000 rpm and resuspended in 1 mL TE. One half of the prep was used for DNA purification and the remaining half was used for RNA purification.

For DNA purification, 500 μg DNase-free RNase was added to the tube and incubated at 37° C. for 1 hr. Following RNase digestion, an equal volume of Phenol/Chloroform (1:1, vol:vol) was added and mixed thoroughly. Samples were centrifuged 10 min at 10,000 rpm, the supernatant removed to a new tube and the DNA precipitated at −20° C. following addition of 1/10 vol 3M sodium acetate and 1 vol isopropanol. DNA was resuspended in sterile water and the concentration determined spectrophotometrically. To determine DNA integrity, 20 mg of DNA was separated on a 1.8% agarose gel and visualized following staining with ethidium bromide. RNA was purified by 2 rounds of LiCl$_2$ precipitation according to methods described by Sambrook et al., *Molecular*

Reactions were carried out using an ABI PRISM 7700 sequence detection system under the following conditions: 95° C./15 min. (1 cycle); 95° C./30 sec, 62° C./30 sec, 72° C./2 min (50 cycles); 72° C./5 min (1 cycle). Each gene was analyzed a minimum of four times.

All the primer combinations were initially run and visualized on an agarose gel to confirm the presence single product of the correct size. All amplification products were subcloned into the pGEM-T EASY (Promega) vector system to use for generation of standard curves to facilitate conversion of expression data to a copy/μg RNA basis.

Cloning of the Nucleic Acids of the Invention From *Zea Mays*

ACC oxidase is provided as an example of the cloning of the nucleic acids of the invention. One of skill in the art will recognize that the other nucleic acids of the invention can be cloned by the methods described below and by using the appropriate primers (see the "RT-PCR Analysis" part of the Example section for a listing of appropriate primers).

To clone the maize ACC oxidase gene(s) from maize, primers ACOF1 (ctcatcctgctgctccaggacgac; SEQ ID NO:9) and ACOR1 (cctcgaaccgtggctccttggcctcgaactt; SEQ ID NO:50) were designed using currently available sequences information located in GenBank to amplify two ACC oxidase gene fragments from maize genomic DNA. Following verification of these ACC oxidase fragments by sequencing, a maize (W64) endosperm cDNA library (gift of Dr. B. Larkins) was screened (using the same conditions as outlined above for genomic library screening) to identify a full-length cDNA.

This cDNA was then used to screen a maize (B73) genomic library (same conditions as above). Following identification of several genomic clones, a similar approach as outlined above was used for characterization of the various maize ACC oxidase genes.

Western Blot Analysis

For total protein isolation, leaves of B73 were collected at the indicated times, quick-frozen in liquid nitrogen and ground to a fine powder. One mL of extraction buffer [100 mM Tris (pH 7.5), 100 mM NaCl, 50 mM $CaCl_2$, 50 mM MgCl] was added to approximately 0.5 g frozen powder and mixed thoroughly. Samples were centrifuged 10 min at 10,000 rpm, the supernatant removed to a new tube and the concentration determined spectrophotometrically according to the methods of Bradford, *Anal. Biochem.* 72:248-254 (1976) using a set of BSA standards of known concentration.

Ten mg of protein was separated on 12.5% SDS-PAGE gels and transferred to nitrocellulose membranes. Blots were probed with antibodies to the isolated protein.

Chlorophyll Extraction

Leaves were frozen in liquid nitrogen and ground to a fine powder. Approximately 0.1 g was removed to a 1.5 mL tube and the chlorophyll extracted 3× with 1 mL of acetone. Individual extractions were combined and the chlorophyll content determined spectrophotometrically according to well known methods.

The above example is provided to illustrate the invention but not to limit its scope. Other variants of this invention will be readily apparent to one of ordinary skill in the art and are encompassed by the appended claims.

```
SEQUENCE LISTINGS
Zea mays (B73) ACC oxidase: O15 genomic DNA sequence
                                                        SEQ ID NO: 1
TCGCGAGGCG GCTTAAACTT AGGTCGGCTC GGAGTGGCTC ATGAGCCTCG

AGCGAGCAGA GACGAACCGA GCCAAGTTGT AGAGCTCATT GGTATAACAA

GCCGAGTCAG TTTGCAAGTT ATGCCAAATT AATGAATCTA TAAAATAATA

ATAGATATTG GATAATTTTA TAGATATTCG ACTCGTTCCT TATCATTTAA

TGATGGATTT ATGATAATTT AAAATTTAGA TTACTTATAA TGTTAAATGA

TGGTCATATT TCATATCTAT ATACAATAAT AGTCATTGTA TAATGCAATA

TTATTTATCA AGGTGTAGCT CGCGAGTTGA GTCGAGCCTC CTTCTTAATC

TTATTGAGTG GACGAACCAA GCTGAGCCGA GTCGAGCTTG GTCACCCAGC

GAGTCGAGCC TCCTTCTTAA ACTCGTTGAA TGAGACTCAG CTCATTTCTA

GCCCTAAAAA ATCGCATCAT CATCGGCATA AAGCGAGCAA TGCAGACATT

TTTGGTAGTA CAAGCTTCGG ATGACCGGCT GCAGACGCTT TCTCAATAAC

CTTCTGTAGG GGATCAATGG CCAAGATGAA AGAGGGTCAC CTTGATGAAG

ACTTCAGGCG TGTTTAAATT TTTTGCTTGG GCGATCATTC ACTAGCACTT

TGGAAGATGA TGTAGCCAAG ATGCTAGTCT CTCTATTTTT GACTGAAACC

TAGCTAGAGC TTTTAAAACA TCCCGGAGAT AGTTAAGGGA ATCAAAGGCT

TTTGAAATGT CCAATAGATA CCATTTTTTT TCTTGTGGAG GAGGCTATGA

ATAACATTTT GTTCATATAG AAAATTATCA CATTATGTGA CAAGCAAGGG

AAAATAACTT ATATATAGTT AATAGTGGAG GGAGTGTCTG ATATAAAAAG

CTACATATTT TTGCTGGTTA GTTGTTAGTT AGGTCTTTAC CTGCCCTCTC

TCTACGAACG AGCTGATGCC AGTTCTGACT TTGTCAAAGC ATGGCTGGCA

ATGTGATTGA ATGCCTGATG TTAGCTCGTC ACCTTGACAG GGACATCCGA

TCCTGAATTT CCGATTGGGG TGGCAAAGGT CAAGTTGCCA CCACAAGCAT

CAGTCCAAT GGCTCTGCCA CTGCCCAGAA GCTTCATCAC ACCTAGAGGT

AGCCATGACA GGACCCAAAA AAAGGTCCAG TCCAGGTCCG TACCAGCTGC

GACGACGCTT GTCAGTAGGT AGGTTGAGCT AGCTGCTTGT TGATCACTGC

TATATATACG GGTGCCATGG ATCCATGCCT TCTCCATCCT CAAGTCATCA

GCTAGCTAGC CTTCCCTACA GCAACTGCTT ACATACAACA CTTCCATCTT

CCCGAGCTCG TCTTCGATCA ATTCCCAAGT CAAATAATAA TATAACAACA

ATGGTGGTTC CCGTCATCGA CTTCTCCAAG CTGGACGGCG CTGAGAGGGC
```

-continued

```
CGAAACCCTG GCGCAGATCG CCAATGGCTG CGAGGAGTGG GGATTCTTCC

AGCTCGTGAA CCACGGCATC CCGCTGGAGC TTCTTGAGCG CGTCAAGAAG

GTGAGCTCCG ACTGCTACCG CCTCCGGGAG GCCGGGTTCA AGGCGTCGGA

GCCGGTGCGC ACGCTGGAGG CGCTCGTCGA CGCGGAGCGG CGCGGCGAGG

TTGTGGCCCC GGTGGATGAC CTGGACTGGG AGGACATCTT CTACATCCAC

GACGGATGCC AGTGGCCGTC CGAGCCGCCG GCGTTCAAGG AGACCATGCG

CGAGTACCGC GCCGAGCTGA GGAAGCTCGC CGAGCGCGTC ATGGAGGCCA

TGGACGAGAA CCTCGGCCTC GCCAGGGGCA CCATCAAGGA CGCCTTCTCC

AGCGGCGGCC GGCACGAGCC CTTCTTCGGC ACCAAGGTCA GCCACTACCC

GCCGTGCCCG CGCCCGGACC TCATCACGGG CCTGCGCGCG CACACCGACG

CCGGCGGCGT CATCCTGCTG TTCCAGGACG ACAGGGTCGG CGGCCTGGAG

GTGCTCAAGG ACGGCCAGTG GACCGACGTG CAGCCGCTCG CGGGCGCCAT

CGTCGTCAAC ACTGGCGACC AGATTGAGGT GCTCAGCAAC GGGCGCTACC

GCAGCGCCTG GCACCGCGTG CTGCCCATGC GCGACGGCAA CCGCCGCTCC

ATCGCTTCCT TCTACAACCC GGCCAACGAG GCCACCATCT CGCCGGCGGC

GGTGCAGGCC AGCGGCGGCG ACGCATACCC CAAGTACGTG TTCGGCGACT

ACATGGACGT GTACGCCAAG CACAAGTTCC AGGCCAAGGA GCCCAGGTTC

GAAGCCGTCA AGGTTGCAGC GCCCAAGTCA TCTCCAGCGG CATAAATAAA

TGGAGGGGAC CAATTATTAA ATGCATTATA ATTTATTTGT TGAATAAAAC

AGCCGGAGAA ATAATGATAA TGTAAAGTAT ATATGATAAA CACCGGTTAG

GATTTAAGGT GTTTAACTTT AGTTGCATGG TATAATATGA TATATTGTTG

TAGCAATAAG TTTATTAAGT ATTCATAAGT GTTCTAAATA GTGGGCTAAG

GCACTTATCC ATCGCCTTTC TCAAACAGAA AATAGTGATT TAATTCGGGC

TATAGCGACT AATAGTTGCT ATATATATTA GGCGTAGTAG CAAACAATTT

CACCCTTTGG AAACAGTTAT ATCTAGAAAT AACTATAGCC AGAGATTTAG

AACCTTGTTA ATCATGTAGA AATTAAAGGT TCGTCAAGTC AGAGCGGCAC

CGAACAAGAT AAAAATGTGA CCTCCCCTAT ATGCAAATGT CTGCCAACTT

ATTACATTGG TGGGTGCCAT CTTACTATGT ACAAATATAT CGCGGAAACC

ATATTATCAG CGTCGAGAAT TGGCCATACC CCTGGATATT GATAATATGC

CTTGCGAGAT CTATTGAGCT GAAGAAAACT CGTAGGGGGT CTAGCTAGTG

CCATACCTAA

Zea mays (B73) ACC oxidase: 015 coding sequence (cds)
                                              SEQ ID NO: 2
ATGGTGGTTC CCGTCATCGA CTTCTCCAAG CTGGACGGCG CTGAGAGGGC

CGAAACCCTG GCGCAGATCG CCAATGGCTG CGAGGAGTGG GGATTCTTCC

AGCTCGTGAA CCACGGCATC CCGCTGGAGC TTCTTGAGCG CGTCAAGAAG

GTGAGCTCCG ACTGCTACCG CCTCCGGGAG GCCGGGTTCA AGGCGTCGGA

GCCGGTGCGC ACGCTGGAGG CGCTCGTCGA CGCGGAGCGG CGCGGCGAGG

TTGTGGCCCC GGTGGATGAC CTGGACTGGG AGGACATCTT CTACATCCAC

GACGGATGCC AGTGGCCGTC CGAGCCGCCG GCGTTCAAGG AGACCATGCG

CGAGTACCGC GCCGAGCTGA GGAAGCTCGC CGAGCGCGTC ATGGAGGCCA

TGGACGAGAA CCTCGGCCTC GCCAGGGGCA CCATCAAGGA CGCCTTCTCC
```

-continued

```
AGCGGCGGCC GGCACGAGCC CTTCTTCGGC ACCAAGGTCA GCCACTACCC

GCCGTGCCCG CGCCCGGACC TCATCACGGG CCTGCGCGCG CACACCGACG

CCGGCGGCGT CATCCTGCTG TTCCAGGACG ACAGGGTCGG CGGCCTGGAG

GTGCTCAAGG ACGGCCAGTG GACCGACGTG CAGCCGCTCG CGGGCGCCAT

CGTCGTCAAC ACTGGCGACC AGATTGAGGT GCTCAGCAAC GGGCGCTACC

GCAGCGCCTG GCACCGCGTG CTGCCCATGC GCGACGGCAA CCGCCGCTCC

ATCGCTTCCT TCTACAACCC GGCCAACGAG GCCACCATCT CGCCGGCGGC

GGTGCAGGCC AGCGGCGGCG ACGCATACCC CAAGTACGTG TTCGGCGACT

ACATGGACGT GTACGCCAAG CACAAGTTCC AGGCCAAGGA GCCCAGGTTC

GAAGCCGTCA AGGTTGCAGC GCCCAAGTCA TCTCCAGCGG
```

Zea mays (B73) ACC oxidase: O15 amino acid sequence
                                        SEQ ID NO: 3
```
MVVPVIDFSK LDGAERAETL AQIANGCEEW GFFQLVNHGI PLELLERVKK

VSSDCYRLRE AGFKASEPVR TLEALVDAER RGEVVAPVDD LDWEDIFYIH

DGCQWPSEPP AFKETMREYR AELRKLAERV MEAMDENLGL ARGTIKDAFS

SGGRHEPFFG TKVSHYPPCP RPDLITGLRA HTDAGGVILL FQDDRVGGLE

VLKDGQWTDV QPLAGAIVVN TGDQIEVLSN GRYRSAWHRV LPMRDGNRRS

IASFYNPANE ATISPAAVQA SGGDAYPKYV FGDYMDVYAK HKFQAKEPRF

EAVKVAAPKS SPAA
```

Zea mays (B73) ACC oxidase: O15 forward primer sequence
                                        SEQ ID NO: 4
```
CTCGTCTTCGATCAATTCCCAAGT
```

Zea mays (B73) ACC oxidase: O15 reverse primer sequence
                                        SEQ ID NO: 5
```
TACATTATCATTATTTCTCCGGCTGT
```

Zea mays (W64) ACC oxidase: O20 genomic sequence (truncated)
                                        SEQ ID NO: 6
```
ATTCCGTTGC CCCTGTCAAG TGTACATCAN ATTGAATGCT GTGTTAGGCC

AGCAACTATC ACAATCCCAA GTCATAGCAG GTGACGGTGC GATCGACGCG

CTTTGTTTGG TGGAACATTT TCCCGTGTTC AATTCTTTCT TCCCTTCTTT

TTTTTTTTAA AAAAAAGCT TTCCGTGTCG CTGCTGCAGC AAGTGATGAA

GCAGTTCGCA TCGGAGGTGC AGAAGCTGTC GGAGAAGGTG CTGGACTTGC

TGTGCGAGAA CCTGGGCCTG GAGCCCGGGT ACCTGAAGGC GGCCTTCGCG

GGGTCGGACG GCGGCCCGAC GTTCGGCACC AAGGTGAGCG CGTACCCGCC

GTGCCCGCGC CCGGACCTGG TGGCCGGCCT GCGCGCGCAC ACCGACGCCG

GCGGCCTCAT CCTGCTGCTC CAGGACGACC AGGTGAGCGG GCTGCAGCTG

CTCAGGGGCG GCGACGGCGG GGAGTGGGTG AACGTGCCGC CGCTGCGCCA

CGCCATCGTC GCCAACGTCG GCGACCAGCT GGAGGTGGTC ACCAACGGGC

GGTACAAGAG CGCGGTGCAC CGCGTGCTCG CCCGCCCCGA CGGCAACCGC

ATGTCCGTCG CGTCCTTCTA CAACCCGGGC GCCGACGCCG TCATCTTCCC

GGCCCCCGCG CTCGTCGGCG AGGAGGAGCG AGCCGAGAAG AAGGCCACCA

CGTACCCGAG GTTCGTGTTC GAGGACTACA TGAACCTGTA CGCGCGCCAC

AAGTTCGAGG CCAAGGAGCC CCGGTTCGAG GCCATGAAGT CGTCGGCCAT

CGCCACCGCG TGAGCACATA ATACTGCCGT GTTCTCCCTT CGTGGGGTGC
```

```
ATATGCTTGA GCTTGAAGAG CCATGTGCCT GTATGTAGTG GCACGTACGG

TGGTTATGCG TGTATCGTGG AATGGCGCGG CGTGATGTAT TTTGGTTGTC

TCAGATCTAA GTGTGTGCGT ATATATTGTG TACTGTAAAG TTTGCAGCGT

CTGATTAATG TACGAGCAGT GTGTGTACCT AACCAGAACC TGGAATGTGG

CTGGCTGTGT GCTGATATTA CTACCACATC AGGTGAGTGG CCACCCGTCG

TCGCCTCCTA CGGCTCCGGT GCCGACTCGA CCCCTTCCTT CCCTGCGACC

CTGCGGCCCC ACCGCCCTTA TCTCCATGGA TACTTGCGGC GAGCAAAGGC

TTAACAAAGG AGAACAGTGT GCAAAACATA CCTGCAGTGA GCAAAGGCTT

TACATGAGGA TATCAGGATA TGCACAGACC TACCATACAA GCTATAGCCT

TTCCTTTACA ACAAAACACC AGCTAGAAGA TCCGCATATG CTACCGATTG

TTCACTCTCC ATGTTTTGTT CGGCTTACAT TGTTACGCTG AGTTAGATGG

TTAATTGCAC AGTAACCTGC CGACTGCACT ATCACCTTGT CTTGGCTTTC

CTTCTCTTCT ATACAAAAGC GAGTCAGTGG ACACATTCAG AGAAGTGGAA

GGGAAGAAAG AAGAAA
```

Zea mays (W64) ACC oxidase: O20 coding sequence (cds)
SEQ ID NO: 7
```
ATGGCAGCCA CGGTGTCCTT CCCGGTGGTG AACATGGAGA AGCTGGAGAC

CGAGGAGAGG GACACGGCCA TGGCGGTCAT CCGCGACGCC TGCGAGAACT

GGGGCTTCTT CGAGCTGCTG AACCATGGCA TCTCGCACGA GCTGATGGAC

GAGGTGGAGC GGCTGACCAA GGCGCACTAC GCCACCTTCC GGGAGGCCAA

GTTCCAGGAG TTCGCGGCGC GGACGCTGGC CGCGGCCGGC GACGAGGGCG

CCGACGTCAG CGACGTGGAC TGGGAGAGCA CCTTCTTCGT CCGCCACCTC

CCGGCCTCCA ACCTCGCCGA CCTCCCCGAC GTCGACGACC ACTACCGGCA

AGTGATGAAG CAGTTCGCAT CGGAGGTGCA GAAGCTGTCG GAGAAGGTGC

TGGACCTGCT GTGCGAGAAC CTGGGCCTGG AGCCCGGGTA CCTGAAGGCG

GCCTTCGCGG GGTCGGACGG CGGCCCGACG TTCGGCACCA AGGTGAGCGC

GTACCCGCCG TGCCCGCGCC CGGACCTGGT GGCCGGCCTG CGCGCGCACA

CCGACGCCGG CGGCCTCATC CTGCTGCTCC AGGACGACCA GGTGAGCGGG

CTGCAGCTGC TCAGGGGCGG CGACGGCGGG GAGTGGGTGG ACGTGCCGCC

GCTGCGCCAC GCCATCGTCG CCAACGTCGG CGACCAGCTG GAGGTGGTCA

CCAACGGGCG GTACAAGAGC GCGGTGCACC GCGTGCTCGC CCGCCCCGAC

GGCAACCGCA TGTCCGTCGC GTCCTTCTAC AACCCGGGCG CCGACGCCGT

CATCTTCCCG GCCCCCGCGC TCGTCGGCGA GGAGGAGCGA GCCGAGAAGA

AGGCCACCAC GTACCCGAGG TTCGTGTTCG AGGACTACAT GAACCTGTAC

GCGCGCCACA AGTTCGAGGC CAAGGAGCCC CGGTTCGAGG CCATGAAGTC

GTCGGCCATC GCCACCGCG
```

Zea mays (W64) ACC oxidase: O20 amino acid sequence
SEQ ID NO: 8
```
MAATVSFPVV NMEKLETEER DTAMAVIRDA CENWGFFELL NHGISHELMD

EVERLTKAHY ATFREAKFQE FAARTLAAAG DEGADVSDVD WESTFFVRHL

PASNLADLPD VDDHYRQVMK QFASEVQKLS EKVLDLLCEN LGLEPGYLKA

AFAGSDGGPT FGTKVSAYPP CPRPDLVAGL RAHTDAGGLI LLLQDDQVSG

LQLLRGGDGG EWVDVPPLRH AIVANVGDQL EVVTNGRYKS AVHRVLARPD
```

```
GNRMSVASFY NPGADAVIFP APALVGEEER AEKKATTYPR FVFEDYMNLY

ARHKFEAKEP RFEAMKSSAI ATA

Zea mays (W64) ACC oxidase: O20 forward primer sequence
                                                       SEQ ID NO: 9
CTCATCCTGCTGCTCCAGGACGAC Zea mays (W64) ACC oxidase: O20 reverse primer sequence
                                                       SEQ ID NO: 10
TCCACGATACACGCATAACCACCGT Zea mays (B73) ACC oxidase: O31 coding sequence (cds)
                                                       SEQ ID NO: 11
ATGGTGGTTC CCGTGATCGA CTTCTCCAAG CTGGACGGCG CTGAGAGGGC

TGAAACCCTG GCGCAGATCG CCAATGGCTG CGAGGAGTGG GGATTCTTCC

AGCTCGTGAA CCACGGCATC CCGCTGGAGC TGCTCGAGCG CGTCAAGAAG

GTGTGCTCCG ACTGCTACCG CCTCCGGGAG GCCGGGTTCA AGGCGTCGGA

GCCGGTGCGC ACGCTGGAGG CGCTCGTCGA CGCGGAGCGG CGCGGTGAGG

TGGTGGCGCC GGTGGACGAC CTGGACTGGG AGGACATCTT CTACATCCAC

GACGGATGCC AGTGGCCGTC CGACCCGCCG GCGTTCAAGG AGACCATGCG

CGAGTACCGC GCCGAGCTGA GGAAGCTCGC CGAGCGAGTC ATGGAGGCCA

TGGACGAGAA CCTCGGCCTC GCCAGGGGCA CCATCAAGGA CGCCTTCTCC

GGCGGCGGCC GGCACGATCC CTTCTTCGGC ACCAAGGTCA GCCACTACCC

GCCGTGCCCA CGCCCGGACC TCATCACGGG CCTGCGCGCG CACACCGACG

CCGGCGGCGT CATCCTCCTG TTCCAGGACG ACAAGGTCGG TGGCCTGGAG

GTGCTCAAGG ACGGCGAGTG GACCGACGTA CAGCCGCTCG AGGGCGCCAT

CGTCGTCAAC ACCGGCGACC AGATCGAGGT GCTCAGCAAC GGGCTGTACC

GCAGCGCTTG GCACCGCGTG CTGCCCATGC GCGACGGCAA TCGCCGCTCC

ATCGCATCCT TCTACAACCC AGCCAACGAA GCCACCATCT CGCCGGCGGC

GGTGCAGGCC AGCGGCGGTG ACGCGTATCC CAAGTACTTG TTCGGCGATT

ACATGGACGT GTACGTCAAG CAGAAGTTCC AGGCCAAGGA GCCTAGGTTC

GAAGCCGTCA AGACGGGGGC GCCAAAGTCA TCTCCAGCGG CA

Zea mays (B73) ACC oxidase: O31 amino acid sequence
                                                       SEQ ID NO: 12
MVVPVIDFSK LDGAERAETL AQIANGCEEW GFFQLVNHGI PLELLERVKK

VCSDCYRLRE AGFKASEPVR TLEALVDAER RGEVVAPVDD LDWEDIFYIH

DGCQWPSDPP AFKETMREYR AELRKLAERV MEAMDENLGL ARGTIKDAFS

GGGRHDPFFG TKVSHYPPCP RPDLITGLRA HTDAGGVILL FQDDKVGGLE

VLKDGEWTDV QPLEGAIVVN TGDQIEVLSN GLYRSAWHRV LPMRDGNRRS

IASFYNPANE ATISPAAVQA SGGDAYPKYL FGDYMDVYVK QKFQAKEPRF

EAVKTGAPKS SPAA

Zea mays (B73) ACC oxidase: O31 forward primer sequence
                                                       SEQ ID NO: 13
CTCGTCTTCGATCAATTCCCAAGT Zea mays (B73) ACC oxidase: O31 reverse primer sequence
                                                       SEQ ID NO: 14
ATAGCAAAGAGGGCAACTAGCTAGT Zea mays (B73) ACC oxidase: O35 genomic sequence
                                                       SEQ ID NO: 15
```

```
CTTAAGATTG GGCTTCAGTG ACTAACAATC CGCATATATA TTCTTTTGGT

GCTAGTTTGA AAATTGAAAT CCTCTCCGGG ATTTCTGGGG ATTGAGACTC

AATCTCCAGG AATCCCGAGG TGGTTTAAGT TTTAAAACTA GTCTTAAAGT

TTTAATGCAA TAAAATACAA AATTTAATGT ACTTATGTCG GAATTTATTT

GGAACAAATA AAAACAGGAA TTTGCTAATT TTGGTAGGTG GTGCGGCGGT

GACCGAAAAA AACATGAAAA GCCGTATTCA AATCTGGATT CGTTGTGGAG

TACCTACGTA TGCCAATATC TCTAAAGTAT AGGATTAGGC CAATAGATAA

CTAGGTCATA TAATAGCACC ACAGCCGTAT GATATCGTAC AATATTATAA

TGTACATCAT ATATATCCAG CCTAATTAGC TGGGGTCAGT TGCAATAATC

TTCAGAGGAC TTGTCTGTAT CTCGAGTAGC CCGCATAATT GCGGCTCGCC

GTGCCCGTGC ACACGTCTAG TTATAGATGT GTAAAAAAAA TCTGTCCACT

CGGTATATGG TCCACTCAGC TCGCCGTGCA CGCATCTAGT TTGAGATGAC

GCGGTGCGAT GAAGGGGTCG CACGGAGGAG GGGAGGGGGA GTTAGGGTTA

GCAGGCAAGT TGAGTGGTGT GCTGGTTGTC TAGTAAAATC TTAGCAGACT

TTTGTAGATT AGGTCATACT GTGTCAAACT GTCAACTGCC GTACACGATA

GGCGATTTGC TAAATTACCA ATATTATTAG GCCTTGTTCG GTTATTCCCA

ATACACCTGG ATTGAATGAG ATTGGAAAAA ATTCTTAAGA ACTTTGAATT

GTTTGGGATT CAAACCCATC CAATCCCACT CAATCCACAT GGATTGAGAG

CTAACCGAAC AAGCCCTTAG TGGGTTTCAG AGATTTATC TTCAGACCTA

TAAATTATAG GTGCAGATAT ATAGACTAAA AAACATAGAC ATAGATGGTA

TTATAGCAAG AAGGAACAAA TTCAGTGCTA ATTATTTCGA ATACGGTACT

GCACATCCGG ACTGTCCTGT CCCAGCCTCT CCCAGGTTGC ATGCTCATCT

ACACCGTCGA GCGTCGAGGC GGCTAGCTCT AGCCGATCAG CGAGCATCGC

GGGCTATATA CGTCCAGACT GCTTTCATTT GAGAATGCGT AGTTTGGCTT

CCTAATCCAT TTGAGTAAAT TATGAAAGTA ATGATAAACG TACCGTCGCG

AGGTCACTCT GGTAATCCAA CATTTCTCGC TCAGCCGCCT ATAAATTGGG

CCGCGCGCAC CGCCTCGCTC TCCACTCAAA CAAACTCAAG CCTGCCCTGC

CCTGCCTTGT TAAGCAAAGC AACCCAGCTG CGAGACACGA GAGCTAGCTA

GAGAGAGATG GCGGCCACGG TTTCCTCCTT CCCGGTGGTG AACATGGAGA

AGCTGGAGAC AGAGGAGAGG GCCACGGCCA TGGAGGTCAT CCGCGACGGC

TGCGAGAACT GGGGCTTCTT CGAGGTGTGC ATATACATAC TCTGCAGACT

GCTTGCTGCT CACACCAAGC TACCACAGAA CACAATTATT CTACTAACCA

ACGCACCACA CCTGATCACA ATAAGTAATG ATCTAACCAC ACAGCAGGAA

GAATTACTAC TTCACTTGTT GTTTGCCTGA CCTGCCACCC CCCTGCTTCT

TCAACATCTA GAGCCCCTTC ATTCTGTCAG CACATGCAAG CTGTTCGTTT

CGGATCAAAT CTATTTGTTC GGACTGCTGA CAGTAGAAAC CGATACTCGT

TAAAGCCAGC ACCACCGTTC CAGAAAAAGA AAAGCAAAAC AAAGTATTCT

AGCAGCTTGC TTTACCTAAC AAACAGCCTC CGATCCTCGA ACGTACAGAT

TCCTATTCTC CATGCCATCA ACCGGCCGAC CACCAGCTGA TTCCATCACG

TCTCTCTCTC ACCGCGCCTA GCTGATGAGC ACACACAAAG TAGCATCTTA

TCTATTGGTT CGTTGATGCC CAGCTCTCGA ACGAATCACC ATCTCATGTA
```

```
-continued
TTGTCTTGTC CCCATCCCCA TGCATGCAGC TGCTGAACCA CGGCATCTCG

CACGAGCTGA TGGACGAGGT GGAGCGGCTG ACCAAGGCGC ACTACGCCAC

CTTCCGGGAG GCCAAGTTCC AGGAGTTCGC GGCCCGGACG CTGGAGGCCG

GCGAGAAGGG CGCCGACGTC AAGGACGTGG ACTGGGAGAC CACCTTCTTC

GTCCGCCACC TCCCGGCCTC CAACCTCGCC GACCTCCCCG ACGTCGACGA

CCGCTACAGG TGCGTTCAGA CCTCAAACAC AACACTACGT GCGTGCGTGC

GTGCTAGCTA GCTAGCTTAT GCGCGCCATT AAATTAATGA CGTCTGGCGC

ACAGGGCCGG GCCGGCATAA TTGAAGGCCC TGTACTGTTT TTTTTTCTTT

TTTTTCTTTG TTAAGAATAG ATGATACAGA TTAATCTCAT TTATTAACAG

TGATTGAATT ATTAATGTAG GAAATGGCTT AATAACGATA ACAAATGATC

TTAAAGTTTG GATTTTATGC TAGCATGTGC TAGCTGCACT TCGCCATATA

GCCAAAATAA GTTGCATGAG AGATTGGTAC TCGCTTGTTA CGACAAACAC

TATGTTTTAT TCTTATCGAG CTGACTTAGC TAGACTTTCT AATCATTACT

AAAATTTATA TTGATTAAAT TATCACTAAC TATTATTTTA GGGGCCCTTG

AAGGGAGGGG GCCCTGTTCT TGTGCACTAG TGACACATGC CTCCCGCCCG

GGCCTGCTGG CGCAGTATCG TATATTTATT AGTGTTTGGC TGCTAGCTGC

GACCCAATGA TCAGTCGTCT TTGTTAATCG ACTTTTTGTT GGCTTCTGAC

GGATGTTCTA AGTGCCATGT CACCCGCTTT TGACTGATCA GTTTATTTTA

ATTGATCTGA TTAGTCTTAG CTTGAGAGTG ACTTGAGTAT AGCAGGCTGG

GATACTACCT GACCTGCTCC TACATAACGG ATTAAGTAAT GTTTCAAGAA

ATTTTGTCCA TACGCATATA ATTAAGTTAT CATTATCAGA ATTCTGCCTG

ACGACGACGA CGACGACGCG AAAACAGTTA GTTATCTGTT CATCTCGTTG

CCTTTAATTG CTTGACAAGC TAGCTAGCTA GCTGTACAGC AGAATGCGGT

GCGAGCCCCG TAGCTATGAC AAGGTCGATC GAATCGCCTT TTCAGCAGGC

GACAGCGCTA TTTGTCCGGT GGAATTATTC CGGCCGTGTC TCAAAGCCTT

CCTTCCGTAC GTGTCGCTGC AGGCAGGTGA TGGAGCAGTT CGCATCGGAG

ATCCGCAAGC TGTCGGAGAG GCTGCTGGAC CTGCTGTGCG AGAACCTGGG

CCTGGAGCCC GGGTACCTGA AGGCGGCCTT CGCGGGGTCG GACGGCCCGA

CGTTCGGCAC CAAGGTGAGC GCGTACCCGC CGTGCCCGCG CCCGGACCTC

GTCGACGGCC TCCGCGCGCA CACCGACGCC GGcGGCATCG TGCTGCTGTT

CCAGGACGAC CAGGTGAGCG GCCTGCAGCT GCTCAGGGGC GGGGAGTGGG

TGGACGTGCC GCCCATGCGC CACGCCATCG TCGCCAACGT CGGCGACCAG

CTGGAGGTGA TCACCAACGG GCGGTACAAG AGCGTCATGC ACCGCGTGCT

CACGCGCCCC GACGGCAACC GCATGTCCGT CGCGTCCTTC TACAACCCGG

GCGCCGACGC CGTCATCTTC CCGGCCCCCG CGCTCGTCGG CGCCGCCGAG

GAGGACCGCG CCCGAGGCCGC GTACCCGAGC TTCGTGTTCG AGGACTACAT

GAACCTGTAC GTGCGCCACA AGTTCGAGGC CAAGGAGCCC AGGTTCGAGG

CCATGAAGTC GGCCATCGCC ACCGCGTGAG AGAAGACTGC CTTCCGCTGC

AGGCTTCCTT CGTGGCGTCA AGCCTTGAGG CTTGAACGAA CAACGTACGT

CCATGTGCTT ATAGTGGCAC AGTTATGTGT GTAACTACCG ATCGTGGAAC
```

```
GGCCTAATGT ATTTCGGTTG CCTCAGATCG ATCTATATGT GCGTATACAT

TATGTACTGA AAAGTGTGTA GCGTCTGGTT AATGTATGAG CAGTGTGTAT

GTGACCGGGA CCCGGTGTGT AGTTGCTATT ACTACCATAT CCGGTGAATG

ATCAAACCTT TTGGTGTATT AAAACTAGAT GTTCATCCCC TCACGGACTA

CCCTGGTATT GACAACCAAA ACGGAATATG ACATATATAG TAAAAACATG

ATTTCCCGGC AAGAAAGGG GACTATTCCA ACTCGG
```

Zea mays (B73) ACC oxidase: O35 coding sequence (cds)
SEQ ID NO: 16

```
ATGGCGGCCA CGGTTTCCTC CTTCCCGGTG GTGAACATGG AGAAGCTGGA

GACAGAGGAG AGGGCCACGG CCATGGAGGT CATCCGCGAC GGCTGCGAGA

ACTGGGGCTT CTTCCAGCTG CTGAACCACG GCATCTCGCA CGAGCTGATG

GACGAGGTGG AGCGGCTGAC CAAGGCGCAC TACGCCACCT TCCGGGAGGC

CAAGTTCCAG GAGTTCGCGG CCCGGACGCT GGAGGCCGGC GAGAAGGGCG

CCGACGTCAA GGACGTGGAC TGGGAGAGCA CCTTCTTCGT CCGCCACCTC

CCGGCCTCCA ACCTCGCCGA CCTCCCCGAC GTCGACGACC GCTACAGGCA

GGTGATGGAG CAGTTCGCAT CGGAGATCCG CAAGCTGTCG GAGAGGCTGC

TGGACCTGCT GTGCGAGAAC CTGGGCCTGG AGCCCGGGTA CCTGAAGGCG

GCCTTCGCGG GGTCGGACGG CCCGACGTTC GGCACCAAGG TGAGCGCGTA

CCCGCCGTGC CCGCGCCCGG ACCTCGTCGA CGGCCTCCGC GCGCACACCG

ACGCCGGNGG CATCGTGCTG CTGTTCCAGG ACGACCAGGT GAGCGGCCTG

CAGCTGCTCA GGGGCGGGGA GTGGGTGGAC GTGCCGCCCA TGCGCCACGC

CATCGTCGCC AACGTCGGCG ACCAGCTGGA GGTGATCACC AACGGGCGGT

ACAAGAGCGT CATGCACCGC GTGCTCACGC GCCCCGACGG CAACCGCATG

TCCGTCGCGT CCTTCTACAA CCCGGGCGCC GACGCCGTCA TCTTCCCGGC

CCCCGCGCTC GTCGGCGCCG CCGAGGAGGA CCGCGCCGAG GCCGCGTACC

CGAGCTTCGT GTTCGAGGAC TACATGAACC TGTACGTGCG CCACAAGTTC

GAGGCCAAGG AGCCCAGGTT CGAGGCCATG AAGTCGGCCA TCGCCACCGC

G
```

Zea mays (B73) ACC oxidase: O35 amino acid sequence
SEQ ID NO: 17

```
MAATVSSFPV VNMEKLETEE RATAMEVIRD GCENWGFFQL LNHGISHELM

DEVERLTKAH YATFREAKFQ EFAARTLEAG EKGADVKDVD WESTFFVRHL

PASNLADLPD VDDRYRQVME QFASEIRKLS ERLLDLLCEN LGLEPGYLKA

AFAGSDGPTF GTKVSAYPPC PRPDLVDGLR AHTDAGGIVL LFQDDQVSGL

QLLRGGEWVD VPPMRHAIVA NVGDQLEVIT NGRYKSVMHR VLTRPDGNRM

SVASFYNPGA DAVIFPAPAL VGAAEEDRAE AAYPSFVFED YMNLYVRHKF

EAKEPRFEAM KSAIATA
```

Zea mays (B73) ACC oxidase: O35 forward primer sequence
SEQ ID NO: 18

```
CTCATCCTGCTGCTCCAGGACGAC
```

Zea mays (B73) ACC oxidase: O35 reverse primer sequence
SEQ ID NO: 19

```
ACACACATAACTGTGCCACTATAAGCA
```

Zea mays ethylene receptor (ethylene response sensor receptor, ERS1-like); ERS14 genomic DNA sequence.
SEQ ID NO: 20

-continued

```
TTTTACAAAT CGTTTTGAAT AAGAATTCGG ATCAACACCT GATATTGAAG
GGGGACGAAC TTGAGTGATT TGACTGCATG CTCGACCCTT TTTGATGTAC
TGAACTCCTG CAATATGTCT AAAATACCAA GGTAAAGAAC AACATCGTAC
TCCTCAATGG TATCCGGGTT TTCAAGTTCC GTGTTCATGT CCTCATGCAC
TTTCCGAGCT TGAGCTGGCA TATTCACCCC CAACTGTACA CGGAACCTGA
AAGCACAATA CAGAATACAC ATGAATCGGC AACAAAATCC ATCTAGATTT
TTTTAGCAAG ACTGAGAAAA CTACTCTCCA ACAAATTTCT ATTTCAATTC
CATCATTTGG GAATGGGCAA ACATTCTAAT CATATGGAAA TATTCGTGCG
AGTATTGTCC ATCAATCCAG TGGTGGAAGA ACATAAAAAC AGTAAGAGTA
TGATAGTGAT TCCAATGCAA GTGTATAAAA TAGACAAACG TATAAAAATT
TCAATATTGT AGAAGTGAGA TTTTAAAAAT CGTTGGATAA ATTCAACAAA
TATATATCTA ATATTTTAGC CGCTTAAAAA AACTTTCTAC AATCTCACTT
CTACAAAAAA TATTATTAAG AGTATGTTTT TTTAATTATT ATTAAGAGTA
TGGTTCAAAA TGAAAATTCA CTTTTTTTAG AGTATGGTTC AAAACGATCC
TTTTAGGTTA AGTTTGAATA AGACGTGCCG GACTTAAAAT ATATTATATA
CTAAACAGTA TTATAGTAAA ATTAATAATA ATTATATTTT TTTGAGATGA
GTCGATCAAA CTTAAGATTA AAAATTAAA GGAAATTAAA AATTGAAACA
TAGGGAGTAT TAATTTATAA ACTGTTGGAA AGACTCCAAT GAGTAATGTC
CCATCAGATA AGAGGACACC CCCTGTCATC TTTTTGGCCT ACCTTCGTCG
TATCTCCAAG AGTCTAAATT TTATTTTTAA AATTATTATC TAAAGAATGA
TTTATATAAA AACATTTAT ATATTTTTC TAATCTCCAA CAAATTTTTA
TATCTTATTT GAGCCATTAA TGTTTCCTAT CTTTGACTAA CAAGAAACAC
ATAATAGATG ATGACTATAT TTAGATAATC GTTTAAATAA GTTGTTGGAG
TATTTTTTTT ATAAAAAATC TCTACTCATA TGAATTAGAA AAACTTTGGA
GTTGCTTATG ACTTTTCATG CCTTGTCTGT AGCCGCATGA TGCAGATACA
ATACAGTATG GACACAGTGC TTAACTACCC CGTATGACCA TATCACTGCA
GAAGATAGCG TTCAGATCAA GACAGAAAAC AAGCAAGACG ATCTTAACCA
AACAGCCGTC CACTGCCTTT TCTTTCTCCC GTTCACCCCG CCGTGCACGC
TCTTTTTGTC CCTCGTGCCG ACGACCGACC GACCGCCGCC GCCTCAAGGT
CTTCGTAAAG CCACTCGCCG GCAACGAGCA GCCACCAGGT ATGCCAGCAC
CTTCTCTTCC ATTCCTGCTG TACGAAACCG AGCACGCAAA CCCTAACTTA
AGCTAATTGG GTATTTGTAT TCGGATCTCA TCTAATTACA GGTGTTTACA
TGTATTATGC CTACTAACTA ACGCTGATTT TCGTTAAAAA GTTATCGGGT
GTACATGTGT ACATCCATTT CCTTTACTAG GGCCGTTTGG AATTGCAAAT
GGGAGTTGGA GCGGCGAATG ACATGTGGCA TGTCTTGTGG GATTTGCATG
CTCTGCCAGT ACGCGTGCTG CGTTCATGAG CTTATGCTAT TCAAATGCCA
TTTGCTACGC ATTTATGGCT ATTTGGGATC GGGAACTGGC GTGGCAAAAA
CATTTTATCG ATATGTTTCT TCTTCTGCAG GAAGATGTTG TGAGGACTGA
TGCAATAACT AAGCTTGCTG GATGGACGGA TGCGATTGCA TAGAGCCACT
ATGGCCTACC GATGATCTTC TCGTCAAGTA TCAGTACATC TCAGACTTCT
TCATAGCCCT TGCGTACTTC TCGATTCCAT TGGAGCTCAT ATATTTGTG
```

-continued

```
AAGAAGTCGT CCTTCTTCCC ATACAGATGG GTCCTGATCC AGTTTGGTGC

GTTTATAGTT CTTTGTGGGG CAACCCATCT GATAAACCTG TGGACGTTCA

CCACACATAC AAAGACCGTT GCGATGGTCA TGACCATAGC GAAGATTTCT

ACAGCAGTCG TGTCCTGTGC AACTGCTTTG ATGCTCGTTC ATATCATTCC

CGACTTGTTG AGCGTGAAAA CTAGGGAGTT GTTCTTGAAG AATAAAGCTG

AGGAGCTTGA TAGAGAGATG GGACTTATAA GGACGCAAGA GGAGACTGGT

AGACATGTTA GGATGCTTAC ACATGAAATC AGAAGTACTC TTGATAGACA

TACAATTTTG AAGACTACTC TCGTTGAGCT AGGAAGGACC TTGGGTCTGG

AAGAATGTGC ATTGTGGATG CCATCTCGAA GTGGCTCAAG CCTTCAGCTT

TCTCATACTT TGCGCCACCA GATTACTGTT GGATCATCGG TGCCAATGAA

TCTTCCTGTC GTCAATCAAG TGTTCAGTAG CAACCGGGCA ATCATAATAC

CCCACACATC TTCTTTGGCG CGGGTTCGAC CTCTTGCAGG GCGATATGTT

CCACCAGAAG TGGCCGCAGT CCGTGTACCT CTTCTACATC TTTCAAACTT

TCAAATAAAT GATTGGCCTG AGCTCTCAGC AAAAAGCTTT GCAATCATGG

TTTTGATGCT TCCATCTGAT AGTGCTAGAA AATTGCATGT GCATGAATTG

GAGCTGGTTG AGGTCGTTGC TGATCAGGTT CGTGCTGTAT CTTTTGCTAT

GGTTACTATA ACATACTACT TCCATCCAGA GAAGGATGTA AATTTACTTC

TGTCTCTATT CAATTCAAGC TATCTATACT TTTACTAAGT TTATTAAAAA

TATTATCAAT ATATATATCA TCGGATAGGT GTATTTTGAA AATATGTTCC

ATGACAAATC TAACAACACT TATTTGACAG TGTTTTTTAG TTTTTAGTAA

ATTTAGTCAC GGTTTGACTC GGTACTATGC TAGAATTACA TTCTTTTCCG

GATGGAGTAT ATGCTTGTAG GAGAGGAAAA ACATGTTTAC ATCTTTCAAA

ATCATATGAT ACTGCTCAGT GATCATGATC AATTAAGGCA TCCGTTAATT

GAATAGGAAA GTATATTCAC AGGTGCAATG CAATGATGAC AAGACTACCT

TCAAATCAAT ACATAAGTTC TTTTTTGAAA GCATTGGATT CTGAACCCAA

CTACCCAAAT GCAAAAGACA TGTGCTCTTG CTTGTTTTGC GATATCTACA

CCTTTCTGAA AGATAAAAGT TTAAATGGGT ATTGCTAGCA GATCTATTGT

TTATCTTTTT TTGTTTCTTC ACCAGGTAGC AGTTGCACTA TCTCATGCAG

CTATTCTCGA AGAGTCCATG CGGGCACGTG ATTTACTAAT GGAGCAGAAT

GTTGCCCTGG ATTTAGCTCG AAGAGAGGCT GAGATGGCTA TCCGTGCTCG

CAATGATTTC CTAGCTGTTA TGAATCACGA AATGAGAACA CCCATGAATG

CAATAATAGC CCTTTCCTCC TTGCTTTTGG AAACTGAGCT TACTCCTGAG

CAGCGTCTAA TGGTGGAAAC AGTACTGAAA AGCAGCAATT TGTTAGCAAC

ACTCATCAAT GATGTTCTGG ATCTTTCCAA ACTCGAGGAT GGAAGCCTTG

AACTGGAGAT TAAAGCATTC AATCTTCATG CTGTTTTCAA AGAAGTATGC

ACCACAGCTA ATACTCTTTC TGCTCCAGAT TATAGGTCAC TTTAGCTTTG

CTCCAAGTCA AACTCTAACT TTGACCATGT TTTTTAAAAA AAATATCTTA

ACTTCCACAA AATCAAATAA ATGCACAAAC AAGACATTTC ATGGAGGATT

AATGAAACTG ATTGACATTA TTGTTAGTGT ATATTTCTAT AAGTTTGTCC

AAAGTTAGAA CTTAGGTAAA GGAAGTGACC TATAATTGGT AATAGAGGGA
```

-continued

```
GTATCAAACA TCTAGATACA TGATGCAATA GCTCTAATTC TTATTTGGTA

TTACAGGTGA TGGGTTTCAT TAAACCAATT GCATCTATCA AGAGGCTATC

TGTATCGGTT ATGTTGGCAC CAGATCTGCC GTTATGTGCA ATTGGTGATG

AAAAGAGACT CATGCAAACT ATTCTGAACA TCTCTGGCAA TGCTGTAAAG

TTTACCAAGG AGGGACACAT CACGCTTGTA GCTTCCATTG TGAAGGCTGA

CTCTTTGAGA GAGTTCAGAA CCCCAGAATT TCATCCAACT GCAAGTGATG

AACATTTCTA TTTGAAAGTT CAGGTGATAT TCTAGAAGAG GCTTGTTTGA

ATAATTTTCC TTGAGCTTGT CAATGAGCTC ATGATCTTTC CATAGTATCA

ATAAAACAAG AAGATTTATC TGCAAATAGT TGTATGCACT GTTCCCTCTT

TAATAACAAT AATAACTTAA AGATGACCT GCATGCGTTG TGCAGAGCTC

CAAAATTCAA AAATGAAACT GGAGCCATCC ATTTGGTTGT CCCAAGTAGC

AGTTTTGTAA AACCGAATTG CAGCCTGTCG AAAAATCTCA ACTCTTTCAT

TGTACAACAT TTGTAATCTG TTGTCTTATC TCCTTATGTG TGACTGAATT

TCTCATGCAC TCTGGTTTTG GATCCATCCA CTATGTTCCT CATAATGAAG

TATTTCATGC TTATTTAGTA GCAAAAGACA ATATTTTTC TTGAAAATCC

TCTTAATTAA CACGTGCATT TTCTTGTATG AATCGTTACC TATTCCTTTT

AATCATGTAT CTTGGTAATT AATTGCATTT GCATCATTAA ACCTGGCTCG

ACTCTTGTGT TGCTTGATAG TTCATTTGTC TTGTCTATAA ACTAGGTGGG

TCTCAGCTCT GTATAGGTCC ATGTACAATT TTCCAATTCT TCCTATCAAG

TTTACAAAAA CAGGTGGGGC CTGTCCAGCT GTACCTGACT ATGATTTGGG

GTGGGTGGGG TCTGAATCTT TTACTTTATT CTTATAATCT CATGGTGTAG

AATTTCTGCT GGTTGGGCCT GATGACATTT GGAATCTGAT TACTTCTTTA

CACCATTGTG ACATTAGTTG ACTGTCATTC ACTGCTTTTT ATTTGAGTTG

CCTGGATTGA ATTAGTCTCA GGACTGACAT AGGATAGGAC CTAATATCGC

ATTAGCAAAA GCTAAAATGG TCTAGGATTA GAAGTGCTAT ACCAAATCTT

CCATGAACTC CAGATAGCCC AGAGTCTTTT ATAATGCCAC ACACAGAGCT

TTGGTATGTT GAAAAAAATC ATAGGTCAAC CGAACTAAGT TATCACAACA

TTTACTCAAA CTATATCAGA ATTCAGAAGG TACAGATGCT TACATAAATT

TCATTTTAGT TGATACCACC GGTCCTGGGT TTCATGCTTA CAACTAGAAA

AGGGTTCTAT TTTTTCAGAT TATGAACATA CCATGGAAAC ATGAAGCAGG

GTTTTACTTT TATATATGCT AGCAATTGTT ATCTGTTGTG TTGCTTTACA

TTTCTGTTAC TTACTCTTTT GCAGGTAAAA GATACAGGCT GTGGAGTTAG

TCCTCAGGAT CTACCTCATG TATTCACAAA GTTTGCTCAT CCTCAAAGTG

GAGGAAACCG AGGGTTTAAT GGTAGTGGTC TTGGCCTTGC CATATGCAAG

AGGTAGTTTG ACCTTACAGC TCCTTTCTTG TAGTTCCTTC TGAAAATTGT

GTTCTGGTGT TTTTTGTGAC TCTTGACTTT CTCCTACGCA GCACATTTAT

TTATTTATTT TATGCATTGC CAGTACATGG CTCATTAGTG CTAACCTGGT

CATCAATTCT TATTAGAACT CATCAGCATC TCTGCAAAAT TCTGCGCAGG

TTTGTTAGTC TTATGGGAGG GCACATCTGG ATCGACAGCG AAGGAACCGG

AAGAGGTTGC ACCGCAACAT TCGTCATCAA GCTCGGCGTG TGTGACAACA

CAAACACCTA CCAAAAGCAG CTGGTTCCTC TAATCTGGCC AAGCAGTGCA
```

-continued

```
GACTCCAATT TGTCTGCTCC GAAAGTGCTG CCCGACGGGA GAGGATCTGT

TTCCCTGAAA TCTCGGTACC AAAGAAGCGT ATGAGCTCAG TGTAAATGAT

TGACGGCATA GTGCCAAGTA GGGGATCGAT TAGTGCCATT GTCTAATTTT

GTTTGTAACC CAGTCATAGC AACATATAGT GTACAAATAA TGTAAAGCCA

ATGGAGACTG CAGCTGTGTA TCTGGGTAGC AACGCTGACT TGCTGCATTG

AGTAGTATGT CCTACCAGCG GATTGAATTG CTTGTTCTGG GGTGTGCGGC

GCGCGCCCCG TTGATTGTTC TGTTGTAACT TGTAATCCCA TATTAATCGT

GTAATATGAA ATTCAATGCA AATACACGGT CACAAGCTGT TTTCGGTGCC

CTCGCTCCAT CAGTTGGTTC AGATCGTAGA TGCTGCCAGT TGCATGTGTT

AGATAGGACT GGAAAATAAG CTCGAGGCTT GCGAGCCGGC TCGAGCTCGA

AGTGTTTCGC GAGCCTCGAA CGAGTCGAGC TCCTTCTTTG AGCTCGTTTT

TATAGTGAGC CGAGCCGTCT CGTTCCAGCT CGCGAGCCTT ACAAAAATAA

TTAATTTATA GAATAATAAT GAATATTAGA TAATTTTATG GATAATAGCT

CATTTTTTAG TTTTTGATGA TGAATATATT ATAATTTATA ATTTAAATTA

CTCATAATGT TGAATGATTC TTTGATGATG AATATATTAC AATTTATAAT

TTAAATTACT CATAATGTTG AATGATGATT ATATATTTCA AATTTATATA

ATATTAATTC ACTAAATAGT GCAACAATAA ATACCATAAT ATGGCTCGTG

AGCCGAGCCG GCTCGCGAGC CAATATTGAG CAGAGCAGCC TCTTTCGCTA

GCTCGTGGAA TAGACAAGCC GAGCTCGTTT AGGCAACCTC GGCTCGTTTT

CAGCCCTAGT CTTAGAGTTG TTTGGAACCT CTATAGCTAA TAATTAGTTG

CTAAAATTAG CTTGGGAGGT TCTAAACACC CACCTCTGCT CGGCTCGTTC

AGGCAAGGTC AACTCGGCTC GTCCAGTCCT TAATTTTCAA CACTCAAGTA

TAATTTTAGA TCACTGAATT TGCTATTTTA TTTTCTTCAT ATATTTATTT

TATTATTATT TTATTTTTTT TTCTTATACA CATTTTGGGC CTTAAATATT

ATTAGCACAC TGATTTCTTG TCTATCTATA TCTTTTTGGA CATTTTAAGC

TGCAACTAGT AAACGGGCAT CCCCTGTACG TATGGTATGG GTTAGGACGA

CCCTGCTTCG CTTCAGCGTG AGTGTGGCGC CAATTTTGCA TCAGCGTTTG

CTATCATCGT CACGACGAGA ATGTACGGTG AATATACAAA GCACAACACA

ACAATTGTGT ATATATAGAA TAATGAGAAA AGGCAACCTC AACATACGAT

GCGGACGAGA AAAGAGCAAT TGATGATAGA CTGATACCCA CCACCAGTAC

CACAGTCCAC GCTCCTTTTC TTTTCTTTTT TCCCTCCTTT GTATTGCACA

AATCAGTGAG CGTGCAGTCG ATAAAGACAC ACTTT
```

*Zea mays* ethylene receptor (ethylene response sensor receptor,
ERS1-like); ERS14 coding sequence (cds).
SEQ ID NO: 21
```
ATGGACGGAT GCGATTGCAT AGAGCCACTA TGGCCTACCG ATGATCTTCT

CGTCAAGTAT CAGTACATCT CAGACTTCTT CATAGCCCTT GCGTACTTCT

CGATTCCATT GGAGCTCATA TATTTTGTGA AGAAGTCGTC CTTCTTCCCA

TACAGATGGG TCCTGATCCA GTTGGTGCG TTTATAGTTC TTTGTGGGGC

AACCCATCTG ATAAACCTGT GGACGTTCAC CACACATACA AAGACCGTTG

CGATGGTCAT GACCATAGCG AAGATTTCTA CAGCAGTCGT GTCCTGTGCA

ACTGCTTTGA TGCTCGTTCA TATCATTCCC GACTTGTTGA GCGTGAAAAC
```

-continued

```
TAGGGAGTTG TTCTTGAAGA ATAAAGCTGA GGAGCTTGAT AGAGAGATGG

GACTTATAAG GACGCAAGAG GAGACTGGTA GACATGTTAG GATGCTTACA

CATGAAATCA GAAGTACTCT TGATAGACAT ACAATTTTGA AGACTACTCT

CGTTGAGCTA GGAAGGACCT TGGGTCTGGA AGAATGTGCA TTGTGGATGC

CATCTCGAAG TGGCTCAAGC CTTCAGCTTT CTCATACTTT GCGCCACCAG

ATTACTGTTG GATCATCGGT GCCAATGAAT CTTCCTGTCG TCAATCAAGT

GTTCAGTAGC AACCGGGCAA TCATAATACC CCACACATCT TCTTTGGCGC

GGGTTCGACC TCTTGCAGGG CGATATGTTC ACCAGAAGT GGCCGCAGTC

CGTGTACCTC TTCTACATCT TTCAAACTTT CAAATAAATG ATTGGCCTGA

GCTCTCAGCA AAAAGCTTTG CAATCATGGT TTTGATGCTT CCATCTGATA

GTGCTAGAAA ATTGCATGTG CATGAATTGG AGCTGGTTGA GGTCGTTGCT

GATCAGGTAG CAGTTGCACT ATCTCATGCA GCTATTCTCG AAGAGTCCAT

GCGGGCACGT GATTTACTAA TGGAGCAGAA TGTTGCCCTG GATTTAGCTC

GAAGAGAGGC TGAGATGGCT ATCCGTGCTC GCAATGATTT CCTAGCTGTT

ATGAATCACG AAATGAGAAC ACCCATGAAT GCAATAATAG CCCTTTCCTC

CTTGCTTTTG GAAACTGAGC TTACTCCTGA GCAGCGTCTA ATGGTGGAAA

CAGTACTGAA AAGCAGCAAT TTGTTAGCAA CACTCATCAA TGATGTTCTG

GATCTTTCCA AACTCGAGGA TGGAAGCCTT GAACTGGAGA TTAAAGCATT

CAATCTTCAT GCTGTTTTCA AGAAGTAAT GGGTTTCATT AAACCAATTG

CATCTATCAA GAGGCTATCT GTATCGGTTA TGTTGGCACC AGATCTGCCG

TTATGTGCAA TTGGTGATGA AAAGAGACTC ATGCAAACTA TTCTGAACAT

CTCTGGCAAT GCTGTAAAGT TTACCAAGGA GGGACACATC ACGCTTGTAG

CTTCCATTGT GAAGGCTGAC TCTTTGAGAG AGTTCAGAAC CCCAGAATTT

CATCCAACTG CAAGTGATGA ACATTTCTAT TTGAAAGTTC AGGTAAAAGA

TACAGGCTGT GGAGTTAGTC CTCAGGATCT ACCTCATGTA TTCACAAAGT

TTGCTCATCC TCAAAGTGGA GGAAACCGAG GGTTTAATGG TAGTGGTCTT

GGCCTTGCCA TATGCAAGAG GTTTGTTAGT CTTATGGGAG GGCACATCTG

GATCGACAGC GAAGGAACCG GAAGAGGTTG CACCGCAACA TTCGTCATCA

AGCTCGGCGT GTGTGACAAC ACAAACACCT ACCAAAAGCA GCTGGTTCCT

CTAATCTGGC AAGCAGTGC AGACTCCAAT TTGTCTGCTC CGAAAGTGCT

GCCCGACGGG AGAGGATCTG TTTCCCTGAA ATCTCGGTAC CAAAGAAGCG

TA
```

Zea mays ethylene receptor (ethylene response sensor receptor, ERS1-like); ERS14 amino acid sequence.

SEQ ID NO: 22

```
MDGCDCIEPL WPTDDLLVKY QISDFFIAL AYFSIPLELI YFVKKSSFFP

YRWVLIQFGA FIVLCGATHL INLWTFTTHT KTVAMVMTIA KISTAVVSCA

TALMLVHIIP DLLSVKTREL FLKNKAEELD REMGLIRTQE ETGRHVRMLT

HEIRSTLDRH TILKTTLVEL GRTLGLEECA LWMPSRSGSS LQLSHTLRHQ

ITVGSSVPMN LPVVNQVFSS NRAIIIPHTS SLARVRPLAG RYVPPEVAAV

RVPLLHLSNF QINDWPELSA KSFAIMVLML PSDSARKLHV HELELVEVVA

DQVAVALSHA AILEESMRAR DLLMEQNVAL DLARREAEMA IRARNDFLAV
```

```
MNHEMRTPMN AIIALSSLLL ETELTPEQRL MVETVLKSSN LLATLINDVL

DLSKLEDGSL ELEIKAFNLH AVFKEVMGFI KPIASIKRLS VSVMLAPDLP

LCAIGDEKRL MQTILNISGN AVKFTKEGHI TLVASIVKAD SLREFRTPEF

HPTASDEHFY LKVQVKDTGC GVSPQDLPHV FTKFAHPQSG GNRGFNGSGL

GLAICKRFVS LMGGHIWIDS EGTGRGCTAT FVIKLGVCDN TNTYQKQLVP

LIWPSSADSN LSAPKVLPDG RGSVSLKSRY QRSV
```

*Zea mays* ethylene receptor (ethylene response sensor receptor, ERS1-like); ERS14 forward primer sequence.
SEQ ID NO: 23
```
GAGTTAGTCCTCAGGATCTACCTCATGT
```

*Zea mays* ethylene receptor (ethylene response sensor receptor, ERS1-like); ERS14 reverse primer sequence.
SEQ ID NO: 24
```
CAACTCAATCCGCTGGTAGGACATACT
```

*Zea mays* ethylene receptor (ethylene response sensor receptor, ERS1-like); ERS25 genomic sequence.
SEQ ID NO: 25
```
GACGCCGAGT TCGATGTGGA CATCCATCGC TCGGTGGACG ACCACGATAT

CCATAGCGTG CTGGACTACC GCCGTCTGCG CGAGGCCATC GTCGAGGAAT

GCACGCAGGC GCATGTGAAC CTGATCGAAA CCCTGTCCGA ACAAGTCGCC

GCGCGCCTGT TGGCCGACTT CCAGGAAATC CGCTCGTTGC GCTTGCGCAT

CAGCAAGCCC ATGGCCTTTT CCGACTGCGC GGCGGTAGGC GTGGAAATCC

AGATCACCCG CTGACCATGA ACGATATTGC TCCGCCCCCC GCCGTCCGCT

CCCCCGAGGT CCGCTATCGC ACCGAGGCCG AGGAAAAGGC CCGCCACGAA

GGCAACAAGC TGACCAAGCG CCTGGCCCGC GAAACCACGC GCGCGCTGTC

CGACTACAAC ATGATTGAAG AAGGCGACCG CGTGATGGTC TGCCTGTCGG

GCGGCAAGGA TTCCTATGCC ATGCTGGACA TCCTGCTGCA ATTGCAGAAG

CGCGCGCCGT TCAAGTTTGA ACTGATCGCC GTCAACCTGG ACCAGAAGCA

GCCGGGCTTT CCCGACCACA TCCTGCCCCA GTACCTGAAA GACCTGGGCG

TGCCCTTCCA CATCGAGACG CAGGACACGT ATTCCATCGT CACGCGCGTG

CTGGAAGAAG GCAAGACGAT GTGCTCGCTC TGTTCGCGCT TGCGTCGCGG

CATTCTGTAC CGCGTCGCCT CGGAACTGGG CGCCACCAAG ATCGCGCTGG

GCCACCACCG CGACGACATC CTGGCCACGT TCTTCCTGAA CCTGTTCTAT

GGCGGCAAGG CCAAGGGCAT GCCGCCCAAA CTGGTGTCGG ACGACGGCCG

CCACACCGTG ATCCGTCCGC TGGCCTATGT GGCCGAAACG GACCTGATCG

CCTATGCGGA GTTGAAGCAA TTCCCCATCA TTCCGTGCAA CCTCTGCGGC

TCGCAGGAAA ACCTGAAGCG CAAGGAAGTG GGCCGGATGA TCTATATATA

GTCTTAGGGT TGTCATGCGA CCTAGCAAAT AAAGAGGATG ACTCTGGTCA

GGAACGGATA TAAAGCATCG GGCCACCTCG TTCGTGGCTT AATCCATATT

TTTTTATTTA TATTTGTTAT CTTTAGACTA AAATGTATTG GACTTTTTTT

TGCTTGATCG GATGGGATTT TTTTTCATGT CGTGGTTGTG GTCGCATGAA

GTCATGAAGA TGCTTGCTGG CATGTTGCTG TTGGGTAGCC CATCTCTGCA

TGCCATTGCC CACTCTTACA GAACTGTAGT AACAACAGCA GCTGGTGTAG

AGTAGCTGCA GTGAGCCAGT GAACGCAATG CTTAGACGAC TTACAGAACA

GCGCCGGACT GCCTTCACCC TGCCTATTCT TTCTTCCCGT TCACCCCGCG
```

```
TGCACGCTCT TTCCCTTCCT CGTGCCGACG ACCGGGCGAC CGCCGCGCCC
CGGCCCGCGC CCCCTTGTCT CGGGCCACTC GCCGGCAACG AGCAGCCACC
AGGTATGCCA CCCCCTTCTC CCCCCTTCCT GCTGTACGAA ACCGAGCACC
CAAACCCTAA CTTAAGCTTA TTTGGCTATT TACATTCGGA TCTGATCTAG
TTACAGGAGC ACACACGTAT TATCCCTACT AAATCCGATT TTAGTGGAAA
AAGCTGTCGG GTGTACATGT GTCCACCCAT GTCCTTTACG AGTTCGGCCC
TTGGCCGAGG TCCGTTTGGA ATTGGAAATG GGAATCAGAG GGGCGAATGC
CGAATGGGCA TGTCTTGCGC AATTTCCATG CTCTGCTAGT AGGCGTGCTG
CGTTCATGAG CTCATACTAT CCAAATGCCA TTCGCTACGC ATTTGCTTCT
ATTTGAGATC GGGAAACGGT GTGTCAAAAA CGATTTATCA ATATGTTTCT
TCTTCTACAG GAAATGTTGT GAGGACTGAT GCAATAACTA AGCTTGCTGG
ATGGACGGAT GTGATTGCAT CGAGCCACTA TGGCCTACCG ATGATCTCCT
TGTCAAGTAT CAGTACATCT CAGACTTCTT CATAGCCCTC GCGTACTTCT
CTATTCCGTT GGAGCTCATA TATTTCGTGA AGAAGTCGTC CTTCTTCCCG
TACAGATGGG TCTTGATCCA GTTTGGTGCG TTTATAGTTC TCTGTGGGGC
AACCCATCTG ATAAACCTGT GGACGTTCAC CACACATACA AAGACCGTTG
CGATGGTCAT GACCATAGCA AAGGTTTCTA CAGCAGTTGT GTCCTGTGCA
ACTGCTTTGA TGCTTGTTCA TATCATCCCC GACTTATTGA GCGTGAAAAC
TAGAGAGTTG TTCCTGAAGA ATAAAGCTGA AGAGCTTGAC AGAGAGATGG
GACTGATAAG GACGCAGGAG GAGACCGGTA GACATGTTAG GATGCTTACA
CATGAAATCA GAAGTACTCT TGACAGGCAT ATGATTTGA AGACTACTCT
TGTTGAGCTA GGAAGGACCT TGGGTCTGGA GGAATGTGCA TTGTGGATGC
CATCTCGAAG TGGTTCAAGC CTTCAGCTTT CTCATACTTT GCACCACCAG
ATTACTGTTG GATCATCGGT GCCAATTAAT CTTCCTGTCA TCAATCAAGT
GTTCAGTAGC AACCGGGCAA TTATAATACC CCACACATCT CCTTTGGCGC
GGATTCGACC TCTTACAGGG CGATATGTTC CACCAGAAGT GGCTGCAGTC
CGTGTACCTC TTCTCCACCT TTCAAACTTC CAAATAAATG ATTGGCCTGA
GCTTTCGGCA AAAAGCTTTG CAATCATGGT TTTGATGCTT CCATCTGATA
GTGCAAGAAA ATGGCATGTA CATGAATTGG AGCTGGTTGA GGTTGTTGCT
GATCAGGTTC GTGCTGTATC TCTGTCTATG GTTACTATAA CATGGTACCT
TCATCCTGAA AATGATGTAA ATTTACTTGT CTCTATTCAA ACAATCTATA
CTTTGATTAA GTTTATTAAA AGATTATCAA TAAATATGAC ATCAGATAGG
TATATTTTGA AAATATATTC CATGACATAT TTAACAATAC TTATTTGATA
GTGTAAATAT TGCTATTTTT AAATAAATTT GGTCACTGTT TTACTTGGCG
CTATGCTAGA ATTACATTCT TTTCTGGATG GAGGGAGTAT ATGCTTGTAG
GAGAGGAAAA ACATGTTTAC ATCTTTCAAA TTCATATGAT ACTGCTCAGT
TATCATGATC AGTCAATTAA GGCATCCGTT AATTGAACAG GAAAGTATAT
TCACAGGTGC AATGTAATGA TGACAAGAAT ACCTTTAAAT CAATACATAA
TCTCTTTTTT TGAAAGCATA GGATTCTGAA CCCAACTACC GAGCCACAAA
AGACACATGC TCTTGCTGTT GCGCAATATC TACACCTTTC TGAAGGTTAA
```

-continued

```
AAGTTTAAAT TGGTAGTGCT AGCAGGTCTA TTGTTTATCT CCTTTTTTTG

TTTCTTCATC AGGTAGCAGT TGCACTATCT CATGCGGCTA TTCTTGAAGA

GTCCATGCGA GCACGTGATT TACTAATGGA GCAGAATGTT GCCCTGGATT

TAGCTCGAAG AGAGGCTGAG ATGGCTATCC GTGCTCGCAA TGATTTTCTA

GCTGTTATGA ATCACGAAAT GAGAACACCC ATGAATGCAA TAATAGCCCT

TTCCTCCTTG CTTTTGGAAA CTGAGCTTAC TCCTGAGCAG CGTCTAATGG

TGGAAACAGT ACTGAAAAGC AGCAATCTGT TAGCAACACT CATCAATGAT

GTGCTAGATC TTTCCAAACT CGAGGATGGA AGCCTTGAAC TGGAGATTAA

AGCATTCAAT CTTCATGCTG TTTTCAAAGA AGTATGCACC ATCAGTTTTC

TAATACTCTT TCCGTTCCAG GTTCTAGGTT ACTTTAGCTT TGCTCTAAGT

CAAACTCTAA CTTTGGCCAA GTTTTTAGAA AAATATGTCA ACTTCTACAA

ATTAAAATAA ATGCACTAAC AAGACATGTT ATGGAGAATT CATGTGATGT

TATTGTTGGT GTATTTTTCT ATAAGTTTGT TCAAAGTTAG AGAAATTGGA

CTTAGGTAAA GAAAGCGACT TGTAATTAGT AACAGAGGGA GTATCAAACA

TCTAGATACA CGGTGCAACA ACTAAAATTC CTATTTGGTA TTACAGGTGA

TGGGTTTCAT TAAACCAATT GCATCTATCA AGAGGCTATC TGTATCGGTT

ATGTTGGCAC CAGATTTGCC GTTATGTGCC ATTGGTGATG AAAAGAGACT

CATGCAAACT ATTCTGAACA TCTCTGGCAA CGCTGTAAAG TTTACCAAGG

AGGGACACAT CACACTTGTA GCTTCCATTG TGAAGGCTGA CTCTTTGAGA

GAGTTCAGAA CCCCAGAATT TCATCCAACT GCAAGTGATG ACCATTTCTA

TTTGAAAGTT CAGGTAATAT TCTAGAAAGG CTTGTTTGAA TAATCTTGGA

CTTGTCAATG AGCTCATGGT CTTTCCATAC TATCAATAAA ACAAATAGAA

TTTTTTGCAA ATGGTTGTAT GCATTGTCCC TCTTTAATAA CAATAATAAC

TTAAAAAATG ACCTGTATGT GTTGTGCAGA GCACCAAATT TCAAAAATGA

AACTGGAGCC ATCCATTTGG TTGTCTCAAG TAGCAGTTTA GTGAACCCTA

ATTGCAGCTT GTCAAACAAT CTCAACTATT TCATTGTACA ACATTTATAA

TCTGTTGTCT TGTCTTCTTA TTTGCGACTG AATTTCTCAT GCACTCTGGT

TCTGGATTCA CTGTGTTCCT CACATTGAAG TATTTCATGC TTATTCAGTA

GTAGATGATA TTTTTTTCAT GAAAATCCTC TTGATTAATA TCTGCGTTTC

CTTGTATGAT TTGTTACATA TTTCCTTTAA TTATGCGTCT TGGTCATTAA

TTGCATATGC ATCATAACTT GGATAGACCC TTAAGTTGTT TGATAGTCCA

TTTGTTTATA AACTATGTGG TCGTCAGCTC TGTATAGGTC CATGTACAAT

TTTCCAATTC TTTGTACCAA GTTTACAAAA GCAGACGGTA CCTGTTCAGA

TGTACCTGAC TGATGTGTGT GTGTGTGGGG GGGGAGGGG GTCTGAATCC

TTTTCTTTGT TATAATCTCA AGGAGTCAAG GTGGTGTGGA ATTTCTACCA

GTGTTGGGCA TGATGATTTT TGGAATCCGA TTTCTTTACG CCACTGTGAC

CTTAGTTCAG TAGTCATTTG TTGCGTTTTA TCTGAGTTGC CTGGATTGAA

TTAGTCGCAG GACTGACATA GGACTAGGAC CTAAGGCCGC ATTAGCAAAA

ACTCAGATGG TCTAGGATCC GTTGACCTGC AGGTCGACCC AGATCATAAG

TGTTATACCA AATCTTCCAT GAGCTCCAGA TCAGCCCTGA TCCTTGTATA

ATGCTAACAC AAAGCTTTCG TGTGTTGAAA AACATTCCTA GGTCAACCAT
```

```
ATTAAGTTAT CACAACGTTT ACTCAATATA TCACAAGGCG CAGATGCTTA
TATTTGCAGA TTATGAACAT GCCATGGACA AACGAAGCAG AGTTTTACTT
CTATGCTTAG CAAGTCTTAT CTATTGTGTT GCTTTACATT CTCTGTTACT
TCACACTTCT GCAGGTAAAA GATACAGGCT GTGGAATTGG TCCACAGGAT
CTACCTCATG TATTTACAAA GTTTGCTCAT CCTCAAAGCG GAGGAAACCG
AGGGTTTAAT GGTAGTGGTC TTGGCCTTGC CATATGCAAG AGGTAGTTCG
ATCTTACATC TCCTTTCTGT AGTTCCTTCT GAATCTGGTG TTAAGGTGCT
GTTTTTGGTG ACTCGAAGTC TTCCTATGCA GCACAATTAT TTATTTATTT
TGTTTAATGC ATTGCCAGTA TATAGGGATA CCTCGGTCAT CAATTCTCAT
TAGAACTCAT CGGCATCTCT GCAAATTTCT GGTGCAGGTT TGTTAGTCTC
ATGGGAGGGC ACATCTGGAT TGACAGCGAA GGAACCGGAA GAGGTTGCAC
CGCAACATTC GTCGTCAAGC TCGGCGTGTG TGACAACACA AACACCTACC
AGCAGCAGCT GATCCCTCTA GTATGGCCAA GCAGCGCAGA CTCCGATTTG
CGTGCTCCGA AACCTCTTCC GGACGGGAGA GGATCTACTC CCTTGAAATC
TCGGTACCAA AGGAGCGTAT GAGCCTAGTG TAAATGATTG ACGGCATAGT
GCCAAGTAGG GGACCGATTA GTGCCACCGT CTAATTTTGT TTGTAACCCT
GTCATAGCAG GCATATGATG TACAAATACT GTAAAGCAAA TGGAGACTGC
GGCCGTGTAT CTGGGTGGCA ACGCTGACTT GCTGCATTGA GTGGTATATA
CATATGCTAC CAGCGGATTG AATTGCTT
```

*Zea mays* ethylene receptor (ethylene response sensor receptor, ERS1-like); ERS25 coding sequence (cds).

SEQ ID NO: 26

```
ATGGACGGAT GTGATTGCAT CGAGCCACTA TGGCCTACCG ATGATCTCCT
TGTCAAGTAT CAGTACATCT CAGACTTCTT CATAGCCCTC GCGTACTTCT
CTATTCCGTT GGAGCTCATA TATTTCGTGA AGAAGTCGTC CTTCTTCCCG
TACAGATGGG TCTTGATCCA GTTTGGTGCG TTTATAGTTC TCTGTGGGGC
AACCCATCTG ATAAACCTGT GGACGTTCAC CACACATACA AAGACCGTTG
CGATGGTCAT GACCATAGCA AAGGTTTCTA CAGCAGTTGT GTCCTGTGCA
ACTGCTTTGA TGCTTGTTCA TATCATCCCC GACTTATTGA GCGTGAAAAC
TAGAGAGTTG TTCCTGAAGA ATAAAGCTGA AGAGCTTGAC AGAGAGATGG
GACTGATAAG GACGCAGGAG GAGACCGGTA GACATGTTAG GATGCTTACA
CATGAAATCA GAAGTACTCT TGACAGGCAT ATGATTTTGA AGACTACTCT
TGTTGAGCTA GGAAGGACCT TGGGTCTGGA GGAATGTGCA TTGTGGATGC
CATCTCGAAG TGGTTCAAGC CTTCAGCTTT CTCATACTTT GCACCACCAG
ATTACTGTTG GATCATCGGT GCCAATTAAT CTTCCTGTCA TCAATCAAGT
GTTCAGTAGC AACCGGGCAA TTATAATACC CCACACATCT CCTTTGGCGC
GGATTCGACC TCTTACAGGG CGATATGTTC ACCAGAAGT GGCTGCAGTC
CGTGTACCTC TTCTCCACCT TTCAAACTTC CAAATAAATG ATTGGCCTGA
GCTTTCGGCA AAAAGCTTTG CAATCATGGT TTTGATGCTT CCATCTGATA
GTGCAAGAAA ATGGCATGTA CATGAATTGG AGCTGGTTGA GGTTGTTGCT
GATCAGGTAG CAGTTGCACT ATCTCATGCG GCTATTCTTG AAGAGTCCAT
GCGAGCACGT GATTTACTAA TGGAGCAGAA TGTTGCCCTG GATTTAGCTC
```

```
GAAGAGAGGC TGAGATGGCT ATCCGTGCTC GCAATGATTT TCTAGCTGTT

ATGAATCACG AAATGAGAAC ACCCATGAAT GCAATAATAG CCCTTTCCTC

CTTGCTTTTG GAAACTGAGC TTACTCCTGA GCAGCGTCTA ATGGTGGAAA

CAGTACTGAA AAGCAGCAAT CTGTTAGCAA CACTCATCAA TGATGTGCTA

GATCTTTCCA AACTCGAGGA TGGAAGCCTT GAACTGGAGA TTAAAGCATT

CAATCTTCAT GCTGTTTTCA AAGAAGTAAT GGGTTTCATT AAACCAATTG

CATCTATCAA GAGGCTATCT GTATCGGTTA TGTTGGCACC AGATTTGCCG

TTATGTGCCA TTGGTGATGA AAAGAGACTC ATGCAAACTA TTCTGAACAT

CTCTGGCAAC GCTGTAAAGT TTACCAAGGA GGGACACATC ACACTTGTAG

CTTCCATTGT GAAGGCTGAC TCTTTGAGAG AGTTCAGAAC CCCAGAATTT

CATCCAACTG CAAGTGATGA CCATTTCTAT TTGAAAGTTC AGGTAGTAAA

AGATACAGGC TGTGGAATTG GTCCACAGGA TCTACCTCAT GTATTTACAA

AGTTTGCTCA TCCTCAAAGC GGAGGAAACC GAGGGTTTAA TGGTAGTGGT

CTTGGCCTTG CCATATGCAA GAGGTTTGTT AGTCTCATGG GAGGGCACAT

CTGGATTGAC AGCGAAGGAA CCGGAAGAGG TTGCACCGCA ACATTCGTCG

TCAAGCTCGG CGTGTGTGAC AACACAAACA CCTACCAGCA GCAGCTGATC

CCTCTAGTAT GGCCAAGCAG CGCAGACTCC GATTTGCGTG CTCCGAAACC

TCTTCCGGAC GGGAGAGGAT CTACTCCCTT GAAATCTCGG TACCAAAGGA

GCGTA
```

Zea mays ethylene receptor (ethylene response sensor
receptor, ERS1-like); ERS25 amino acid sequence.
SEQ ID NO: 27

```
MDGCDCIEPL WPTDDLLVKY QYISDFFIAL AYFSIPLELI YFVKKSSFFP

YRWVLIQFGA FIVLCGATHL INLWTFTTHT KTVAMVMTIA KVSTAVVSCA

TALMLVHIIP DLLSVKTREL FLKNKAEELD REMGLIRTQE ETGRHVRMLT

HEIRSTLDRH MILKTTLVEL GRTLGLEECA LWMPSRSGSS LQLSHTLHHQ

ITVGSSVPIN LPVINQVFSS NRAIIIPHTS PLARIRPLTG RYVPPEVAAV

RVPLLHLSNF QINDWPELSA KSFAIMVLML PSDSARKWHV HELELVEVVA

DQVAVALSHA AILEESMRAR DLLMEQNVAL DLARREAEMA IRARNDFLAV

MNHEMRTPMN AIIALSSLLL ETELTPEQRL MVETVLKSSN LLATLINDVL

DLSKLEDGSL ELEIKAFNLH AVFKEVMGFI KPIASIKRLS VSVMLAPDLP

LCAIGDEKRL MQTILNISGN AVKFTKEGHI TLVASIVKAD SLREFRTPEF

HPTASDDHFY LKVQVKDTGC GIGPQDLPHV FTKFAHPQSG GNRGFNGSGL

GLAICKRFVS LMGGHIWIDS EGTGRGCTAT FVVKLGVCDN TNTYQQQLIP

LVWPSSADSD LRAPKPLPDG RGSTPLKSRY QRSV
```

Zea mays ethylene receptor (ethylene response sensor
receptor, ERS1-like); ERS25 forward primer sequence.
SEQ ID NO: 28
GAGTTAGTCCTCAGGATCTACCTCATGT Zea mays ethylene receptor (ethylene response sensor
receptor, ERS1-like); ERS25 reverse primer sequence.
SEQ ID NO: 29
CAATTCAATCCGCTGGTAGCATATGT Zea mays ethylene receptor (ethylene resistant, ETR2-like);
ETR9 genomic sequence.
SEQ ID NO: 30

-continued

```
TATACACCAC AGCAAAATGG TGTGGTAGAG AGGAAGAACA GGACGCTGAT

CGACATGGCG AGAATGATGC TTGGAGAGTT CAAGACGCCC GAGCGGTTTT

TGTCGGAAGA TGTGAACACA GCCTGCCATG CCATAAACCA GCTCTATCTG

CATCGTCTCC TCAAGAAGAC CTCCTACGAA CTCCTTATCG GTAACAAACC

CAATGTCTCT TACTTTCGTG TATTTGGGAG CAAATGCTAC ATTCTGGTGA

AGAAAGGTAG ACATTCTAAA TTTGCTCCCA AAGCAGTAGA AGGGTTCTTA

CTAGGGTATG ACTCAAATAC AAAGGCGTAT AGAGTCTTCA ACAAATCATC

GGGATTAGTT GAAGTCTCTA GCGACATTGT ATTTGATGAG ACTAATGGCT

CTCCAAGAGA GCAAGTTGAT CTTGATGATG TAGATGAAGA AGAAATAACG

ACGACCGCAA TGCGCACGAT GGCGATAGGC GATGTGCGAC CACAGGAACT

ACAGGAACAA GATAAACCAT CTTCCTCGAC AATGGTGCAT CCCCCAACTC

AAGACGTTGA ACAAGTACAT CAAGAAGAGG GGCAAGATCA AGGGGGAGCA

CAAGAAGAAC AGGTTATGGA GGAAGAAGCA CCATGGGCCC CTTCAACTCA

AGTCCGAGCA ACGATCCAAA GACATCACCC CGTCGATCAA ATTCTGGGTG

ACATCATCAA GGGAGTAACT ACTCGCTCAC GTTTAGCTAA TTTTTGTGAG

CATTACTCGT TGGTCTCTTC TATTGAGCCT TTCAGGGTAG AAGAGGCCTT

GCAGGATCCG GACTGGGTGT TGGCCATGCA GGAAGAGCTC AACAACTTCA

AGAGAAATGA AGTCTGGAGC CTGGTGCCAC GTCCAAAGCA AAATGTTGTG

GGAACCAAGT GGGTGTTCCG GAACAAGCAA GATGAGCACG GGGTGGTGAC

AAGAAACAAG GCTCGACTTG TGGCAAAAGG TTATGCCCAA GTCGCAGGTT

TGGATTTCGA GGAGACTTTT GCTCATGTTG CTAGGCTAGA GTCAATTAGG

ATTTTATTAG CCTATGCTGC TCACCACTCT TTTAGGCTGT TCCAAATGGA

CGTGAAGAGC GCTTTCCTCA ACGGGCCAAT TAAGGAGGAG GTATACGTGG

AACAACCCTC TGGCTTTAAG GATGACAGGT ATCATGACCA TGTGTATAAG

CTCTCTAAGG CGCTCTATGG ACTTAAGCAA GCCCCAAGAG CATGGTATGA

ATGCCTTAGA GATTTCTTAA TTGCTAATGC CTTCAAGGTT GGGAAAGCTG

ATCCCACTCT TTTTACCAAG ACTTGTGATG GTGATCTCTT TGTGTGCCAA

ATTTATGTCG ATGACATAAT ATTTGGTTCT ACTAATCAAA AGTCTTGTGA

GGAGTTTAGC AGGGTGATGA TGCAAAAGTT CGAGATGTCG ATGATGGGCG

AGTTGACCTA CTTCCTTGGG TTCCAAGTGA AGCAACTCAA AGACGGCACA

TTCATCTCCC AAATGAAGTA CACTCAGGTC TTCTCAAGAG GTTTGGGATG

AAGGACGCCA AGCCCGCGAA GACACTAATG GGAACTGACG GCATATTGA

CCTCAACAAA GGAGGTAAGT CCGTTGATCC GTAGCCAGCC CACGTGTAGA

CGGTTATGGT GCTAGTACCG GTGCCAACGC TGTGTTTCTT GGCGGGCGTT

GCTGCTCCTC CTCCGCTTGA GGATTGCTGC TGCATCCGGC AGGAGGGATG

GTCGGAGGCG GAAGGTGGGC GGCTTTTGAC ACTCCTCCGT TCTTCTTCGT

TCTACCAATT CAATAACTAT GTTTGGATTT ATCGGAGGGG TTTATCGGAT

TTGGCTAAAT CCCCTACTGC CCGAATTTTG GCGGACTGGT GATTCGATTT

TGGCCGATAG ATAGATTTCG ATGCTACTTT TAGGAAAGAC TAATCTTCAC

AGGGGGGCCT ATCCGTCCCA AAGCAACGAT TTGCTTTACG CCAGATCTTG

ATTTTGTGTG CCGCAGTTTG ATTAACTGAA AATCTGTGAT GGCCGTCTGG
```

-continued

```
TGAATGCAGG AGCGTCGGCA CCCGCAGCGT GGAATCGACG ACGGGCGCCT
CCAGTCGGTT CAGAAATGCG CAAATGCGCG TCTGAATGAA GCCTGGTTGG
AGGTGGTAGA CCCGATGGTG GTGGGAACGG CACTGCTGCG CGGGGTTTCC
TCCGCGTGGA TCCTCCTGTT CCTCTCCTCC CTGCTCCTCT CGCCGTCAGC
GGCGTCTGTC GATTTCGGCC ACTGCGGCGG CTGCGACGAC GCCGACGACG
GCGCCCTCTC CAGCACCTAT AACATCCTGC AATGCCAGAA GGTCAGCGAC
TTCCTCATCG CCGCGGCCTA CTTCTCCATC CCGCTCGAGC TGCTCTACTT
CGCCACCTGC TCCGACCTCT TCCCCCTCAA ATGGATCGTG CTGCAGTTCG
GCGCCTTCAT CGTGCTCTGC GGCCTCACGC ACCTCATCAC TGTGTTCACC
TACGAGCCGC ACTCCTTCCA CCTCGTACTC GCCCTTACCG TCGCCAAGTT
CCTGACGGCA CTGGTCTCCT TCGCGACGGC CATCACCCTG CTGACGCTGA
TACCACAGCT CCTGAGGGTG AAGGTCAGGG AAAACTTCCT GATGAACAAG
GCGCGTGAGC TGGACCGGGA GGTGGGGAGG ATGAAAAGGA AGAAGAGGC
GAGCTGGCAT GTGCGCATGC TCACACAGGA GATCCGCAAG TCGCTCGACA
GACATACCAT CTTGTACACC ACCATGGTTG AGCTCTCGAA GGCACTGGAA
CTGCAGAATT GTGCTGTCTG GATGCCTGAT GAGACCAGGA GCACGATGAT
CTTAACACAT CAGCTGAGGG AAAGGGATAT AATGGACCCA CAGAAACACT
CGATTCCTAT TGATGATCCG GATGTTCAAG AAATAAAGGC AACCAAGGAT
GCAAAAGTTC TTGGCCCAGA TTCGGCGCTA GGGGTTTCTA GCCGAAGCAA
GCATGAAGCA GGGCCTGTGG CTGCAATAAG GATGCCGATG TTAAGGGTGT
CAAATTTCAA AGGAGGGACT CCGGAAGTGA TGCAGACGAG CTATGCTATC
TTGGTTCTGG TTTTGCCTAA TGATGGTTCA TTAGGGTGGG GTCGAAGAGA
GTTGGAGATT GTTGAGGTAG TTGCTGACCA AGTTGCAGTC GCTCTGTCAC
ATGCTGCACT CCTAGAGGAG TCTCAGCTGA TGCGAGAGAA GCTTGCCGAG
CAGCATAGGG ACTTGCTGCA GGCAAAGGAT GAAGCCATGA GGGCAGGGGA
CGCTAGGAAT TCCTTCCAGA CTGCAATGTA CGATGGAATG CGAAGGCCAA
TGCACTCAAT CCTTGGTCTC GTCTCAATGA TGCAACAGGA GAGCATGAAT
CCAGAGCAAA GGCTTGTGAT GGATGCCATT GCCAAGACAA GCAGTGTTGC
ATCCACACTG ATGAACGATG TGATGCAAAC ATCGACAATG AACTGTGAGC
ACTTGTCTTT GGTCAGGAGG CCGTTCAACC TTCATTCCTT CATTAAAGAA
GTTGTTGGAG TGGTCAGATG TCTAACTGGT TGCAAGGGTG TGGAGTTTGA
GTTTCAAGTG GAGAATTCTT TGCCAGAAAG GATCATTGGT GATGAGAAGA
GAGTCTTCCA TATTGTCCTG CACATGGTAG CACTCTAAC AGACCGATGT
AATGCTGGCT GTATCTCATT ATATGTAAAT GTCCATAATG AGGTTGAAGA
TAGGCATAAT CATGACTGGA TGCTGCGAAG AGCAAACTTC TCTGGGGCT
ATGTATGTGT GAAATTTGAG ATTAGGATTA GAAAATCAAA GGGCTATCTG
TTGAGTTCAT CAAGCAGTCA GATAAGTCAG GGATCCAAAC CCAACAATTC
TGAGATGGGG CTTAGCTTCA ATATGTGCAA GAAGATTGTG CAGGTAAATC
AAAATAATAG AATATCTTAA GCATTTATAC CCGCAAATTT TTTTGTACAG
CTAGGCACTA GCAGCTTAGA CTTGGCCGTC ACATAGATAG TTTGCTATAC
```

-continued

```
ACCAATTGAA CTGCCAAACT ACAGAATGTG TTTAGTGGCT ATAGTGTGGC

CTTTTTGTGC AAGTGCTTGG AATATTTATT ATCTCACCTC AAACTGGGCA

TACTGAGAGG ACATATTGGT CCTTATGTTG AACTTACGTT TTAGTCATAA

CTATTTTTAT GGTATTTCTT CCGTAGTATG TGTGACTTGC ATAGATATAT

TTAATTGGTA TGCTTGTAGT AGCCCGAACC TCAGCGACTC TATTTGATTG

TTATGTTTTG GTTTGCAATT TGTTCATCCA GTTGTGGAAG TGGCCAATGT

ATACTTGATT TGATGTGCAA TCATTAGTGT GCTTACTGAT ACGAGCCCTC

CTTTGTGCTG CAGATGATGA ATGGCAATAT TTGGTCAGTA TCAGATTCTA

AAAGCATCGG AGAAACTATC ATGCTAGTCC TCCAGTTCCA GTTGGAACCT

GTGACTCCGG TCTCTGGAGC GTCCTCAGAT TTGTACAGAT CATCCGCAAT

TCCCAACTTT AATGGGCTCA GAGTCCTCCT TGCGGACAGC GACTGCACCA

ACCGAGCTGT AACTCACAGG CTCCTAGAGA AGCTTGGTTG CCGAGTCCTT

TCGGTCGCTT CTGGCGTCCA ATGCATCAGC TCCTTCGCTG CGGAGTCGTC

CTTCCAGCTG GTGGTTCTTG ATCTTGACAT GCAGACGATG GATGGATTCG

AAGTAGCCCG CGCGATCAGG AAGTTCAGTA GCAATAGTTG GCTGCCGTTG

ATTATTGCCC TAGCAGCAAG AATCGACGAC AACATCCGGG ATCGTTGCCA

GAGGTCAGGA GTAAATGGCC TGATCCAGAA ACCGGTCACA TTAGCCGCGC

TGGGAGATGA ACTGTATAGA GTCCTTCAGA ACAATTAAAA GAGCCTGACG

GTTCTCATTT CTTTCAATCT CAATAGATTG CTATAGCTTG ATCGGTAACT

AATTTCTGCC AGGTTAGCTC CATACAATCA CAAAAAAAA AACATTTTGA

GGCAAAAGGG AAATGTATAG GAAGCTGAAA GCATCGCTTT CTGCTTGGTT

CCTCGGTGAA GGAGGAGGAG GACGACTACG ACAGGAAGGT ACAAAAAACT

TGGAGAGATC ATACTGTTAG AACTTAGACC CATTCATCTG TAAACCCTCA

GATAAGCAAA GAATTAGATT CATGCACTAA CACTAACCAC GATATAATTA

GTTTGGACGA AATCCATGAG CTGTTGAGTT TGTGATTGGG ACTCAGAATG

GATGGGGGTT CAGTGAATGC AGCGGCATAT GTGTCTACAG GGGGGAAAAA

GGAACTTTTG TTATTGGTTA GACATGCTGC AAAAGCAGGC TGGATGAGAT

TGCAGACAAG AAGGCAGACG ATGCGGCTGA TGCTGACCTT TTTTACATTA

CAGACTTGGG CTGGTTCTGG TCAGCGAACC CTTGCTTGCT TATACGATAT

CCTCTGTTCC TTACACGATA TCCTTCTAGA AACACTTTAA GATATAAACT

AGTTTTTTTT AAGCACGTTA GCATCAGTGG AACAGTTTGG GTAGTAAAAA

TCTGGTGCAT TGGCACCTAA GCTTCTTTGG TCACCTCAAG AGCTCTCAAC

AATCAGAGCG ATTGTCTAAT GAGAATCCAC GGCCAGATTT GGTGTTTTGA

CCCGGTT
```

*Zea mays* ethylene receptor (ethylene resistant, ETR2-like); ETR9 coding sequence (cds).

SEQ ID NO: 31

```
ATGGTGGTGG GAACGGCACT GCTGCGCGGG GTTTCCTCCG CGTGGATCCT

CCTGTTCCTC TCCTCCCTGC TCCTCTCGCC GTCAGCGGCG TCTGTCGATT

TCGGCCACTG CGGCGGCTGC GACGACGCCG ACGACGGCGC CCTCTCCAGC

ACCTATAACA TCCTGCAATG CCAGAAGGTC AGCGACTTCC TCATCGCCGC

GGCCTACTTC TCCATCCCGC TCGAGCTGCT CTACTTCGCC ACCTGCTCCG
```

-continued

```
ACCTCTTCCC CCTCAAATGG ATCGTGCTGC AGTTCGGCGC CTTCATCGTG

CTCTGCGGCC TCACGCACCT CATCACTGTG TTCACCTACG AGCCGCACTC

CTTCCACCTC GTACTCGCCC TTACCGTCGC CAAGTTCCTG ACGGCACTGG

TCTCCTTCGC GACGGCCATC ACCCTGCTGA CGCTGATACC ACAGCTCCTG

AGGGTGAAGG TCAGGGAAAA CTTCCTGATG AACAAGGCGC GTGAGCTGGA

CCGGGAGGTG GGGAGGATGA AAAGGAAAGA AGAGGCGAGC TGGCATGTGC

GCATGCTCAC ACAGGAGATC CGCAAGTCGC TCGACAGACA TACCATCTTG

TACACCACCA TGGTTGAGCT CTCGAAGGCA CTGGAACTGC AGAATTGTGC

TGTCTGGATg CCTGATGAGA CCAGGAGCAC GATGATCTTA ACACATCAGC

TGAGGGAAAG GGATATAATG GACCCACAGA AACACTCGAT TCCTATTGAT

GATCCGGATG TTCAAGAAAT AAAGGCAACC AAGGATGCAA AAGTTCTTGG

CCCAGATTCG GCGCTAGGGG TTTCTAGCCG AAGCAAGCAT GAAGCAGGGC

CTGTGGCTGC AATAAGGATG CCGATGTTAA GGGTGTCAAA TTTCAAGGA

GGGACTCCGG AAGTGATGCA GACGAGCTAT GCTATCTTGG TTCTGGTTTT

GCCTAATGAT GGTTCATTAG GGTGGGGTCG AAGAGAGTTG GAGATTGTTG

AGGTAGTTGC TGACCAAGTT GCAGTCGCTC TGTCACATGC TGCACTCCTA

GAGGAGTCTC AGCTGATGCG AGAGAAGCTT GCCGAGCAGC ATAGGGACTT

GCTGCAGGCA AAGGATGAAG CCATGAGGGC AGGGGACGCT AGGAATTCCT

TCCAGACTGC AATGTACGAT GGAATGCGAA GGCCAATGCA CTCAATCCTT

GGTCTCGTCT CAATGATGCA ACAGGAGAGC ATGAATCCAG AGCAAAGGCT

TGTGATGGAT GCCATTGCCA AGACAAGCAG TGTTGCATCC ACACTGATGA

ACGATGTGAT GCAAACATCG ACAATGAACT GTGAGCACTT GTCTTTGGTC

AGGAGGCCGT TCAACCTTCA TTCCTTCATT AAAGAAGTTG TTGGAGTGGT

CAGATGTCTA ACTGGTTGCA AGGGTGTGGA GTTTGAGTTT CAAGTGGAGA

ATTCTTTGCC AGAAAGGATC ATTGGTGATG AGAAGAGAGT CTTCCATATT

GTCCTGCACA TGGTAGGCAC TCTAACAGAC CGATGTAATG CTGGCTGTAT

CTCATTATAT GTAAATGTCC ATAATGAGGT TGAAGATAGG CATAATCATG

ACTGGATGCT GCGAAGAGCA AACTTCTCTG GGGGCTATGT ATGTGTGAAA

TTTGAGATTA GGATTAGAAA ATCAAAGGGC TATCTGTTGA GTTCATCAAG

CAGTCAGATA AGTCAGGGAT CCAAACCCAA CAATTCTGAG ATGGGGCTTA

GCTTCAATAT GTGCAAGAAG ATTGTGCAGA TGATGAATGG CAATATTTGG

TCAGTATCAG ATTCTAAAAG CATCGGAGAA ACTATCATGC TAGTCCTCCA

GTTCCAGTTG GAACCTGTGA CTCCGGTCTC TGGAGCGTCC TCAGATTTGT

ACAGATCATC CGCAATTCCC AACTTTAATG GGCTCAGAGT CCTCCTTGCG

GACAGCGACT GCACCAACCG AGCTGTAACT CACAGGCTCC TAGAGAAGCT

TGGTTGCCGA GTCCTTTCGG TCGCTTCTGG CGTCCAATGC ATCAGCTCCT

TCGCTGCGGA GTCGTCCTTC CAGCTGGTGG TTCTTGATCT TGACATGCAG

ACGATGGATG GATTCGAAGT AGCCCGCGCG ATCAGGAAGT TCAGTAGCAA

TAGTTGGCTG CCGTTGATTA TTGCCCTAGC AGCAAGAATC GACGACAACA
```

-continued

```
TCCGGGATCG TTGCCAGAGG TCAGGAGTAA ATGGCCTGAT CCAGAAACCG

GTCACATTAG CCGCGCTGGG AGATGAACTG TATAGAGTCC TTCAGAACAA

T
```

Zea mays ethylene receptor (ethylene resistant, ETR2-like);
ETR9 amino acid sequence.
SEQ ID NO: 32

```
MVVGTALLRG VSSAWILLFL SSLLLSPSAA SVDFGHCGGC DDADDGALSS

TYNILQCQKV SDFLIAAAYF SIPLELLYFA TCSDLFPLKW IVLQFGAFIV

LCGLTHLITV FTYEPHSFHL VLALTVAKFL TALVSFATAI TLLTLIPQLL

RVKVRENFLM NKARELDREV GRMKRKEEAS WHVRMLTQEI RKSLDRHTIL

YTTMVELSKA LELQNCAVWM PDETRSTMIL THQLRERDIM DPQKHSIPID

DPDVQEIKAT KDAKVLGPDS ALGVSSRSKH EAGPVAAIRM PMLRVSNFKG

GTPEVMQTSY AILVLVLPND GSLGWGRREL EIVEVVADQV AVALSHAALL

EESQLMREKL AEQHRDLLQA KDEAMRAGDA RNSFQTAMYD GMRRPMHSIL

GLVSMMQQES MNPEQRLVMD AIAKTSSVAS TLMNDVMQTS TMNCEHLSLV

RRPFNLHSFI KEVVGVVRCL TGCKGVEFEF QVENSLPERI IGDEKRVFHI

VLHMVGTLTD RCNAGCISLY VNVHNEVEDR HNHDWMLRRA NFSGGYVCVK

FEIRIRKSKG YLLSSSSSQI SQGSKPNNSE MGLSFNMCKK IVQMMNGNIW

SVSDSKSIGE TIMLVLQFQL EPVTPVSGAS SDLYRSSAIP NFNGLRVLLA

DSDCTNRAVT HRLLEKLGCR VLSVASGVQC ISSFAAESSF QLVVLDLDMQ

TMDGFEVARA IRKFSSNSWL PLIIALAARI DDNIRDRCQR SGVNGLIQKP

VTLAALGDEL YRVLQNN
```

Zea mays ethylene receptor (ethylene resistant,
ETR2-like); ETR9 forward primer sequence.
SEQ ID NO: 33

```
GCTATGTATGTGTGAAATTTGAGATTAGGA
```

Zea mays ethylene receptor (ethylene resistant,
ETR2-like); ETR9 reverse primer sequence.
SEQ ID NO: 34

```
AGCTAACCTGGCAGAAATTAGTTACCGA
```

Zea mays ethylene receptor (ethylene resistant,
ETR2-like); ETR40 genomic sequence.
SEQ ID NO: 35

```
AAACTGCGCA ACTCGTGAAA GGTAGGCGGA TCTGGGTCGA CCTGCAGGTC

AACGGATCAG ACTCCAAGGC CTACAACAAG CATATCAGAC CCCGATTCTA

GCAATAAAAG ACAAGGTTCG TCTTCACCCC TACTTTCCTA TGCCAATTAT

CCGGTTGGTG AGGTGACACA GTAACCAATG AGGTGGGTGT ACGAATGGGA

GGACATTAAG TACTACCAAA TGTTGGTGGA GTCATGGATT ACGACTTCTT

CGTGGACCGA TCAGACTTGG ACAGGGTACA ATGCACAATT GATACATGAG

CAAGGTATTA TGTTGCTATC AACGGAGGAG TATAATATGG CACAAGCACA

ATATCAGTGG AATGCACCAT GTGTGAATGA TCTTTGACGG AGCAACAACT

GTGAACTATG AATGGTGTAT TTTTATCTTC GTCATTGTTT GTGAACTATG

AAACTGCTAA ATATTATTAT TAAAATTGTG ATATTGTTTA GGGTCATCTT

TTGTTTAAAT TATGGAGCCT TAATATGCTT TATTTACAAA ATACATATAG

CTCGGTCTTT ATTTCTATGC TGTCGATTTA TCAGGCCAAA AACCGATTAA

TCAGTCTTAT CGATTTATGG GTTTTGAATT AAAATTTTTT GACCAATTCC
```

```
-continued
TACCTATTTT CACCGGTATC GATGGGCACA TGTTTTCACA ATTTCACCCC

TCAGATCTTG TTCGGTTATT TTCAATCTAT ATAGATTGGA AGTAATTGAT

TCAAATTGAA AGAAATTTTA ACTTACTAAG ATTAAAATTC ACTAAATCTT

TCTCAATCCA TATAAATTAG GATAGAACCG AACAAACCCT CAACCGGTTT

AGTGAACCCC GCCGGAGAGA CAACCCAACC CCCCTGCTCG ACCCGCTGAA

CTGCCGAAGC ATCGCCTACT CTTCCTACTC AGCTCCGCTG GTCCGGTCGT

CGCGTAGCGC CCTCACCCCC AGCCACCCCC ACCACGAAGG CCGCGCGCTC

CCCGCCTTCC GACGTCGCTC TCTCCGCCCA GCTCAAGCGC CCAGCGGTGA

GGGAAGGGAA GGAAAAACAG ACCTTTTTTT TTCTTCTCGG CGGCCTCGTG

ACTATGGATC CGCCGAGCTC CGGTCTCCCG CCGGTGCCGA GGTTTCCTGG

CTCGATCCGT GACCGGCCCA CGTGGAGACG GTGCTGGTGC TAGTACCGGT

GCCTCCACCG TGTTTCTTGG CGACCTTACT ACCTCCTCTC CTCCTCTGGA

AGATTGCTGC TGCAGCCTGC AGGAAAGATG GCCGAACGCC GAAGGTGGGC

AGCGTTAGTT ACTCCTCCAT GCTTTTTTCC TTCAGTTCAA CAAATATGTT

TGGATTTTTT TTTACCGGAC TGTGGAATGC TTCGAGCTCG GGGGTTTATC

GGATTTGGGC TGTTCTAAAT CTCCTACCTA CTCTGGCCCA TATTTTTACC

TTCTGGAGTA CGTGTATAAC AAGATCCATG GTGGACTGAT GGATTCGGTT

TTGACCGATA CATGTATTTC GATGCTATTT TTTGGAAGGA TTAAATCTTC

AACACGTGCC CAAGCCCAAC CGCCCAAAGG CATCGATTTG CTTTTCGCCA

GATCTTGATT TGTGTGCCGC GGTTTGATTG ATTGCAAAGC TGTGATGTTA

ACTGCGTTCA ATTTGTACTT ATACTACATC TGATGAATGC AGGAGCGTCG

GCGCGTGCAG TGTGGAATCG ACGCCGAGCG CCTCCAGTCG GTGCAGGAAT

GCGCAAATGC ACGTCTGAAT GAAGCCTGGT TGGTGGTAGA GCCGATGGTG

GTGGGAACGG CGCCGTGCGG GGTCTCCGTC TCCTCCGTGT GGATCCTCCT

GCTCCTTTCC TCCCTGCTCC TCTCGCCGTC GGCGGCGTCC GTCGATTTCG

GCCACTGCGG CTGCGACGAC GCCGACGACG GCGCCCTCTC GAGCACCTAC

AACATCCTGC AATGCCAGAA GGTCAGCGAC TTCCTCATCG CCGCGGCCTA

CTTCTCCATC CCGCTCGAGC TGCTCTACTT CGCCACCTGC TCCGACCTTT

TCCCCCTCAA ATGGATCGTG CTGCAGTTCG GCGCCTTCAT CGTGCTCTGC

GGCCTCACGC ACCTCATCAC CGTGTTCACC TACGACCCGC ACTCCTTCCA

CCTCGTGCTC GCCCTCACCG TCGCCAAGTT CATGACGGCA CTAGTCTCCT

TCGCCACAGC CATCACGCTG CTGACACTGA TACCGCAGCT CCTGAGGGTG

AAGGTCAGGG AAAACTTCCT GGTGAACAAG GCACGTGAGC TGGACCGGGA

GGTGGGGATG ATGAAAATGA AGAAGAGGC GAGCTGGCAT GTGCGTATGC

TCACACAGGA GATCCGCAAG TCGCTCGACA GGCACACCAT CTTGTACACC

ACCATGGTTG AGCTCTCGAA AGCGCTGGAA CTGCAGAATT GTGCTGTCTG

GATGCCCGAT GAAACCAGGA GCGAGATGAT CTTAACTCAT CAGCCAAGGG

AAAGGGATAT AATGGACCAG CAGAACTGCT CGATTCCTAT TGATGATCCA

GATGTTCAAG AAATAAAGGC TACCAAGGAC GCAAAAGTTC TTGGGCCAGA

TTCGGCACTA GGGGTTGCTA CCCGCAAGCT TGACGTGGGG CCTGTGGCTG

CAATAAGGAT GCCGATGTTA AGGGTGTCAA ATTTCAAAGG AGGGACTCCA
```

```
GAAGTGATGC AGACGAGCTA TGCTATCTTG GTTCTGGTTT TGCCTAATGA
TGGTTCATTG GGGTGGGGTA GAAGAGAGTT GGAGATTGTT GAAGTAGTTG
CTGACCAAGT TGCGGTCGCT TTGTCACATG CTGCACTCCT AGAGGAGTCT
CAGCTGATGC GAGAGAAACT TGCTGAGCAG TATAGGGACT TGCTGCAGGC
AAAGCATGAA GCCATGAGGG CAGGGGAAGC TCGGAATTCC TTCCAGACTG
CAATGTACGA CGGAATGCGA AGGCCAATGC ACTCAATCCT TGGTCTTGTC
TCAATGATGC AACAGGAGAG CATGAATCCA GAGCAAAGGG TTGTGATGGA
TGCCATTGCC AAGACAAGCA GTGTTGCGTC CACACTGATG AATGATGTGA
TGCAAACATC GACAATGAAC TGTGAGCACT TGTCTTTGGT GAGGAGGCCG
TTCAATCTTC ATTCTTTTAT TAAAGAAGCT GTTGGAGTGG TCAGATGTCT
AACTGGTTGC AAGGGTGTAG AGTTTGAGTT TCAAGTGGAT AATTCTTTGC
CAGAAAGGAT CATTGGTGAT GAGAAGAGAG TCTTCCACAT TGTCCTGCAC
ATGGTAGGCA CCCTAATAAA CCGATGTAAT GTCGGCTGTA TCTCGTTATA
TGTCAATGGT CATAATGAGG TTGAAGAGAG GCATAATCAT GACTGGATGC
TGCGGAGAAC AAACTTCTCT GGGGGCTATG TTTGTGTGAA ATTTGAGATT
AGGATTAGAA AATCCAAGGA CTATCTTTTG AGTTCAAACG GTCAGATAAG
TCATGGGTCC AAACCAAACA ATTCTGAGAT GGGGCTTAGC TTCAATATGT
GCAAGAAGAT TGTGCAGGTA AATCGAAATA ATAAAACATC TCAAGCATTT
ACATCCAATA GGAAGAAAAC TATATTGTCA TCTCGTTTAT GTCACTCGCT
CCTGGTGCTT CTCAGGCTCT GTATATATAT TGCTGATAAT GCTTGGTTAG
GTTTGACTTC TATGCAAGGT TAATATTGTT AAAGCGACAA CAATTTATTA
GATTGTGGTG GTTCTGTTAC CCTACTTGAC TCAGTTTATC TTCGATTACT
TGGACCTTCC AGACTTTGAC AGATGCTAGA AAAATATTAG CGGTTCTTTG
ATCTCGAGTG ACACAAATTT TTTTAGAACC TGTTGACTGT TCTCCATCTC
TCGTATTTTT TGTACAGCTG GGGACTAGCA TCTTAGGCCT TAGGCTTGGT
CGTCACATAG CTAGTTGGCC ACACACCAAT TTGAACAAGA CAGAATATGT
TTGGCGGCCA TAGTGTGGCC TTTTATGCAA GCCCTTGGAA TATTTATTAT
CTCATAAAAA ACTGGGTAAA CCGTGAGAAC ATATTGGCCC TTTTGTTGAA
CTGATGCTTT AGTAATTAGT CATAATTATT TTATGGTATT TTTTTCTGGA
AGCTTGCATG GTTTCGCGTA AATATATTTC GTCTAGTTAT GCTAGTAGTA
GCCCAAACCT CAGCGACTCT ATTTGATTGT TATGATTCGG TCAGCAATTT
GTTCATTAGC TGTGGGAATG GTCAATGCGC ACTTGATTTG ATGTACAGTC
ATTAGTACGC TGATGTGAGC CCTTATTTCT GCTGCAGATG ATGAACGGCA
ACATTTGGTC AGTATCAGAT TCTAAAAGCG TTGGAGAAAC CATCATGCTG
GTCCTCCAGT TCCAGCTGCA GCCTCTGACT GCGGTCTCCT CCGCGGCGTC
TTCAGACTTG AGCCGATCGT CCGCAATCCC CAACTTCAAC GGGCTCAGAG
TCCTCCTGGC GGACAGCGAC GACACCAACA GAGCAGTAAC ACACAGGCTC
CTGGAGAAGC TCGGCTGCCG GGTCCTTTCG GTCGCCTCCG GTGTCCAATG
CACGAGCTCC TTCGCCGCCG AGCCGTCCTT CCAGCTGGTG GTCCTGGACC
TCGCCTTGCA GAGGACGGAC GGGCTCGAAG TGGCCCGCGC GATCAGGAAG
```

-continued

```
TTCAGTAGCA ATAGCTGGCT GCCGCTGATC GTCGCCCTAG CTGCGAGGAT

CGATGACAAG GTCCGAGACG GATGCCAGAG GTCGGGGATA AGCGGCCTGA

TCCAGAAACC GGCCACGTTA GCTGCGCTGG GAGATGAGCT GTATAGGGTC

CTTCAGAACA GTTGAAAGTG CCGCCTGATG GTTCTCATTG CTTTCAGAAT

TCTCAATAGA CCGCTGTAGC TTGGTTAGAT CCATACATTC ACAAAACATT

TGGGGGCAGG CGAAGGGAAA TGTATAGGAA AAGCTGGAAG ACCGCTGCTT

CTCGCTTGGT TCCTCAGTAG TGAAGGACGA CGGTGACAGG AAGGTACAGA

ATTTTGGAGA GATCATACTG GTAGAGCTTA GACTCATTCA TTTGTAAAAC

CCTCGGATAA TCCAAGGTTT AGATTCTTGC ACTAGCACTA ACCACGGTAT

AAATAGTTTG GACGAAATCC ATGGATGGGT TCAGTGAATG CTGGCATAGT

AGATGCCTAA AGGGGCAAG GAACTTTTGT TATCGGTTAG ACATGCTGAA

AAGCAGGCCG GATGAGATTG CGGACAGGAA GGCAGCTGAT ACGGCCGATG

CTGACCTTGT ATCTTGTTGA AGATTAAATA CTATGGTAGT AGTACTTGCA

GTCTTGATCT GGTGGGTAGT GCTGGTGCTC CTGCTGCATT TCTTACTTGC

TTGGCCTGCT TCTGGCCAGC AAACTCCTGC TTGCCATCTT CTTAGCACTG

ATTCCTATGG TTTTTTTAAT AGGGTATCCT TTCAACTGTT GAGACACATT

ACCACACATA TATAAAAAAC ATTTTTAATC CCTTGCTACC GAAGCTTCAG

ATGTCATCTC AAGAGCTATT CTA
```

*Zea mays* ethylene receptor (ethylene resistant, ETR2-like); ETR40 coding sequence (cds).

SEQ ID NO: 36

```
ATGGTGGTGG GAACGGCGCC GTGCGGGGTC TCCGTCTCCT CCGTGTGGAT

CCTCCTGCTC CTTTCCTCCC TGCTCCTCTC GCCGTCGGCG GCGTCCGTCG

ATTTCGGCCA CTGCGGCTGC GACGACGCCG ACGACGGCGC CCTCTCGAGC

ACCTACAACA TCCTGCAATG CCAGAAGGTC AGCGACTTCC TCATCGCCGC

GGCCTACTTC TCCATCCCGC TCGAGCTGCT CTACTTCGCC ACCTGCTCCG

ACCTTTTCCC CCTCAAATGG ATCGTGCTGC AGTTCGGCGC CTTCATCGTG

CTCTGCGGCC TCACGCACCT CATCACCGTG TTCACCTACG ACCCGCACTC

CTTCCACCTC GTGCTCGCCC TCACCGTCGC CAAGTTCATG ACGGCACTAG

TCTCCTTCGC CACAGCCATC ACGCTGCTGA CACTGATACC GCAGCTCCTG

AGGGTGAAGG TCAGGGAAAA CTTCCTGGTG AACAAGGCAC GTGAGCTGGA

CCGGGAGGTG GGGATGATGA AAATGAAAGA AGAGGCGAGC TGGCATGTGC

GTATGCTCAC ACAGGAGATC CGCAAGTCGC TCGACAGGCA CACCATCTTG

TACACCACCA TGGTTGAGCT CTCGAAAGCG CTGGAACTGC AGAATTGTGC

TGTCTGGATG CCCGATGAAA CCAGGAGCGA GATGATCTTA ACTCATCAGC

CAAGGGAAAG GGATATAATG GACCAGCAGA ACTGCTCGAT TCCTATTGAT

GATCCAGATG TTCAAGAAAT AAAGGCTACC AAGGACGCAA AAGTTCTTGG

GCCAGATTCG GCACTAGGGG TTGCTACCCG CAAGCTTGAC GTGGGGCCTG

TGGCTGCAAT AAGGATGCCG ATGTTAAGGG TGTCAAATTT CAAAGGAGGG

ACTCCAGAAG TGATGCAGAC GAGCTATGCT ATCTTGGTTC TGGTTTTGCC

TAATGATGGT TCATTGGGGT GGGGTAGAAG AGAGTTGGAG ATTGTTGAAG

TAGTTGCTGA CCAAGTTGCG GTCGCTTTGT CACATGCTGC ACTCCTAGAG
```

```
GAGTCTCAGC TGATGCGAGA GAAACTTGCT GAGCAGTATA GGGACTTGCT

GCAGGCAAAG CATGAAGCCA TGAGGGCAGG GGAAGCTCGG AATTCCTTCC

AGACTGCAAT GTACGACGGA ATGCGAAGGC CAATGCACTC AATCCTTGGT

CTTGTCTCAA TGATGCAACA GGAGAGCATG AATCCAGAGC AAAGGGTTGT

GATGGATGCC ATTGCCAAGA CAAGCAGTGT TGCGTCCACA CTGATGAATG

ATGTGATGCA AACATCGACA ATGAACTGTG AGCACTTGTC TTTGGTGAGG

AGGCCGTTCA ATCTTCATTC TTTTATTAAA GAAGCTGTTG GAGTGGTCAG

ATGTCTAACT GGTTGCAAGG GTGTAGAGTT TGAGTTTCAA GTGGATAATT

CTTTGCCAGA AAGGATCATT GGTGATGAGA AGAGAGTCTT CCACATTGTC

CTGCACATGG TAGGCACCCT AATAAACCGA TGTAATGTCG GCTGTATCTC

GTTATATGTC AATGGTCATA ATGAGGTTGA AGAGAGGCAT AATCATGACT

GGATGCTGCG GAGAACAAAC TTCTCTGGGG GCTATGTTTG TGTGAAATTT

GAGATTAGGA TTAGAAAATC CAAGGACTAT CTTTTGAGTT CAAACGGTCA

GATAAGTCAT GGGTCCAAAC CAAACAATTC TGAGATGGGG CTTAGCTTCA

ATATGTGCAA GAAGATTGTG CAGATGATGA ACGGCAACAT TTGGTCAGTA

TCAGATTCTA AAAGCGTTGG AGAAACCATC ATGCTGGTCC TCCAGTTCCA

GCTGCAGCCT CTGACTGCGG TCTCCTCCGC GGCGTCTTCA GACTTGAGCC

GATCGTCCGC AATCCCCAAC TTCAACGGGC TCAGAGTCCT CCTGGCGGAC

AGCGACGACA CCAACAGAGC AGTAACACAC AGGCTCCTGG AGAAGCTCGG

CTGCCGGGTC CTTTCGGTCG CCTCCGGTGT CCAATGCACG AGCTCCTTCG

CCGCCGAGCC GTCCTTCCAG CTGGTGGTCC TGGACCTCGC CTTGCAGAGG

ACGGACGGGC TCGAAGTGGC CCGCGCGATC AGGAAGTTCA GTAGCAATAG

CTGGCTGCCG CTGATCGTCG CCCTAGCTGC GAGGATCGAT GACAAGGTCC

GAGACGGATG CCAGAGGTCG GGGATAAGCG GCCTGATCCA GAAACCGGCC

ACGTTAGCTG CGCTGGGAGA TGAGCTGTAT AGGGTCCTTC AGAACAGT
```

*Zea mays* ethylene receptor (ethylene resistant, ETR2-like); ETR40 amino acid sequence.

SEQ ID NO: 37

```
MVVGTAPCGV SVSSVWILLL LSSLLLSPSA ASVDFGHCGC DDADDGALSS

TYNILQCQKV SDFLIAAAYF SIPLELLYFA TCSDLFPLKW IVLQFGAFIV

LCGLTHLITV FTYDPHSFHL VLALTVAKFM TALVSFATAI TLLTLIPQLL

RVKVRENFLV NKARELDREV GMMKMKEEAS WHVRMLTQEI RKSLDRHTIL

YTTMVELSKA LELQNCAVWM PDETRSEMIL THQPRERDIM DQQNCSIPID

DPDVQEIKAT KDAKVLGPDS ALGVATRKLD VGPVAAIRMP MLRVSNFKGG

TPEVMQTSYA ILVLVLPNDG SLGWGRRELE IVEVVADQVA VALSHAALLE

ESQLMREKLA EQYRDLLQAK HEAMRAGEAR NSFQTAMYDG MRRPMHSILG

LVSMMQQESM NPEQRVVMDA IAKTSSVAST LMNDVMQTST MNCEHLSLVR

RPFNLHSFIK EAVGVVRCLT GCKGVEFEFQ VDNSLPERII GDEKRVFHIV

LHMVGTLINR CNVGCISLYV NGHNEVEERH NHDWMLRRTN FSGGYVCVKF

EIRIRKSKDY LLSSNGQISH GSKPNNSEMG LSFNMCKKIV QMMNGNIWSV

SDSKSVGETI MLVLQFQLQP LTAVSSAASS DLSRSSAIPN FNGLRVLLAD

SDDTNRAVTH RLLEKLGCRV LSVASGVQCT SSFAAEPSFQ LVVLDLALQR
```

-continued

TDGLEVARAI RKFSSNSWLP LIVALAARID DKVRDGCQRS GISGLIQKPA

TLAALGDELY RVLQNS

*Zea mays* ethylene receptor (ethylene resistant,
ETR2-like); ETR40 forward primer sequence.
SEQ ID NO: 38
GCTATGTATGTGTGAAATTTGAGATTAGGA

*Zea mays* ethylene receptor (ethylene resistant,
ETR2-like); ETR40 reverse primer sequence.
SEQ ID NO: 39
AAGCTACAGCGGTCTATTGAGAATTCT

*Zea mays* ethylene receptor (ethylene insensitive,
EIN2-like) gene; E2-25 genomic sequence
SEQ ID NO: 40

```
AAACCCACTC TTGCCACCCC GTGACAGCAG GAAACAGTAC ACAGTAGCGC

ATAACCTTCC AAGAAAATTT AATTAATAAA CCCGAAGAAG CCAAGAGGGA

AGGGAAAAAA AAGAAAGAA AAAAANCTGA CACATAAGAA AAGAGCAGCG

AGCAAGCTGA AGGTGAAAGC CACAGCAGCT CGTCCCCTTC CCCCCACTTC

TTCCTCAGAT AAGGAGAGGC CCCAGGCCAG AGAAAAAAGC ATCGAATTTC

CCCCCGTTAA TTGGCCTGAG CCCTCAGCCG TCTACCAGCA GCAGCTAGAG

GTACGATTCT CGCATTGCTT GCTCCCTGCG CCTGCCCTCG ATTTTTGCTG

TTTTTTCGAG CTCCTCTTCC AGTTCTTTTG CCGTGTTGGA ACCGCATCTA

TGCAGCCTAG CGCGGGGTAC TAGCGTGATT CGGTCAGTGG ATCCCGTCGG

GCTGCTGCTT CCTCGCGGCT GATTTGCGAG AGGAAGCAGG TCCCCGGGAA

GCGATCTCAT TTTTCGTTAT TTTTTTAGCT CCCTACACCA AAGACCAGAG

TCAGATCCGA GGCTACCCGC CGCCCCGGCA AGGATTTTAC CCGGCCGGAG

CTCTGCAACA TCGGTGGGAT CGATGGCTGC GACCTCCACG AGCTCCGGTG

CCCACGAATC GAAGTCAGCA GCGCCGTGTG GACTGAGTCA CGTGCCTGGT

TCGCCGTCCT GTCCGACGCT TCTCACCTCG AGAGCCCGTC GCTGTTGCCT

CGGACTCGAG GGAGCTGGCG GCGCAAACGC CGTGCGGCCA AAATCGAGAT

CCCCACCATC CGAATCGAGG TCCTCTCTAC CAGAATCAGT TCCCGCCGCC

GCGTCGAGGT AGCTGTCACC CAAATTGAGC TTTCCGTCGC TGCTGGATGT

GTTGGAATCG GAAGCTTCGG GCGCATAGCT TGAGCTCGCT CAAGTGTATC

GAGCAAGCAA ACCAAGCGTT GGGGGTCTTG CTTTGCGCCT TTGCCGCGCT

AGCTTAGCCT ATCTATCCGT GCTAGGAATC CCCCTCCCTT TCGGTGTGAT

GTTTTTGACT TGCCACTGCC TGGTGTTGCT GGGGCTGCTT TTCTCTTCTC

CTTTGGGGCT CTGAATGAAG ACTGAAGAAA TCGAAAGAGA GGAAAGCTAC

GCCTGAGTCG GGGAACGCCT ACGAAGTAAG TTTTGGCTTA AAGGTGGAAG

CTTTTGAGGT TTCTCCTTGC GAAATAAATG CTTTTTTCGA TGTTATTTGA

TGGATTTGGT TGGTACTCGG TCAAAAGGTG TTCTTGGTTT GCCCTTTCTA

TGCTCTGGCT GCTGTTGCAA CTGCAACTTC CCTTTCCCTT AGAGTTTGGC

GCTCTAAAAG TTGGTTCACT TTGCACGAAG GATTTCTGTT TCTTGTTGCT

GATTGGGTTG TTTGGATCTA TCTGCAGGCA GACAAGCTAG GTTTTACTGC

TTCATTGAGC ACAAAGATCC GCTGACCTCT TGCTCTTGGT AAAAATCCAA

CCTTTCTTGT ATTGTTTTCT TCCTGGGAAA ACCTCCTTGT GGTGCATAAA

CTTCGTAGTA CACTCTGCCA TTTCTGGAGA GGAAGCTGAG AACTACTATC
```

-continued

```
CATATCTGGC ACGACCCTTG TCAAGAACCA TGGCTGTTCA CATGCCATGA

AGCTGCTTGA ACTGGAGGCA CCTAAATGCT GTGGATTGTT CCTATGCAGA

TGATTGGATC AGTGGTTTCA GGCTTCGGGG GGTTCGATCA GATGTTGTAT

GAATAATAGC AGGATTGCTT GAGAGACTAT AGTTTGGGTA CTGTTTGCTT

CTGTATTTAC TGGTACGGTT TCCTACTGAT CTGCGGCTGC GCAGGAAGGC

ATTCTCTTTT TTGCCGTACC ATGGATGCAC CGGATGTTCA ACAGAGCATG

GGATATAAGG AGTCCAGGGG TGGTATGCCT AAGTTTTTCC ATGCCCTTGG

ACCAGCACTC CTGATTTCAA TGGGTTACAT TGATCTCGGG AAGTGGGTGG

CAGCCGTTGA AGCTGGTTCT TGTTTTGGAT TCGACCTGGT GTTGCTGGCT

CTCCTTTTCA ATTTCACTGC CATTGTATGT CAGTACCTTG CTGCTTGCAT

TGGCACTGTC ACAGGGAAGA ATCTTGCAGA GGTATCGGTT TACCGATGTT

GTTCCTTGGT TTTGCTGGCC TTCTATTGAG ATTTAGTTCA GTAAATCTTT

GTTTCCATTT CACAACGCTA TATGATGGCT TCATATTGAG CTGGACTTGA

AGGAACTTAG AAGAGCAGGG AGTAGGGAAA CTACATGCGA GATATTCAAT

TTATGCGAAT TGTTGATAAA CAAAATGGAT CAATTCACTT GCCTTGTTAA

ATAATTCTTT TCCATCTGTA GTTCAATTAT ACTCCCTCTG TTCCACAATA

GAAGTCGTTT TAGACTTTCA ACAAATTCAT TCAATAATTG ATGTATATGT

TATGTAATGT GTCTAGATTC GTTGCCATTC ATTTGAATAT AGACATAAAA

AGAAGACCTA AAACGACTAC TAATTTGGTA CAGAGGGAGT AGTACTGTTG

GATGTAGAAG GGCTTCTTTT TGGAGGAAAA TATATCTTTT ATCTCATCTT

ACTTGTTCTT GATATTCCTT TCAAGTTGCT AACTTTTTCA TGCCTTCACA

TGAAACAAAG ATATGCCACC AAGAGTACAA CCAGCCAACA TGTATATTCC

TTGGTGTTCA AGCTGGATTG TCTTTGTTGA CGTCAGAGCT GAGTATGGTA

CTTGCAGATT TAGTTGGATG TCTCTCATAC CTTTTATGTT TAAATTGTGA

ATTCTCATCC TGCAAAGCAA TGTTACATGA TGTAGTTCTG ACATGCTAGA

TTCTGTTGGC TATATCTGGA ATTTTCAGAT TTTTGGCATA GCACTCGGAT

TCAACCTCCT GTTTGAATAT GATGATCTCA TCACAGGGAT ATGCTTTGCA

ACAGTGGTAC CTAATCTGCT ACCATATGCT ATATCCCACC TGGTAAGGTT

ACTACTTCAA GAAAGATACT TGAACAGATG CTGATACACT AATGTGACTT

TATGTTTGCT AGTTACTTAC CCTTTATGTC TGCTCTAGGG AAAGAAGATG

GAAGGGACAA TAAATGCCTG CATAGCAGGA TTTGCACTTC TTAGTTATGT

GCTTGGCTTA TTGGTTAGCC AGCCACAAAT TCCTCTCACG ATGAATGTAA

TATTCCCCAA GATCAGTGGT GAGAGTGCTT ACTCTCTGAT GGCGCTTCTT

GGTGCAAACA TAATGGCACA CAACTTCTAC ATTCATTCAT CAGTTGTCCA

GGTAAATTGT TTGATTAGTG CCCTTGGACT TAAAATTTAG TGGGCAACGC

CTTGCCAGAA ATACTTCAAA CCATACATTT ACATTTATTT CAATTTTAGC

TTGTTGTATG GAGTTTGTAA AGTCCTAAGA GTGAGCGAGA TCATTATATT

TGAACTTCTG TTCATGCCAG TTGAATATTG GATACAATTT GAAAATTATA

TTTATTTCCT TTATTATTTT GATGATTTGT GGGTACACCA CATCGAAATA

AAACAAGATG TAATTAATCG CGTTTCAATT GTTTGGATAA CTTCATACAA

GTTTCCACCG CAGGATCCAC ACTTTGTTTA TCTGTACACA TTGTGCTCAG
```

```
CTTTTGGAAT TTTTTGTTTA GTTCATGAAA TTTTGTGTCT TATGTTTGGG
TTTGTAGCAT ATCACAAAAC ATCAAAATTG TACCATTTCT AACTTTTCAC
ATCATGTTCA TTGGAAAATA TTGACATGTG CAAAAAATGC AAGTAGTGAC
AGTTTGCGTA CTTTGCAGTC GTTTGTTTTC ACTGAATTGT CATCAGTTTC
TGCGTGTTTT TTAATCAAGA AACATTGTAT TTGCAGGGTC AGAAAAAGTC
ATCTGCAGTT GGTCTTGGAG CCTTATTTCA CGACCACCTT TTTTCAATAT
TGTTCATTTT TACTGGAATC TTTATGGTGA ACTATGTTCT AATGAACTCT
GCAGCAGCGG AATCTACTAA TACTCTTCTC ATTACCTTCC AAGATGTTGT
AGAGCTAATG AATCAGGTAA GCAGCTAAAT TTCCTAGTTG TTTATTCTCT
GTGCTAAGTT TCTGCTGAAT ATTTTATTTA GGAAGATATC CTACTCCGCT
ATAGAAAACT GAATTTTTGA GTACTTTGCA GATATTTGTA AACCCTCTGG
CACCAACTAT ATTTTTAGTG GTTCTTCTCT TCTCCAGCCA CATCATCTCG
CTGACATCTG CTATCGGTAG CCAAGTGATT TCACACCATT TATTCGGTAT
AAACCTTCCT CTTTCTGGAC ATCGTCTCCT ACTGAAGGTT TTTGCCATAG
TTCCTACTCT GTACTGGGCG AAAGTTGCAG GAGCTGAAGG GATATACCAA
TTATTAATTA TATGCCAGAT TATTCAAGCC ATGCTTCTTC CATCTTCAGT
CGTCCCACTT TTTCGTGTTG CTTCATCAAG ATCAATAATG GGAGCCCATA
GAGTGTCTTT GCATCTGGAG ATACTGGTTT TTCTTGCATT TCTCCTTATG
CTATTTTCAA ATATCATATT TGTGGCAGAA ATGCTATTTG GCGACAGTGG
GTGGATGAAC AATCTGAAAG GATATACTGG AAGCCCTGTG GTGCTCCCAT
ATACCGTTTT AGTTTTAGTT GCACTTATAT CTGTGGCTTT TCACTGTAC
CTGGCTGTTA CACCATTGAG ATCTGGAAGT CATGAAGCTG AATCCCATGA
ATGGTCTGTG CATTCTCAGA GAGAACTCTT GAATACTTCT CAAGAAGGG
AAGATGTTAA GGTGGACAAT GTTACATATG AGGAAGATCA AAGATCAGAT
GTTGTCCCTT CTCCCAGGGA TGTGCCTGAC AGCCATCCGG AACTGGCCTT
GGACTATATT GATACTTCTG ACACTGCTGT AGAATCTGAT CACGACTCTC
AACAATCTAC TGCTTATGCA TCCACTGCTC CTGAAACCTG CTCCTCCCCG
TCGTTTACTC GCGAGGAGTC AAAATCAGTT GTTGCAGTCA ACTGGCCGGA
GCCTTTGGAG AAGGTTCCTA CTTCTACTGT GATGGAGGAA AGCACAGTAG
AAAATGTGGT CTCTAGGATC ACGACTGAAA GAGATGTTTT AGTAGAAACA
GATGTTGTCT CGGGCAAGGA TAAGGAAGAT ATCCGTACTT GGAGTCTGA
GAAGTCAATT GTTGATAGCA CCCCATATGT GTCTGATGAC GGTCCGCCAT
CCCTTACTTT CAGCAGGGGA AAGGGCTCAG ATGCAGGAAA TGGCAGTGGT
AGTCTCTCAA GGTTATCTGG TTTGGGCCGT GCAGCAAGGA GACAGCTAGC
TGCTACTCTT GATGAGTTCT GGGGGCATCT GTTTGATTAC CATGGTAAGC
TCACTCAAGA AGCTAGCACC AAAAAGTTTG GTATCTTGCT TGGGATAGAC
CTTAGAACAC CTAGCACATC TGTAAGAACG GATAAACAAG CTGCTGAAAT
ACTTAAGAGC CCACTGGTGA GAGACTCAAT GCGGGGGCA GCTTTTTTGT
CAAGCTCAGT GGACATGATG TCCCCTAAGA ATGAAACGTC GAATTTGGAA
CTTGCATATG GGCTTCAGAG GGGACCTGGC ATGGGATTGT CAAGCTGGTC
```

```
-continued
TCAGGGTATG CAGCTACCAA ATACACAGCT GCAGAGCTCA AGCAATAGCC

TACTTGAGCA GAGTGCAAGA TTAAACTCAA ATTTTAGTTC ATCTTATTCA

GACAACAATC AGTTCTACCA ACCTGCAACA ATTCATGGAT ACCAGCTCAC

ATCTTACCTG AAACAGATGA ATGCCAGCCC AAGCCTTTAC TCTAGCATGC

CGCTGGACCC ACAACGGCTT CCAAAATCAT CTGTGTCTGC TGTGCCAAAC

TATGCTGATT CCATGATGCA TGCTCGTAAT CATAACCTGC TTGCTTCACT

GGGTGGTACT ACTACACAGC TTCCTGCAAC ATCCCGCGTA GGCTCAATGA

TGCCTGAAAG ATCGTATTAT GATCCTTCCA GCGTTGATGG GAATGAAAAC

GCTGGTTCAC CTGCTTACTC AAAAAAGTAC CACAGCTCAC CTGATATGTC

TGGAATAATC GCTGCAAGTA GAGCTGCACT CTTGAATGAA GCAAAGTTGG

GTGCTGCCAT TGGACCACAG TCATACCTCA GCAGGCTGGC GGCAGAAAGA

TCTCAATATG CAAGCTCAAC AGCCAGGCCC GCGGCTCCAT TAGCATTTGA

CGAGCTTTCA CCTCCTAAGC TCCAGAGTGA TATCTTCTCG GCGCAGTCAA

GCATGAGACC AAGTGCTAGA TCCCTTTGGG CTAAGCAACC ATTTGAGCAA

TTGTTCGGCA TGTCAAGTGC AGAGCTCAGT AAAGGTGACT TCAATCTTCC

AGGCAGATCA GGTGGCGTGG CCAAGGATGA TTTCTCTTAT AAGGAATCTG

AGACGAAGCT TCTTCAGTCC CTCAGGCTCT GCATCATGAA GCTCCTTAAG

CTAGAGGGAT CAGGGTGGCT GTTCAAGCAA AATGGTGGTT GTGATGAAGA

TCTAATCGAC CGAGTCGCTG CAGCCGAGAA GCTATTGATG CAAGGGACTG

CCGAGAATCA ACTGCTGCTT CATGGTGGTG ATCTCCAGCA ACATTCTTCC

GACCAGGCCG GCATCCAGTA CATGCGCACG CTTCCCAACT GCGGGGAGGA

CTGTGTTTGG CGCGCGTCAC TCGTCGTTAG TTTCGGTGTC TGGTGTGTCC

GCCGAGTGCT GGACATGTCT CTGGTGGAAA GCAGGCCAGA ACTTTGGGGC

AAGTATACCT ATGTCCTTAA CCGTCTTCAG GTGAGTTGTT ATGGTCCTGA

ACTAGTTTAA CTTTTTTTTT TGCAATCGAT AATATCCTGT TTTTAATACT

TGCTTACAAT TAGGGGTGGA CAATCATCTG AAATGGCATT ACAATATAGA

AAACAAAAGG ACTGGCCCAG GATTTTCCCG TATTTATGAA GATATCTAGT

AGCACAAAAA AATAGCTGTG AAATCAGTTA AAAATGACAT TTTTTTTAAT

GTTTGCGTGA ATTCAGAAAC GTTCTAAAAC GGTATCATAT TATAGAAAAC

GAGAATGAAG GATTTGTGCT GTTCACTTAA CAGTGATTCA TTTTATGTTT

GTGCAGGGGA TCTTGGACCC TGCGTTCTCC AAGCCTCGGG GTGCTCTGAC

AATATGCACC TGCCTTCAGA AAGACACCAG AGTGCGCAAT AGCCCACCCC

ACAGTGGGCT AACAGCCATG GGCCCGGTCC CCACACCGAT CCGGGGCGCC

TTCACGACCG CAGGCGTGGT TCTGGAGATG ATCAAGGACG TGGAGGCTGC

GGTCTCAGGC CGCAAGGGCA GGAGCGGCAC GGCGGCGGGC GACGTCGCCT

TCCCCAAGGG GAAGGAGAAC CTGGCCTCCG TGCTGAAGCG GTACAAGCGG

CGGCTCGCCA GCAAGGGCCA GTAGCGCGCG GGTGTCAGAC AGGCAGGCGA

TCGCAAGCAA TGTTAGGAGG AGCCTGACTA TTGTTCTCCA GGGGGGCTGC

CACTGGCGCC GGCCTCCCTG AGCCCTGGAT TTTTTCGTTG CACGACGTTC

CTAGGGACCG GTGGTTGCCC GATGGTCGTC TTGGTCCCTT CCAGCAGGTT

TTTTTTTTCC TTCCCTCTTT CTGTGGGTTT CTTTTTGTGG GCTTTGTGAT
```

```
GTTTTGAAAG GGGCAACTAG GGTATGTGCT CAGAAGGACT CAAGATGTAC

ACGCGAAGAT GTACTAGTCT GCTGATGCAG CGTTGTAAAG TCCACACTCT

GCAGGTTAAC CCTTTTTGGG GCCGTCAAGT GTTAGTGCGT GCCCTATGTA

TGTTAATCAC CCCTGCAGAG AGGTTGCGAA TACTGAACTA CTCACAGACC

TGCACCTGTC GAGATCGTTT GTAATATCCG ACGTCTTGTT CAGAATTGTT

CTCACTCTTT TTTGCCCGTT GTGTAATTTA CCCTGAAGGG ACTTCAAGTA

CGTGCTTCGG CAAGCACGGT CTTGAAAGAA AAAAACTGT TAGCATCAGT

GAGCTGCCTG TTGAGCAGTA AAAGAGAATA CAATGTGAGC TCTCAACTCA

AAAGCGAGAT GTGTCACGCG CGTATCTCAA GAAGCATTGG GCCAAAGCTT

TTTATGCCAG GCAAGAGAGA TGCTTCCAAA TGGCCGGTCC GAAATGCAGG

AAATGATGAG TAATATGGTT TGGCAAACCA CTTCCGT
```

*Zea mays* ethylene receptor (ethylene insensitive, EIN2-like) gene; E2-25 coding sequence (cds)

SEQ ID NO: 41

```
ATGGATGCAC CGGATGTTCA ACAGAGCATG GGATATAAGG AGTCCAGGGG

TGGTATGCCT AAGTTTTTCC ATGCCCTTGG ACCAGCACTC CTGATTTCAA

TGGGTTACAT TGATCTCGGG AAGTGGGTGG CAGCCGTTGA AGCTGGTTCT

TGTTTTGGAT TCGACCTGGT GTTGCTGGCT CTCCTTTTCA ATTTCACTGC

CATTGTATGT CAGTACCTTG CTGCTTGCAT TGGCACTGTC ACAGGGAAGA

ATCTTGCAGA GATATGCCAC CAAGAGTACA ACCAGCCAAC ATGTATATTC

CTTGGTGTTC AAGCTGGATT GTCTTTGTTG ACGTCAGAGC TGAGTATGAT

TTTTGGCATA GCACTCGGAT TCAACCTCCT GTTTGAATAT GATGATCTCA

TCACAGGGAT ATGCTTTGCA ACAGTGATGG AAGGGACAAT AAATGCCTGC

ATAGCAGGAT TTGCACTTCT TAGTTATGTG CTTGGCTTAT TGGTTAGCCA

GCCACAAATT CCTCTCACGA TGAATGTAAT ATTCCCCAAG ATCAGTGGTG

AGAGTGCTTA CTCTCTGATG GCGCTTCTTG GTGCAAACAT AATGGCACAC

AACTTCTACA TTCATTCATC AGGTCAGAAA AAGTCATCTG CAGTTGGTCT

TGGAGCCTTA TTTCACGACC ACCTTTTTTC AATATTGTTC ATTTTTACTG

GAATCTTTAT GGTGAACTAT GTTCTAATGA ACTCTGCAGC AGCGGAATCT

ACTAATACTC TTCTCATTAC CTTCCAAGAT GTTGTAGAGC TAATGAATCA

GATATTTGTA AACCCTCTGG CACCAACTAT ATTTTTAGTG GTTCTTCTCT

TCTCCAGCCA CATCATCTCG CTGACATCTG CTATCGGTAG CCAAGTGATT

TCACACCATT TATTCGGTAT AAACCTTCCT CTTTCTGGAC ATCGTCTCCT

ACTGAAGGTT TTTGCCATAG TTCCTACTCT GTACTGGGCG AAAGTTGCAG

GAGCTGAAGG GATATACCAA TTATTAATTA TATGCCAGAT TATTCAAGCC

ATGCTTCTTC CATCTTCAGT CGTCCCACTT TTTCGTGTTG CTTCATCAAG

ATCAATAATG GGAGCCCATA GAGTGTCTTT GCATCTGGAG ATACTGGTTT

TTCTTGCATT TCTCCTTATG CTATTTTCAA ATATCATATT TGTGGCAGAA

ATGCTATTTG GCGACAGTGG GTGGATGAAC AATCTGAAAG GATATACTGG

AAGCCCTGTG GTGCTCCCAT ATACCGTTTT AGTTTTAGTT GCACTTATAT

CTGTGGCTTT TCACTGTAC CTGGCTGTTA CACCATTGAG ATCTGGAAGT

CATGAAGCTG AATCCCATGA ATGGTCTGTG CATTCTCAGA GAGAACTCTT
```

```
GAATACTTCT CAAGAAAGGG AAGATGTTAA GGTGGACAAT GTTACATATG

AGGAAGATCA AAGATCAGAT GTTGTCCCTT CTCCCAGGGA TGTGCCTGAC

AGCCATCCGG AACTGGCCTT GGACTATATT GATACTTCTG ACACTGCTGT

AGAATCTGAT CACGACTCTC AACAATCTAC TGCTTATGCA TCCACTGCTC

CTGAAACCTG CTCCTCCCCG TCGTTTACTC GCGAGGAGTC AAAATCAGTT

GTTGCAGTCA ACTGGCCGGA GCCTTTGGAG AAGGTTCCTA CTTCTACTGT

GATGGAGGAA AGCACAGTAG AAAATGTGGT CTCTAGGATC ACGACTGAAA

GAGATGTTTT AGTAGAAACA GATGTTGTCT CGGGCAAGGA TAAGGAAGAT

ATCCGTACTT TGGAGTCTGA GAAGTCAATT GTTGATAGCA CCCCATATGT

GTCTGATGAC GGTCCGCCAT CCCTTACTTT CAGCAGGGGA AAGGGCTCAG

ATGCAGGAAA TGGCAGTGGT AGTCTCTCAA GGTTATCTGG TTTGGGCCGT

GCAGCAAGGA GACAGCTAGC TGCTACTCTT GATGAGTTCT GGGGGCATCT

GTTTGATTAC CATGGTAAGC TCACTCAAGA AGCTAGCACC AAAAAGTTTG

GTATCTTGCT TGGGATAGAC CTTAGAACAC CTAGCACATC TGTAAGAACG

GATAAACAAG CTGCTGAAAT ACTTAAGAGC CCACTGGTGA GAGACTCAAT

GCGGGGGGCA GCTTTTTTGT CAAGCTCAGT GGACATGATG TCCCCTAAGA

ATGAAACGTC GAATTTGGAA CTTGCATATG GGCTTCAGAG GGGACCTGGC

ATGGGATTGT CAAGCTGGTC TCAGGGTATG CAGCTACCAA ATACACAGCT

GCAGAGCTCA AGCAATAGCC TACTTGAGCA GAGTGCAAGA TTAAACTCAA

ATTTTAGTTC ATCTTATTCA GACAACAATC AGTTCTACCA ACCTGCAACA

ATTCATGGAT ACCAGCTCAC ATCTTACCTG AAACAGATGA ATGCCAGCCC

AAGCCTTTAC TCTAGCATGC CGCTGGACCC ACAACGGCTT CCAAAATCAT

CTGTGTCTGC TGTGCCAAAC TATGCTGATT CCATGATGCA TGCTCGTAAT

CATAACCTGC TTGCTTCACT GGGTGGTACT ACTACACAGC TTCCTGCAAC

ATCCCGCGTA GGCTCAATGA TGCCTGAAAG ATCGTATTAT GATCCTTCCA

GCGTTGATGG GAATGAAAAC GCTGGTTCAC CTGCTTACTC AAAAAAGTAC

CACAGCTCAC CTGATATGTC TGGAATAATC GCTGCAAGTA GAGCTGCACT

CTTGAATGAA GCAAAGTTGG GTGCTGCCAT TGGACCACAG TCATACCTCA

GCAGGCTGGC GGCAGAAAGA TCTCAATATG CAAGCTCAAC AGCCAGGCCC

GCGGCTCCAT TAGCATTTGA CGAGCTTTCA CCTCCTAAGC TCCAGAGTGA

TATCTTCTCG GCGCAGTCAA GCATGAGACC AAGTGCTAGA TCCCTTTGGG

CTAAGCAACC ATTTGAGCAA TTGTTCGGCA TGTCAAGTGC AGAGCTCAGT

AAAGGTGACT TCAATCTTCC AGGCAGATCA GGTGGCGTGG CCAAGGATGA

TTTCTCTTAT AAGGAATCTG AGACGAAGCT TCTTCAGTCC CTCAGGCTCT

GCATCATGAA GCTCCTTAAG CTAGAGGGAT CAGGGTGGCT GTTCAAGCAA

AATGGTGGTT GTGATGAAGA TCTAATCGAC CGAGTCGCTG CAGCCGAGAA

GCTATTGATG CAAGGGACTG CCGAGAATCA ACTGCTGCTT CATGGTGGTG

ATCTCCAGCA ACATTCTTCC GACCAGGCCG GCATCCAGTA CATGCGCACG

CTTCCCAACT GCGGGGAGGA CTGTGTTTGG CGCGCGTCAC TCGTCGTTAG

TTTCGGTGTC TGGTGTGTCC GCCGAGTGCT GGACATGTCT CTGGTGGAAA
```

```
GCAGGCCAGA ACTTTGGGGC AAGTATACCT ATGTCCTTAA CCGTCTTCAG

GGGATCTTGG ACCCTGCGTT CTCCAAGCCT CGGGGTGCTC TGACAATATG

CACCTGCCTT CAGAAAGACA CCAGAGTGCG CAATAGCCCA CCCCACAGTG

GGCTAACAGC CATGGGCCCG GTCCCCACAC CGATCCGGGG CGCCTTCACG

ACCGCAGGCG TGGTTCTGGA GATGATCAAG GACGTGGAGG CTGCGGTCTC

AGGCCGCAAG GGCAGGAGCG GCACGGCGGC GGGCGACGTC GCCTTCCCCA

AGGGGAAGGA GAACCTGGCC TCCGTGCTGA AGCGGTACAA GCGGCGGCTC

GCCAGCAAGG GCCAG
```

Zea mays ethylene receptor (ethylene insensitive, EIN2-like) gene; E2-25 amino acid sequence

SEQ ID NO: 42

```
MDAPDVQQSM GYKESRGGMP KFFHALGPAL LISMGYIDLG KWVAAVEAGS

CFGFDLVLLA LLFNFTAIVC QYLAACIGTV TGKNLAEICH QEYNQPTCIF

LGVQAGLSLL TSELSMIFGI ALGFNLLFEY DDLITGICFA TVMEGTINAC

IAGFALLSYV LGLLVSQPQI PLTMNVIFPK ISGESAYSLM ALLGANIMAH

NFYIHSSGQK KSSAVGLGAL FHDHLFSILF IFTGIFMVNY VLMNSAAAES

TNTLLITFQD VVELMNQIFV NPLAPTIFLV VLLFSSHIIS LTSAIGSQVI

SHHLFGINLP LSGHRLLLKV FAIVPTLYWA KVAGAEGIYQ LLIICQIIQA

MLLPSSVVPL FRVASSRSIM GAHRVSLHLE ILVFLAFLLM LFSNIIFVAE

MLFGDSGWMN NLKGYTGSPV VLPYTVLVLV ALISVAFSLY LAVTPLRSGS

HEAESHEWSV HSQRELLNTS QEREDVKVDN VTYEEDQRSD VVPSPRDVPD

SHPELALDYI DTSDTAVESD HDSQQSTAYA STAPETCSSP SFTREESKSV

VAVNWPEPLE KVPTSTVMEE STVENVVSRI TTERDVLVET DVVSGKDKED

IRTLESEKSI VDSTPYVSDD GPPSLTFSRG KGSDAGNGSG SLSRLSGLGR

AARRQLAATL DEFWGHLFDY HGKLTQEAST KKFGILLGID LRTPSTSVRT

DKQAAEILKS PLVRDSMRGA AFLSSSVDMM SPKNETSNLE LAYGLQRGPG

MGLSSWSQGM QLPNTQLQSS SNSLLEQSAR LNSNFSSSYS DNNQFYQPAT

IHGYQLTSYL KQMNASPSLY SSMPLDPQRL PKSSVSAVPN YADSMMHARN

HNLLASLGGT TTQLPATSRV GSMMPERSYY DPSSVDGNEN AGSPAYSKKY

HSSPDMSGII AASRAALLNE AKLGAAIGPQ SYLSRLAAER SQYASSTARP

AAPLAFDELS PPKLQSDIFS AQSSMRPSAR SLWAKQPFEQ LFGMSSAELS

KGDFNLPGRS GGVAKDDFSY KESETKLLQS LRLCIMKLLK LEGSGWLFKQ

NGGCDEDLID RVAAAEKLLM QGTAENQLLL HGGDLQQHSS DQAGIQYMRT

LPNCGEDCVW RASLVVSFGV WCVRRVLDMS LVESRPELWG KYTYVLNRLQ

GILDPAFSKP RGALTICTCL QKDTRVRNSP PHSGLTAMGP VPTPIRGAFT

TAGVVLEMIK DVEAAVSGRK GRSGTAAGDV AFPKGKENLA SVLKRYKRRL

ASKGQ
```

Zea mays ethylene receptor (ethylene insensitive, EIN2-like) gene; E2-25 forward primer sequence

SEQ ID NO: 43

```
TGGGTGGTACTACTACACAGCTTCCT
```

Zea mays ethylene receptor (ethylene insensitive, EIN2-like) gene; E2-25 reverse primer sequence

SEQ ID NO: 44

-continued

AGGCTTGGAGAACGCAGGGTCCAAGA

*Zea mays* ethylene receptor (ethylene insensitive,
EIN3-like) EIN3-2: forward primer sequence
SEQ ID NO: 45

ACCCCCGTACAAGAAGCCTCATGA

*Zea mays* ethylene receptor (ethylene insensitive,
EIN3-like) EIN3-2: reverse primer sequence
SEQ ID NO: 46

GTTTATGGCTGGCCGGACATACAAGT

*Zea mays* ethylene receptor (ethylene insensitive,
EIN3-like) EIN3-3: forward primer sequence
SEQ ID NO: 47

ACCCCCGTACAAGAAGCCTCATGA

*Zea mays* ethylene receptor (ethylene insensitive,
EIN3-like) EIN3-3: reverse primer sequence
SEQ ID NO: 48

ACGACCAAGACCCTATAGACTCGACACTC

---

What is claimed is:

1. An isolated nucleic acid encoding an ETR2 polypeptide, wherein the nucleic acid comprises a polynucleotide sequence with at least 90% identity to SEQ ID NO:36.

2. The nucleic acid of claim 1, wherein the polynucleotide sequence is at least 95% identical to SEQ ID NO:36.

3. The nucleic acid of claim 1, wherein the polynucleotide sequence is SEQ ID NO:36.

4. The nucleic acid of claim 1, wherein the nucleic acid encodes a polypeptide comprising a sequence with at least 95% identity to SEQ ID NO:37.

5. A recombinant expression cassette comprising a promoter sequence operably linked to the nucleic acid of claim 1.

6. A transgenic plant comprising the recombinant expression cassette of claim 5.

7. A method of increasing ETR2 activity in a plant, the method comprising the step of introducing the recombinant expression cassette of claim 4 into the plant, wherein said introduction results in an increase in ETR2 activity in the plant.

8. The method of claim 7, wherein the recombinant expression cassette encodes a polypeptide comprising the sequence of SEQ ID NO:37.

9. The method of claim 7, the method further comprising selecting a plant with a phenotype selected from the group consisting of:
   (i) multiple embryos in a single seed; and
   (ii) a staygreen phenotype.

10. The method of claim 7, wherein the construct is introduced by a sexual cross.

* * * * *

UNITED STATES PATENT AND TRADEMARK OFFICE
CERTIFICATE OF CORRECTION

| | | Page 1 of 1 |
|---|---|---|
| PATENT NO. | : 7,915,481 B2 | |
| APPLICATION NO. | : 12/366490 | |
| DATED | : March 29, 2011 | |
| INVENTOR(S) | : Gallie and Young | |

It is certified that error appears in the above-identified patent and that said Letters Patent is hereby corrected as shown below:

In column 1, after line 11, please insert the following header and paragraph:

--STATEMENT AS TO RIGHTS TO INVENTIONS MADE UNDER FEDERALLY SPONSORED RESEARCH AND DEVELOPMENT
This invention was made with government support under grants 97-35304-4657 and 98-35100-6150 awarded by the United States Department of Agriculture, and grant 0076434 awarded by the National Science Foundation. The government has certain rights in the invention.--

Signed and Sealed this
Twenty-sixth Day of July, 2011

David J. Kappos
*Director of the United States Patent and Trademark Office*